(12) United States Patent
Frazier et al.

(10) Patent No.: US 7,780,700 B2
(45) Date of Patent: Aug. 24, 2010

(54) PATENT FORAMEN OVALE CLOSURE SYSTEM

(75) Inventors: Andrew G. C. Frazier, Sunnyvale, CA (US); Alan R. Klenk, San Jose, CA (US); Alexander K. Khairkhahan, Palo Alto, CA (US); Chad C. Roue, Fremont, CA (US); Erik J. van der Burg, Los Gatos, CA (US)

(73) Assignee: ev3 Endovascular, Inc, Plymouth, MN (US)

( * ) Notice: Subject to any disclaimer, the term of this patent is extended or adjusted under 35 U.S.C. 154(b) by 951 days.

(21) Appl. No.: 10/771,845

(22) Filed: Feb. 4, 2004

(65) Prior Publication Data

US 2004/0220596 A1 Nov. 4, 2004

Related U.S. Application Data

(60) Provisional application No. 60/446,088, filed on Feb. 4, 2003.

(51) Int. Cl.
*A61B 17/08* (2006.01)
(52) U.S. Cl. .................. 606/216; 606/151; 606/213
(58) Field of Classification Search ............ 606/151, 606/213, 221, 216; 623/23.72
See application file for complete search history.

(56) References Cited

U.S. PATENT DOCUMENTS

| | | | |
|---|---|---|---|
| 2,570,465 A | 2/1951 | Lundholm | |
| 3,123,077 A | 3/1964 | Alcamo | |
| 3,124,136 A | 3/1964 | Usher | |
| 3,166,072 A | 1/1965 | Sullivan, Jr. | |
| 3,646,615 A | 3/1972 | Nees | |
| 3,716,058 A | 2/1973 | Tanner, Jr. | |
| 3,874,388 A | 4/1975 | King et al. | |
| 3,892,232 A | 7/1975 | Neufeld | |
| 4,006,747 A | 2/1977 | Kronenthal et al. | |
| 4,007,743 A | 2/1977 | Blake | |

(Continued)

FOREIGN PATENT DOCUMENTS

| | | |
|---|---|---|
| EP | 0 317 406 A1 | 4/1989 |
| EP | 0 362 113 | 4/1990 |
| EP | 0 474 887 | 3/1992 |
| EP | 0 541 063 | 5/1993 |
| EP | 0 545 091 | 6/1993 |

(Continued)

OTHER PUBLICATIONS

Search Report for PCT/US2004/003115, filed on Feb. 4, 2004 in 8 pages.

(Continued)

*Primary Examiner*—Julian W Woo
*Assistant Examiner*—Melissa Ryckman
(74) *Attorney, Agent, or Firm*—Knobbe, Martens, Olson & Bear LLP

(57) ABSTRACT

A patent foramen ovale closure device, method of delivering and a delivery system are provided. The device may include a closure device releasably connectable to an actuator. The device may include a proximal segment, an intermediate segment and a distal segment. When delivered, the proximal segment and intermediate segment form a first clip-shaped portion sized and configured to be positioned over a septum secundum of the patent foramen ovale, and the intermediate segment and distal segment form a second clip-shaped portion sized and configured to be positioned over a septum primum of the patent foramen ovale.

20 Claims, 46 Drawing Sheets

U.S. PATENT DOCUMENTS

| | | | |
|---|---|---|---|
| 4,060,089 A | 11/1977 | Noiles | |
| 4,532,926 A | 8/1985 | O'Holla | |
| 4,669,473 A | 6/1987 | Richards et al. | |
| 4,688,561 A | 8/1987 | Reese | |
| 4,781,177 A | 11/1988 | Lebigot | |
| 4,836,204 A | 6/1989 | Landymore et al. | |
| 4,873,976 A | 10/1989 | Schreiber | |
| 4,884,572 A | 12/1989 | Bays et al. | |
| 4,895,148 A | 1/1990 | Bays et al. | |
| 4,917,089 A | 4/1990 | Sideris | |
| 4,924,865 A | 5/1990 | Bays et al. | |
| 4,935,028 A | 6/1990 | Drews | |
| 4,976,715 A | 12/1990 | Bays et al. | |
| 5,013,316 A | 5/1991 | Goble et al. | |
| 5,021,059 A | 6/1991 | Kensey et al. | |
| 5,053,047 A | 10/1991 | Yoon | |
| 5,059,206 A | 10/1991 | Winters | |
| 5,085,661 A | 2/1992 | Moss | |
| 5,102,421 A | 4/1992 | Anspach, Jr. | |
| 5,108,420 A | 4/1992 | Marks | |
| 5,129,906 A | 7/1992 | Ross et al. | |
| 5,171,259 A | 12/1992 | Inoue | |
| 5,192,301 A | 3/1993 | Kamiya et al. | |
| 5,203,864 A | 4/1993 | Phillips | |
| 5,236,431 A | 8/1993 | Gogolewski et al. | |
| 5,246,441 A | 9/1993 | Ross et al. | |
| 5,254,133 A | 10/1993 | Seid | |
| 5,258,000 A | 11/1993 | Gianturco | |
| 5,261,914 A | 11/1993 | Warren | |
| 5,284,488 A | 2/1994 | Sideris | |
| 5,334,217 A | 8/1994 | Das | |
| 5,342,393 A | 8/1994 | Stack | |
| 5,350,399 A | 9/1994 | Erlebacher et al. | |
| 5,356,432 A | 10/1994 | Rutkow et al. | |
| 5,380,334 A | 1/1995 | Torrie et al. | |
| 5,397,331 A | 3/1995 | Himpens et al. | |
| 5,400,805 A | 3/1995 | Warren | |
| 5,425,744 A | 6/1995 | Fagan et al. | |
| 5,433,727 A | 7/1995 | Sideris | |
| 5,451,235 A | 9/1995 | Lock et al. | |
| 5,470,337 A | 11/1995 | Moss | |
| 5,486,193 A | 1/1996 | Bourne et al. | |
| 5,505,735 A | 4/1996 | Li | |
| 5,507,811 A | 4/1996 | Koike et al. | |
| 5,562,704 A | 10/1996 | Tamminmaki et al. | |
| 5,578,045 A | 11/1996 | Das | |
| 5,582,616 A | 12/1996 | Bolduc et al. | |
| 5,601,571 A | 2/1997 | Moss | |
| 5,620,461 A | 4/1997 | Muijs et al. | |
| 5,634,936 A | 6/1997 | Linden et al. | |
| 5,643,317 A | 7/1997 | Pavcnik et al. | |
| 5,649,950 A | 7/1997 | Bourne et al. | |
| 5,662,681 A | 9/1997 | Nash et al. | |
| 5,662,683 A | 9/1997 | Kay | |
| 5,702,421 A | 12/1997 | Schneidt | |
| 5,709,707 A | 1/1998 | Lock et al. | |
| 5,725,552 A | 3/1998 | Kotula et al. | |
| 5,728,116 A | 3/1998 | Rosenman | |
| 5,733,294 A | 3/1998 | Forber et al. | |
| 5,741,297 A | 4/1998 | Simon | |
| 5,792,179 A | 8/1998 | Sideris | |
| 5,797,960 A | 8/1998 | Stevens et al. | |
| 5,810,846 A | 9/1998 | Virnich et al. | |
| 5,823,956 A | 10/1998 | Roth et al. | |
| 5,827,298 A | 10/1998 | Hart et al. | |
| 5,829,447 A | 11/1998 | Stevens et al. | |
| 5,843,084 A | 12/1998 | Hart et al. | |
| 5,846,261 A | 12/1998 | Kotula et al. | |
| 5,853,422 A | 12/1998 | Huebsch et al. | |
| 5,855,614 A | 1/1999 | Stevens et al. | |
| 5,860,948 A | 1/1999 | Buscemi | |
| 5,861,003 A | 1/1999 | Latson et al. | |
| 5,879,366 A | 3/1999 | Shaw et al. | |
| 5,893,850 A | 4/1999 | Cachia | |
| 5,902,317 A | 5/1999 | Kleshinski et al. | |
| 5,904,703 A | 5/1999 | Gilson | |
| 5,919,200 A | 7/1999 | Stambaugh et al. | |
| 5,944,738 A | 8/1999 | Amplatz et al. | |
| 5,947,997 A | 9/1999 | Pavcnik et al. | |
| 5,976,174 A | 11/1999 | Ruiz | |
| 5,980,524 A | 11/1999 | Justin et al. | |
| 6,024,756 A | 2/2000 | Huebsch et al. | |
| 6,059,823 A | 5/2000 | Holman et al. | |
| 6,077,281 A | 6/2000 | Das | |
| 6,077,291 A | 6/2000 | Das | |
| 6,079,414 A | 6/2000 | Roth | |
| 6,080,182 A * | 6/2000 | Shaw et al. | 606/213 |
| 6,087,552 A | 7/2000 | Gregory | |
| 6,096,052 A | 8/2000 | Callister et al. | |
| 6,106,532 A | 8/2000 | Koike et al. | |
| 6,110,212 A | 8/2000 | Gregory | |
| 6,123,715 A | 9/2000 | Amplatz | |
| 6,152,144 A | 11/2000 | Lesh et al. | |
| 6,156,055 A | 12/2000 | Ravenscroft | |
| 6,171,329 B1 * | 1/2001 | Shaw et al. | 606/213 |
| 6,174,322 B1 | 1/2001 | Schneidt | |
| 6,190,400 B1 | 2/2001 | Van de Moer et al. | |
| 6,200,336 B1 | 3/2001 | Pavcnik et al. | |
| 6,206,895 B1 | 3/2001 | Levinson | |
| 6,206,907 B1 | 3/2001 | Marino et al. | |
| 6,210,338 B1 | 4/2001 | Afremov et al. | |
| 6,214,029 B1 | 4/2001 | Thill et al. | |
| 6,221,092 B1 * | 4/2001 | Koike et al. | 606/213 |
| 6,231,561 B1 | 5/2001 | Frazier et al. | |
| 6,231,589 B1 | 5/2001 | Wessman et al. | |
| 6,238,416 B1 | 5/2001 | Sideris | |
| 6,241,747 B1 | 6/2001 | Ruff | |
| 6,245,079 B1 | 6/2001 | Nobles et al. | |
| 6,270,515 B1 | 8/2001 | Linden et al. | |
| 6,277,140 B2 | 8/2001 | Ginn et al. | |
| 6,280,460 B1 | 8/2001 | Bolduc et al. | |
| 6,290,674 B1 | 9/2001 | Roue et al. | |
| 6,290,702 B1 | 9/2001 | Fucci et al. | |
| 6,296,641 B2 | 10/2001 | Burkhead et al. | |
| 6,299,597 B1 | 10/2001 | Buscemi et al. | |
| 6,306,177 B1 | 10/2001 | Felt et al. | |
| 6,312,446 B1 * | 11/2001 | Huebsch et al. | 606/213 |
| 6,319,263 B1 | 11/2001 | Levinson | |
| 6,319,270 B1 | 11/2001 | Grafton et al. | |
| 6,319,276 B1 | 11/2001 | Holman et al. | |
| 6,322,563 B1 | 11/2001 | Cummings et al. | |
| 6,328,727 B1 | 12/2001 | Frazier et al. | |
| 6,334,864 B1 | 1/2002 | Amplatz et al. | |
| 6,342,064 B1 | 1/2002 | Koike et al. | |
| 6,346,074 B1 | 2/2002 | Roth | |
| 6,348,053 B1 | 2/2002 | Cachia | |
| 6,355,052 B1 * | 3/2002 | Neuss et al. | 606/213 |
| 6,368,339 B1 | 4/2002 | Amplatz | |
| 6,375,671 B1 | 4/2002 | Kobayashi et al. | |
| 6,379,368 B1 | 4/2002 | Corcoran et al. | |
| 6,391,048 B1 | 5/2002 | Ginn et al. | |
| 6,419,669 B1 | 7/2002 | Frazier et al. | |
| 6,440,152 B1 | 8/2002 | Gainor et al. | |
| 6,458,100 B2 | 10/2002 | Roue et al. | |
| 6,461,364 B1 | 10/2002 | Ginn et al. | |
| 6,468,303 B1 | 10/2002 | Amplatz et al. | |
| 6,482,224 B1 | 11/2002 | Michler et al. | |
| 6,485,504 B1 | 11/2002 | Johnson et al. | |
| 6,508,828 B1 * | 1/2003 | Akerfeldt et al. | 606/215 |
| 6,517,564 B1 | 2/2003 | Grafton et al. | |
| 6,533,762 B2 | 3/2003 | Kanner | |
| 6,537,300 B2 | 3/2003 | Girton | |
| 6,551,343 B1 | 4/2003 | Tormala et al. | |
| 6,551,344 B2 | 4/2003 | Thill | |

| | | |
|---|---|---|
| 6,569,188 B2 | 5/2003 | Grafton et al. |
| 6,596,014 B2 | 7/2003 | Levinson et al. |
| 6,626,917 B1 | 9/2003 | Craig |
| 6,632,238 B2 | 10/2003 | Ginn et al. |
| 6,635,066 B2 | 10/2003 | Tanner et al. |
| 6,645,225 B1 | 11/2003 | Atkinson |
| 6,656,206 B2 | 12/2003 | Corcoran et al. |
| 6,663,633 B1 | 12/2003 | Pierson, III |
| 6,695,867 B2 | 2/2004 | Ginn et al. |
| 6,702,835 B2 | 3/2004 | Ginn |
| 6,712,836 B1 | 3/2004 | Berg et al. |
| 6,719,777 B2 | 4/2004 | Ginn et al. |
| 6,776,784 B2 | 8/2004 | Ginn |
| 6,911,037 B2 | 6/2005 | Gainor et al. |
| 7,087,072 B2 * | 8/2006 | Marino et al. ............... 606/213 |
| 7,288,105 B2 | 10/2007 | Oman et al. |
| 7,377,936 B2 | 5/2008 | Gainor et al. |
| 7,479,155 B2 | 1/2009 | Gainor et al. |
| 7,582,103 B2 | 9/2009 | Young et al. |
| 2001/0014800 A1 | 8/2001 | Frazier et al. |
| 2001/0021872 A1 | 9/2001 | Bailey et al. |
| 2001/0023332 A1 | 9/2001 | Hahnen |
| 2001/0031973 A1 | 10/2001 | Nobles et al. |
| 2001/0034537 A1 | 10/2001 | Shaw et al. |
| 2001/0037129 A1 | 11/2001 | Thill |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0039450 A1 | 11/2001 | Pavcnik et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0010481 A1 | 1/2002 | Jayaraman |
| 2002/0026208 A1 | 2/2002 | Roe et al. |
| 2002/0055767 A1 | 5/2002 | Forde et al. |
| 2002/0068950 A1 | 6/2002 | Corcoran et al. |
| 2002/0165574 A1 | 11/2002 | Ressemann et al. |
| 2002/0165598 A1 | 11/2002 | Wahr et al. |
| 2002/0169475 A1 | 11/2002 | Gainor et al. |
| 2002/0183786 A1 | 12/2002 | Girton |
| 2002/0183787 A1 * | 12/2002 | Wahr et al. ................... 606/213 |
| 2002/0198563 A1 | 12/2002 | Gainor et al. |
| 2003/0023262 A1 | 1/2003 | Welch |
| 2003/0028213 A1 | 2/2003 | Thill et al. |
| 2003/0045893 A1 | 3/2003 | Ginn |
| 2003/0050600 A1 | 3/2003 | Ressemann et al. |
| 2003/0050665 A1 | 3/2003 | Ginn |
| 2003/0055455 A1 | 3/2003 | Yang et al. |
| 2003/0093096 A1 | 5/2003 | McGuckin, Jr. et al. |
| 2003/0144694 A1 | 7/2003 | Chanduszko et al. |
| 2003/0191495 A1 * | 10/2003 | Ryan et al. ................... 606/213 |
| 2003/0195530 A1 | 10/2003 | Thill |
| 2003/0208232 A1 | 11/2003 | Blaeser et al. |
| 2003/0225421 A1 * | 12/2003 | Peavey et al. ............... 606/151 |
| 2004/0039414 A1 | 2/2004 | Carley et al. |
| 2004/0073236 A1 | 4/2004 | Carley et al. |
| 2004/0073242 A1 | 4/2004 | Chanduszko |
| 2004/0092973 A1 | 5/2004 | Chanduszko |
| 2004/0098121 A1 | 5/2004 | Opolski |
| 2004/0127917 A1 | 7/2004 | Ginn |
| 2004/0133236 A1 | 7/2004 | Chanduszko |
| 2004/0176788 A1 | 9/2004 | Opolski |
| 2004/0176799 A1 | 9/2004 | Chanduszko |
| 2004/0193194 A1 | 9/2004 | Laufer |
| 2004/0243122 A1 | 12/2004 | Auth et al. |
| 2004/0249398 A1 | 12/2004 | Ginn |
| 2004/0254594 A1 | 12/2004 | Alfaro |
| 2004/0267191 A1 | 12/2004 | Gifford, III et al. |
| 2004/0267366 A1 | 12/2004 | Kruger |
| 2005/0006900 A1 | 1/2005 | Lewis |
| 2005/0021016 A1 | 1/2005 | Malecki et al. |
| 2005/0033327 A1 | 2/2005 | Gainor et al. |
| 2005/0059984 A1 | 3/2005 | Chanduszko |
| 2005/0119675 A1 | 6/2005 | Adams et al. |
| 2005/0187568 A1 | 8/2005 | Klenk et al. |
| 2005/0192626 A1 | 9/2005 | Widomski et al. |
| 2005/0251201 A1 | 11/2005 | Roue et al. |
| 2007/0106327 A1 | 5/2007 | Thill et al. |
| 2007/0112382 A1 | 5/2007 | Thill et al. |
| 2008/0058866 A1 | 3/2008 | Young et al. |
| 2008/0195123 A1 | 8/2008 | Gainor et al. |

FOREIGN PATENT DOCUMENTS

| | | |
|---|---|---|
| EP | 0 632 999 A1 | 1/1995 |
| EP | 0 655 222 | 5/1995 |
| EP | 0 793 457 | 9/1997 |
| EP | 0 876 793 | 11/1998 |
| EP | 1 046 375 | 10/2000 |
| EP | 1 214 911 | 6/2002 |
| EP | 1 281 355 A2 | 2/2003 |
| FR | 1 317 354 | 1/1963 |
| GB | 2 269 321 | 2/1994 |
| JP | 7171173 | 6/1996 |
| JP | 8141070 | 8/1996 |
| JP | 8196623 | 8/1996 |
| WO | WO 85/03857 | 9/1985 |
| WO | WO 89/01767 | 3/1989 |
| WO | WO 90/14796 | 12/1990 |
| WO | WO 93/13712 | 7/1993 |
| WO | WO 93/14705 | 8/1993 |
| WO | WO 95/28885 | 11/1995 |
| WO | WO 96/32882 | 10/1996 |
| WO | WO 97/18762 | 5/1997 |
| WO | WO 97/41779 | 11/1997 |
| WO | WO 97/42878 | 11/1997 |
| WO | WO 98/08462 | 3/1998 |
| WO | WO 98/27868 | 7/1998 |
| WO | WO 99/07289 | 2/1999 |
| WO | WO 99/18862 | 4/1999 |
| WO | WO 99/18864 | 4/1999 |
| WO | WO 99/18871 | 4/1999 |
| WO | WO 99/38454 | 8/1999 |
| WO | WO 99/40849 | 8/1999 |
| WO | WO 00/56376 | 9/2000 |
| WO | WO 00/69365 | 11/2000 |
| WO | WO 01/17435 | 3/2001 |
| WO | WO 01/21246 | 3/2001 |
| WO | WO 01/30267 | 5/2001 |
| WO | WO 02/32496 | 4/2002 |
| WO | WO 02/38051 | 5/2002 |
| WO | WO 02/098298 | 12/2002 |
| WO | WO 03/103476 A2 | 12/2003 |
| WO | WO 2004/026147 | 4/2004 |
| WO | WO 2004/086951 | 10/2004 |
| WO | WO 2004/087235 | 10/2004 |
| WO | WO 2004/091411 | 10/2004 |

OTHER PUBLICATIONS

Ruiz, C. E. et al. "The Puncture Technique: A New Method for Transcatheter Closure of Patent Foramen Ovale," Cath. And Cardiovasc. Interv. 53:369-372 (2001).

International Search Report and Written Opinion of the International Searching Authority for PCT/US2004/003115, filed on Feb. 4, 2004, in 20 pages.

Extended European Search Report dated Aug. 29, 2008, European Patent Application No. 08152456.3 published EP 1955661.

Office Action dated Feb. 22, 2008: U.S. Appl. No. 11/607,237, U.S. Publication 2007-0112382 A1.

List of claims as allowed by the U.S. Patent and Trademark Office on May 21, 2007 as set forth by the Notice of Allowance and Fee(s) Due in U.S. Appl. No. 10/209,797 (published as U.S. Pub. No. 2003/0028213 on Feb. 6, 2003).

* cited by examiner

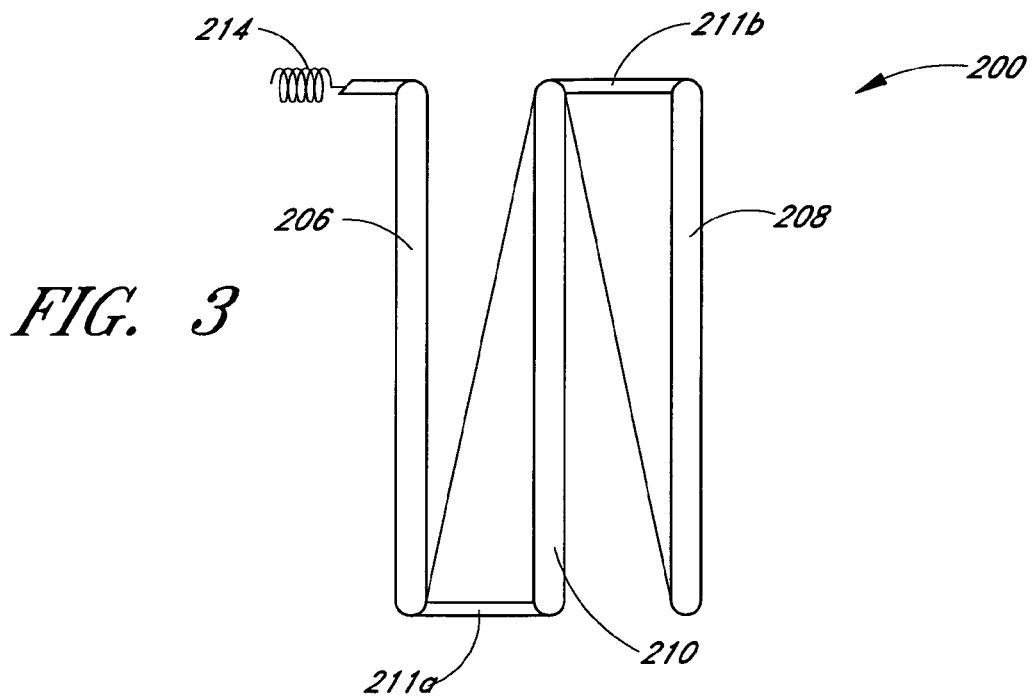
FIG. 3
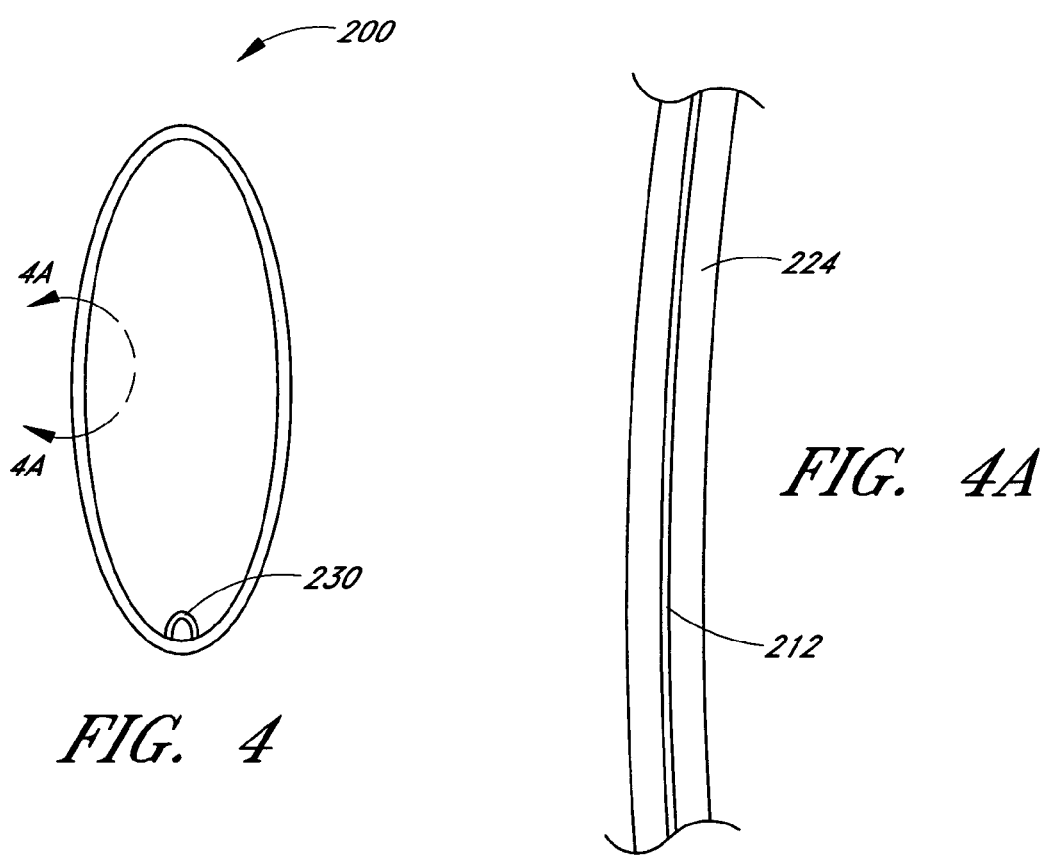
FIG. 4
FIG. 4A

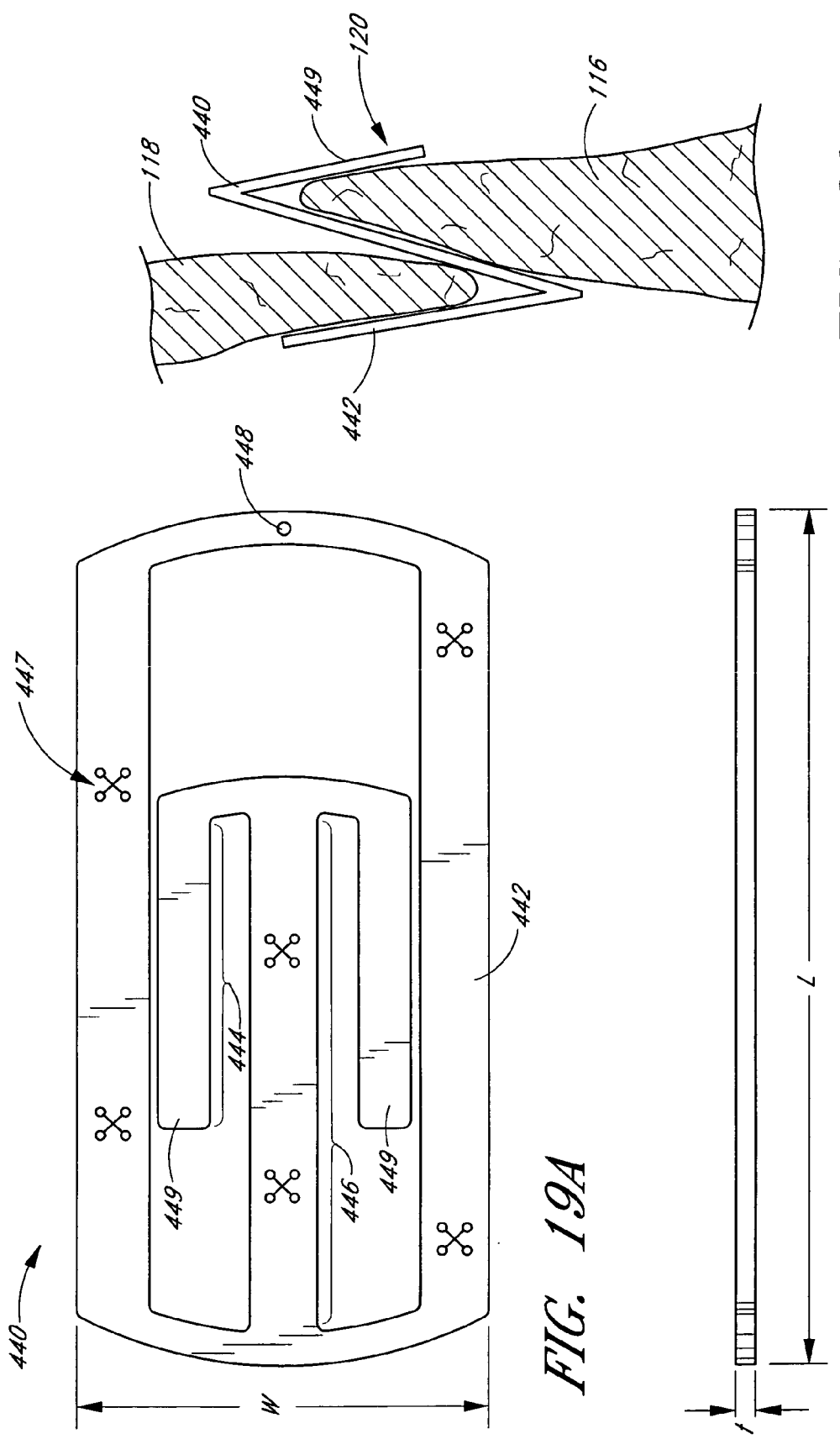

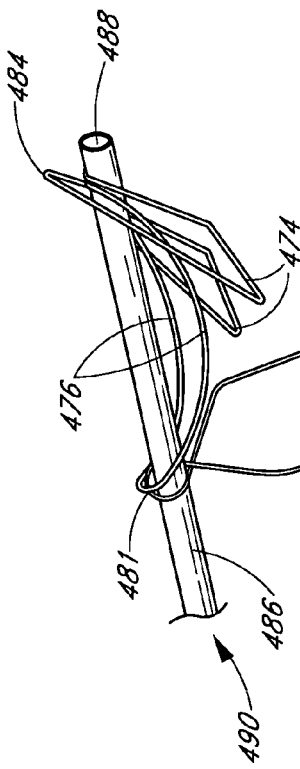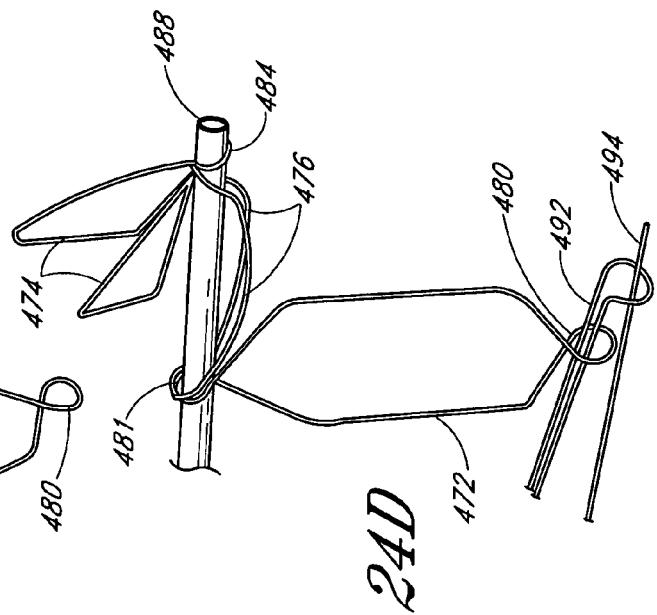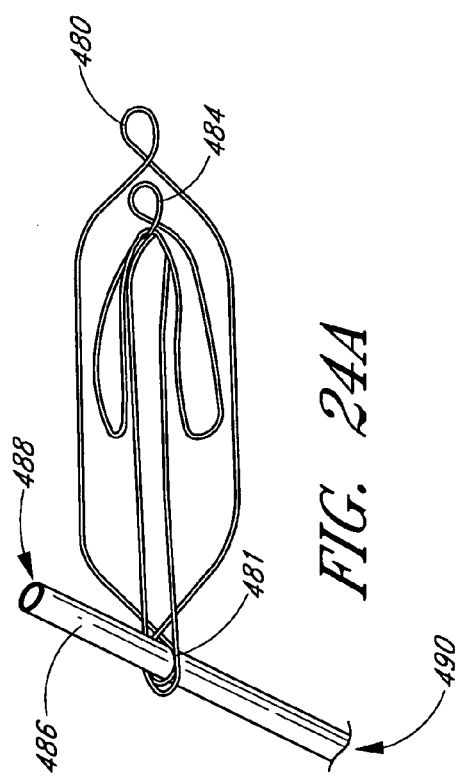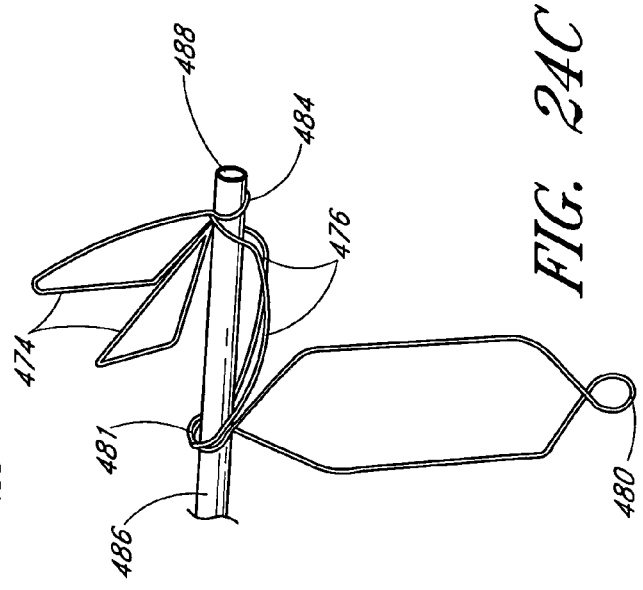

PATENT FORAMEN OVALE CLOSURE SYSTEM

CROSS-REFERENCE TO RELATED APPLICATION

This application claims the benefit of U.S. Provisional Application No. 60/445,088, filed Feb. 4, 2003, the entirety of which is hereby incorporated by reference.

BACKGROUND OF THE INVENTION

1. Field of the Invention

Embodiments of the present invention relate to methods and devices for closing a body lumen or cavity and, in particular, for closing a patent foramen ovale.

2. Description of the Related Art

Embolic stroke is the nation's third leading killer for adults, and is a major cause of disability. There are over 700,000 strokes per year in the United States alone. Of these, roughly 100,000 are hemorrhagic, and 600,000 are ischemic (either due to vessel narrowing or to embolism). About 50,000 of the ischemic strokes are believed to be caused by a patent foramen ovale. However, the risk of recurrent stroke is higher in patients whose strokes are caused by a patent foramen ovale.

Pharmacological therapies for stroke prevention such as oral or systemic administration of warfarin or the like have been inadequate due to serious side effects of the medications and lack of patient compliance in taking the medication.

In general, the heart is divided into four chambers, the two upper being the left and right atria and the two lower being the left and right ventricles. The atria are separated from each other by a muscular wall, the interatrial septum, and the ventricles by the interventricular septum.

Either congenitally or by acquisition, abnormal openings, holes or shunts can occur between the chambers of the heart or the great vessels (interatrial and interventricular septal defects or patent ductus arteriosus and aortico-pulmonary window respectively), causing shunting of blood through the opening. A patent foramen ovale is a condition wherein an abnormal opening is present in the septal wall between the two atria of the heart. Blood can flow directly between these two atria, compromising the normal flow of blood and efficiency of the patient's heart. The deformity is usually congenital, resulting from a failure of completion of the formation of the septum, or wall, between the two sides during fetal life when the heart forms from a folded tube into a four-chambered, two unit system.

In contrast to other septal defects which tend to have a generally longitudinal axis, a patent foramen ovale tends to behave like a flap valve. Accordingly, the axis of the patent foramen ovale tends to be at an angle, and almost parallel to the septal wall.

These deformities can carry significant sequelae. For example, with a patent foramen ovale, blood is shunted from the left atrium of the heart to the right, producing an over-load of the right heart. In addition to left-to-right shunts such as also occur in patent foramen ovale, the left side of the heart has to work harder because some of the blood which it pumps will recirculate through the lungs instead of going out to the rest of the body. The ill effects of these defects usually cause added strain on the heart with ultimate failure if not corrected.

Previously, patent foramen ovale have required relatively extensive surgical techniques for correction. To date the most common method for closing intracardiac shunts, such as a patent foramen ovale, entails the relatively drastic technique of open-heart surgery, requiring opening the chest or sternum and diverting the blood from the heart with the use of a cardiopulmonary bypass. The heart is then opened, the defect is sewn shut by direct suturing with or without a patch of synthetic material (usually of Dacron, Teflon, silk, nylon or pericardium), and then the heart is closed. The patient is then taken off the cardiopulmonary bypass machine, and the chest is closed.

In place of direct suturing, closures of a patent foramen ovale by means of a mechanical prosthesis have also been disclosed. A number of these devices, designed for closures of interauricular septal defects, have been used to correct patent foramen ovale.

Although these devices have been known to effectively close other septal defects, there are few closure devices which have been developed specifically for closing patent foramen ovale. Although these devices have been effective in some cases, there is still much room for improvement.

Notwithstanding the foregoing, there remains a need for a method and improved apparatus for correcting patent foramen ovale.

SUMMARY OF THE INVENTION

Embodiments of the present invention provide a minimally invasive closure device for closing a patent foramen ovale. Improved delivery and positioning systems are also provided.

In accordance with one embodiment, a closure device for closing a patent foramen ovale is provided. The device includes a proximal end, a distal end, a proximal segment, an intermediate segment, and a distal segment, wherein each of the segments is sequentially aligned. The device has a generally elongate configuration and a clip configuration. When the device is in its elongate configuration, the proximal and distal ends are pulled away from each other such that the proximal segment, intermediate segment, and distal segment become relatively more linear. When the device is in its clip configuration, the proximal segment and intermediate segment are drawn into a first clip-shaped portion sized and configured to be positioned over a septum secundum of the patent foramen ovale. The intermediate segment and distal segment are drawn into a second clip-shaped portion sized and configured to be positioned over a septum primum of the patent foramen ovale. The first clip-shaped portion and the second clip-shaped portion provide a force against the septum primum and septum secundum to pinch the two relatively closer together.

In one embodiment, the closure device may be formed from a wire structure, more preferably one integral wire. In one embodiment, the proximal and distal segments are identical in shape, and may have identical shapes that form mirror images of each other across the patent foramen ovale to equally apply compressive force to both sides of the patent foramen ovale. In another embodiment, the proximal segment has a larger dimension than the distal segment, and more preferably has both a greater length and width than the distal segment. The distal segment may include a pair of wings adapted to extend over the tip of the septum primum. The device may also include loops, eyelets or other structure adapted for releasable engagement with a delivery system, as described below. The device may also include anchors or other tissue engaging structures to facilitate securement of the device in the patent foramen ovale.

In accordance with another embodiment, a closure device for closing a patent foramen ovale is provided. The device includes a proximal segment, a distal segment, and an intermediate segment which may be integrally formed, preferably from an integral wire structure. A covering, sleeve or laminate structure is provided on at least one of the segments of the device. In one embodiment, a sleeve is provided over the intermediate segment and is adapted to be positioned in the tunnel of the patent foramen ovale. In another embodiment a laminate structure may be provided over at least the proximal or anterior portion. The sleeve may be made of a material that facilitates cellular in-growth, such as ePTFE.

In accordance with one embodiment, a method of closing a patent foramen ovale having a septum primum and a septum secundum is provided. The method includes providing a closure device having a proximal end and a distal end and having a generally elongate configuration and a clip configuration. When the device is in its elongate configuration, the proximal and distal ends are pulled away from each other, and when the device is in its clip configuration the device has generally an S-shape. The device is releasably attached relative to a delivery device. The device is then delivered to the patent foramen ovale with the delivery device, the closure device being held relative to the delivery device in its elongate configuration. The closure device is deployed in the patent foramen ovale, such that the device when deployed includes a first clip-shaped portion positioned around the septum secundum and a second clip-shaped portion positioned around the septum primum.

In accordance with a further embodiment, a method of closing a patent foramen ovale having a septum primum and a septum secundum in provided. The method includes providing a closure device having a proximal end, a distal end, a proximal segment, an intermediate segment and a distal segment. The method further includes deploying the closure device within the patent foramen ovale such that the distal segment lies along a surface of the septum primum within the left atrium of the patient. The proximal segment preferably lies along a surface of the septum secundum within the right atrium of the patient. The intermediate segment preferably lies in a channel or tunnel between the septum primum and the septum secundum. When the closure device is deployed, it exerts a force between the proximal segment and intermediate segment and between the intermediate segment and distal segment to draw or pinch the septum primum and septum secundum together.

In accordance with another embodiment, a method of closing a patent foramen ovale is provided. The method includes positioning a closure device at a patent foramen ovale and deploying the closure device, such that the septum primum and septum secundum are secured together by the closure device.

In a preferred delivery method, the closure device is self-expanding and may be releasably engaged with a percutaneous delivery device. In one embodiment, where the closure device has proximal, intermediate and distal segments, each of the segments is releasably engaged with the delivery device, such as by extending a core or guidewire through eyelets formed in each of the segments of the device. In another embodiment, the closure device may be internally or externally threaded to releasably engage a corresponding delivery device. This threading may be provided at the proximal end of the device, at the distal end of the device, or may be provided in proximal, intermediate and/or distal segments. The closure device may be delivered through an outer deployment catheter which guides the device to the patent foramen ovale.

In accordance with one embodiment, a closure device for closing a patent foramen ovale is provided. The device includes a proximal segment and a distal segment which may be integrally formed. The device generally has a hook configuration, wherein the distal segment is sized and configured to be positioned over a septum primum of the patent foramen ovale. The proximal segment is sized and configured to extend through the tunnel of the patent foramen ovale, and at its proximal end, may increase in width to form wings to secure the closure device in place. In this configuration, the proximal segment is sized and configured to be positioned along a surface of the septum of the patent foramen ovale in the right atrium. The device may also include a sleeve or laminate structure between the proximal end and the distal segment, the sleeve or laminate structure adapted to be positioned in the patent foramen ovale tunnel. The sleeve or laminate structure is made of material adapted to facilitate cellular in-growth, such as ePTFE.

In accordance with a further embodiment, a method of closing a patent foramen ovale is provided. The method includes positioning a closure device at a patent foramen ovale and deploying the closure device, such that the septum primum is secured by the closure device. In one embodiment, only the septum primum is secured by the closure device, with the device forming a hook over the tip of the septum primum to hold the septum primum in place. Preferably, the closure device may have wings in a proximal segment thereof that extend beyond the width of the tunnel of the patent foramen ovale. The wings as delivered are positioned in the right atrium against a surface of the septum primum.

In another embodiment, delivery systems incorporating the devices used in the delivery methods are provided. According to one delivery system, a deployment catheter having a proximal end and a distal end is provided. An actuator extends through the deployment catheter. A closure device is releasably attached to the actuator. The actuator is adapted to advance the closure device from the distal end of the deployment catheter and position a distal segment of the closure device over a septum primum of the patent foramen ovale and position a proximal segment of the closure device over a septum secundum of the patent foramen ovale. The closure device is actuatable to pinch together the septum primum and septum secundum once delivered, and may be self-expanding and/or manually actuated. It will also be appreciated that the closure device can be delivered without the deployment catheter, such that the closure device is releasably secured and released from the actuator to deliver the device.

BRIEF DESCRIPTION OF THE DRAWINGS

FIG. 3 is a side elevational view of the closure device shown in FIG. 2A.

FIG. 4 is a cross-sectional view of one of the segments of the closure device shown in FIG. 2A.

FIG. 4A is an enlarged view of a portion of the segment of FIG. 4.

FIG. 10 is a partial cross-sectional view of an embodiment of the catheter of FIG. 8, with a closure device being delivered there through.

FIG. 11C is a partial cross-sectional view of another embodiment of the catheter of FIG. 8, with another embodiment of a closure device being delivered there through.

FIG. 19A is a front elevational view of a closure device in accordance with another embodiment of the present invention.

FIG. 19B is a side elevational view of the closure device shown in FIG. 19A.

FIG. 20 is a cross-sectional view of a patent foramen ovale closed with the closure device of FIG. 19.

FIGS. 24A-D are schematic views of a patent foramen ovale closure procedure in accordance with one embodiment of the present invention, shown inversely to the deployment orientation to facilitate explanation.

DETAILED DESCRIPTION OF THE PREFERRED EMBODIMENTS

For simplicity, preferred embodiments of the present invention will be described primarily in the context of a patent foramen ovale closure procedure. However, the devices and methods herein are readily applicable to a wider variety of closure or attachment procedures, and all such applications are contemplated by the present inventors. For example, additional heart muscle procedures such as atrial septal defect closure and patent ductus arteriosis closure are contemplated. Vascular procedures such as isolation or repair of aneurysms, anastomosis of vessel to vessel or vessel to prosthetic tubular graft joints may also be accomplished using the devices of the embodiments described herein. Attachment of implantable prostheses, such as attachment of the annulus of a prosthetic tissue or mechanical heart valve may be accomplished. A variety of other tissue openings, lumens, hollow organs and surgically created passageways may be closed. Adaptation of the devices and methods disclosed herein to accomplish procedures such as the foregoing will be apparent to those of skill in the art in view of the disclosure herein.

Figure 1:
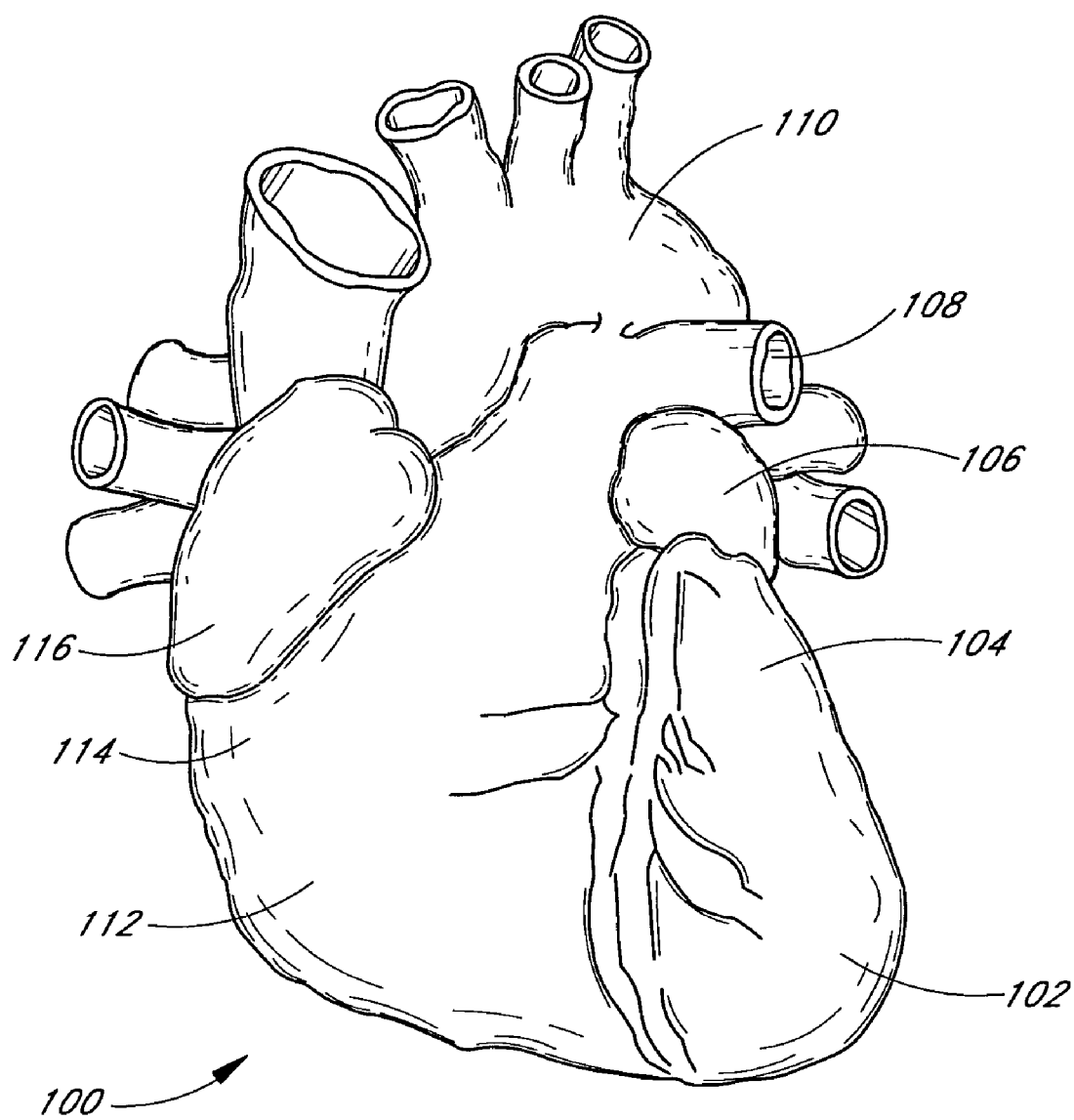
FIG. 1 is an anterior illustration of a heart, with the proximal parts of the great vessels.

Referring to FIG. 1, a heart 100 is illustrated to show certain portions including the left ventricle 102, the left atrium 104, the left atrial appendage 106, the pulmonary artery 108, the aorta 110, the right ventricle 112, the right atrium 114, and the right atrial appendage 116. As is understood in the art, the left atrium 104 is located above the left ventricle 102 and the two are separate by the mitral valve (not illustrated).

First Clip Embodiments

Referring to FIGS. 2A and 3-7, there is illustrated one embodiment of an occlusion or closure device 200 sized and configured to close a patent foramen ovale in accordance with one embodiment of the present invention. The closure device preferably comprises a wire shaped to form a clip, which is preferably shaped like a paperclip. As illustrated, in one embodiment the closure device can be considered to have generally an S-shape or two adjacent U-shaped or clip portions, as described further below. The closure device 200 has a proximal end 202 and a distal end 204. The designation proximal or distal is not intended to indicate any particular anatomical orientation or deployment orientation within the deployment catheter, as described below.

The closure device 200 generally has three sections: a proximal segment 206, a distal segment 208, and an intermediate segment 210. As illustrated in FIG. 4, each of these segments is preferably generally annular-shaped or oval-shaped forming a loop, and may be generally parallel to each other when the device 200 is in its deployment state, shown in FIG. 2A. It will be appreciated that the segments may have any suitable size and configuration for closing a patent foramen ovale, including round, oblong, rectangular, triangular and square. Each of the segments 206, 208, 210 may be formed from wire 212 and may be separately or integrally formed.

In one embodiment, the three segments 206, 208, 210 are sequentially aligned such that a distal end 206b of proximal segment 206 is connected to a proximal end 210a of intermediate segment 210, and a distal end 210b of intermediate segment 210 is connected to a proximal end 208a of distal segment 208. As illustrated, these segments 206, 208, 210 are connected by connecting portions 211a and 211b, and may be integrally formed with the connecting portions. Alternatively, they may be joined together by any suitable technique. The closure device 200 is also preferably provided with a detachment element 214 at its proximal end 202, illustrated as an externally threaded portion. Alternatively, the proximal end 202 of the device 200 may be provided with a threaded aperture through which a delivery core is threadably engaged, a loop or eyelet, or other suitable structure as will be discussed herein for releasably connecting the device to a deployment system.

In one embodiment, a wire 212 is used to form the segments 206, 208 and 210, as well as connecting portions 211, and comprises a metal such as stainless steel, Nitinol, Elgiloy, or others which can be determined through routine experimentation by those of skill in the art. The wire may also be biodegradable. Wires having a circular or rectangular cross-section may be utilized depending upon the manufacturing technique. It will be appreciated that the closure device 200 need not be formed from a wire, and can be an integral structure, for example, laser cut from a tube or other stock. It is also envisioned that other non-metallic biocompatible materials may be used to form wire 212. The wire 212 may be solid or hollow.

As shown in FIG. 4A, in one embodiment at least a portion of the wire 212 is covered with a sleeve 224. The sleeve 224 may comprise any of a variety of materials which facilitate cellular in-growth, such as ePTFE. The suitability of alternate materials for sleeve 224 can be determined through routine experimentation by those of skill in the art. The sleeve 224 may be provided on either one or all sections of the closure device. For example, the intermediate segment 210 alone or the entire device 200 may be provided with sleeve 224. In one embodiment, the sleeve 224 comprises two layers. The two layers may be bonded to each other around the wire 212 in any of a variety of ways, such as by heat bonding with or without an intermediate bonding layer such as polyethylene or FEP, adhesives, sutures, and other techniques which will be apparent to those of skill in the art in view of the disclosure herein. The sleeve 224 in one embodiment preferably is securely attached to the device 200 and retains a sufficient porosity to facilitate cellular ingrowth and/or attachment.

Figure 2A:
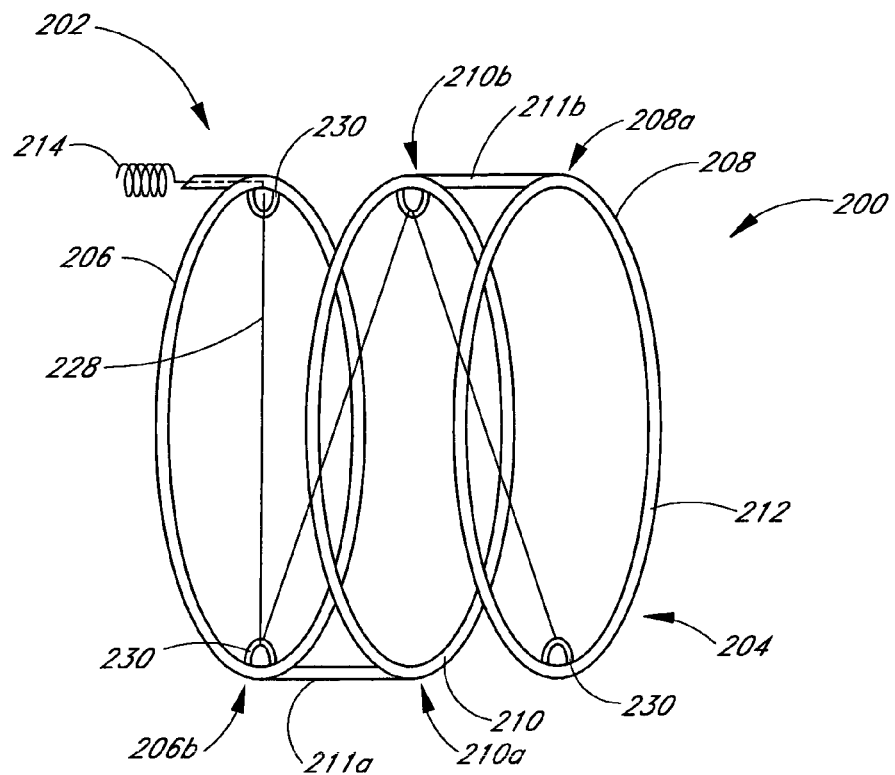
FIG. 2A is a perspective view of a closure device in accordance with one embodiment the present invention.

Referring back to FIG. 2A, the device 200 is illustrated in its deployment state. The device 200 may be self-expanding, having a remembered shape as illustrated in FIG. 2A. Alternatively, the device 200 may be mechanically actuated to assume its deployment state. As illustrated, the device 200 preferably includes a locking element 228 and retention elements, preferably in the form of eyelets 230, for retaining the locking element 228 to the closure device 200. In one embodiment, the eyelets 230 are offset from one another on adjacent segments of the device. In another embodiment, the eyelets 230 are in line with the longitudinal axis of the device 200. Other details regarding a device having eyelets described above, as well as similar devices, may be found in U.S. Pat. Nos. 6,214,029, 6,551,344 and 6,440,152, which are hereby incorporated by reference in its entirety. The locking element 228 is used to longitudinally shorten and radially expand the device. The locking element 228 preferably comprises a locking string which is preferably used to both longitudinally shorten and radially expand and lock the device at the patent foramen ovale. Other details regarding the locking element described above as well as similar devices may be found in U.S. Pat. No. 5,861,003, which is hereby incorporated by reference in its entirety. Preferably, upon deployment and positioning of the device 200, the locking element 228 secures the locking string to retain the device 200 is the deployed position. The locking string may also be drawn proximally to increase the clamping force of the device 200 on the septa of the patent foramen ovale. It will be appreciated that the device 200 may still be self-expanding, with the locking string also mechanically actuating the device 200.

In some embodiments, the device 200 may be made by laser cutting flat stock sheet. In another embodiment, the device 200 and the eyelets 230 may comprise a metal wire such as stainless steel, Nitinol, Elgiloy, or others which can be determined through routine experimentation by those of skill in the art.

Figure 2B:
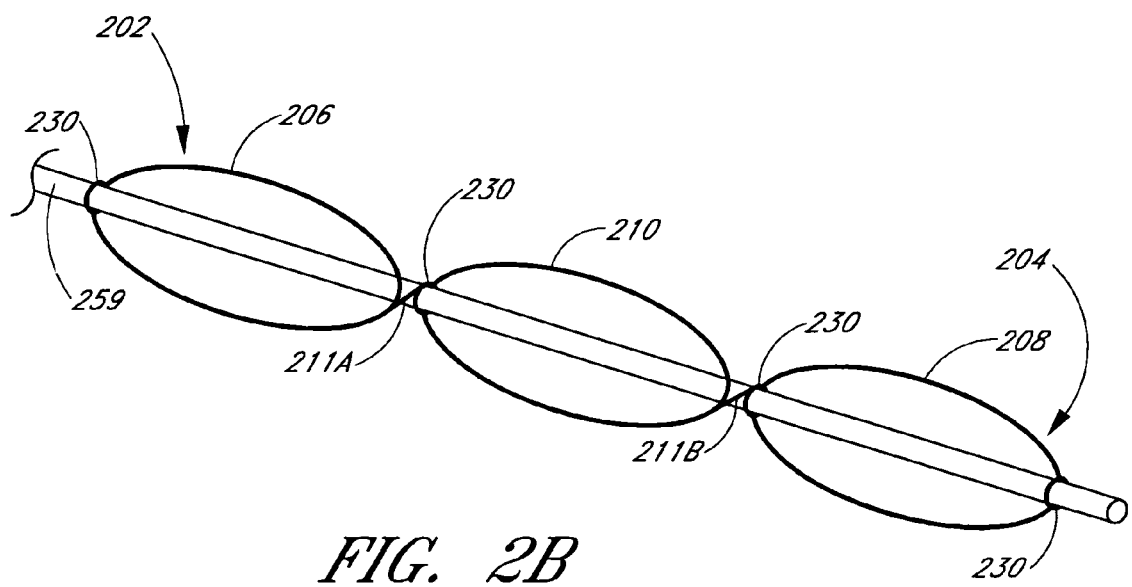
FIG. 2B is a perspective view of a closure device in accordance with one embodiment of the present invention in a delivery state.

FIG. 2B illustrates an alternative embodiment of a self-expanding closure device including at least one eyelet, and more preferably, a plurality of eyelets 230 to assist with collapse of device 200 into a delivery device. The device 200 may have a proximal segment 206, an intermediate segment 210, and a distal segment 208 like the embodiment of FIG. 2A, and preferably is formed from a single wire forming three similar shaped segments, which may be generally looped or oval in shape. The eyelets 230 are integrally formed by small loops made in the wire, preferably at the proximal end 202, distal end 204, and at connecting portions 211*a* and 211*b*. In one embodiment, the eyelets 230 are configured to receive an actuator or core 259, such as hypotubing, solid wire or a guidewire, to releasably secure the device 200 and stress the wire in a longitudinally stretched position during deployment as shown in FIG. 2B. Upon confirmation of optimal positioning in the patent foramen ovale or other structure, the core may be retracted proximally, thereby releasing the segments 208, 210 and 206. Further details regarding the delivery of this device are described below.

For use in a patent foramen ovale, the segments 206, 208, 210 of the device 200 in one embodiment has an expanded diameter within the range of from about 1 cm to about 5 cm, and, in a further embodiment, about 2.5 cm. When the device 200 is longitudinally stretched, the overall length from the distal end 204 to the proximal end 202 is preferably within the range of about 4 cm to about 20 cm and, in one embodiment, about 8 cm. Preferably the wire 212 has a diameter of 0.001-0.03 in.

Although the device 200 is shown having a paperclip-like shape, it is envisioned that a number of variations of this shape can be utilized to provide the same results. For example, a bend may be provided in the device to aid in closure. For example, a bend may be placed in the intermediate segment 210, such that the device 200 is sized and configured to conform to the shape of the patent foramen ovale. Also, other non-circular or round shapes may be used for each segment, rather than the annular shape, as discussed above.

Figure 5:
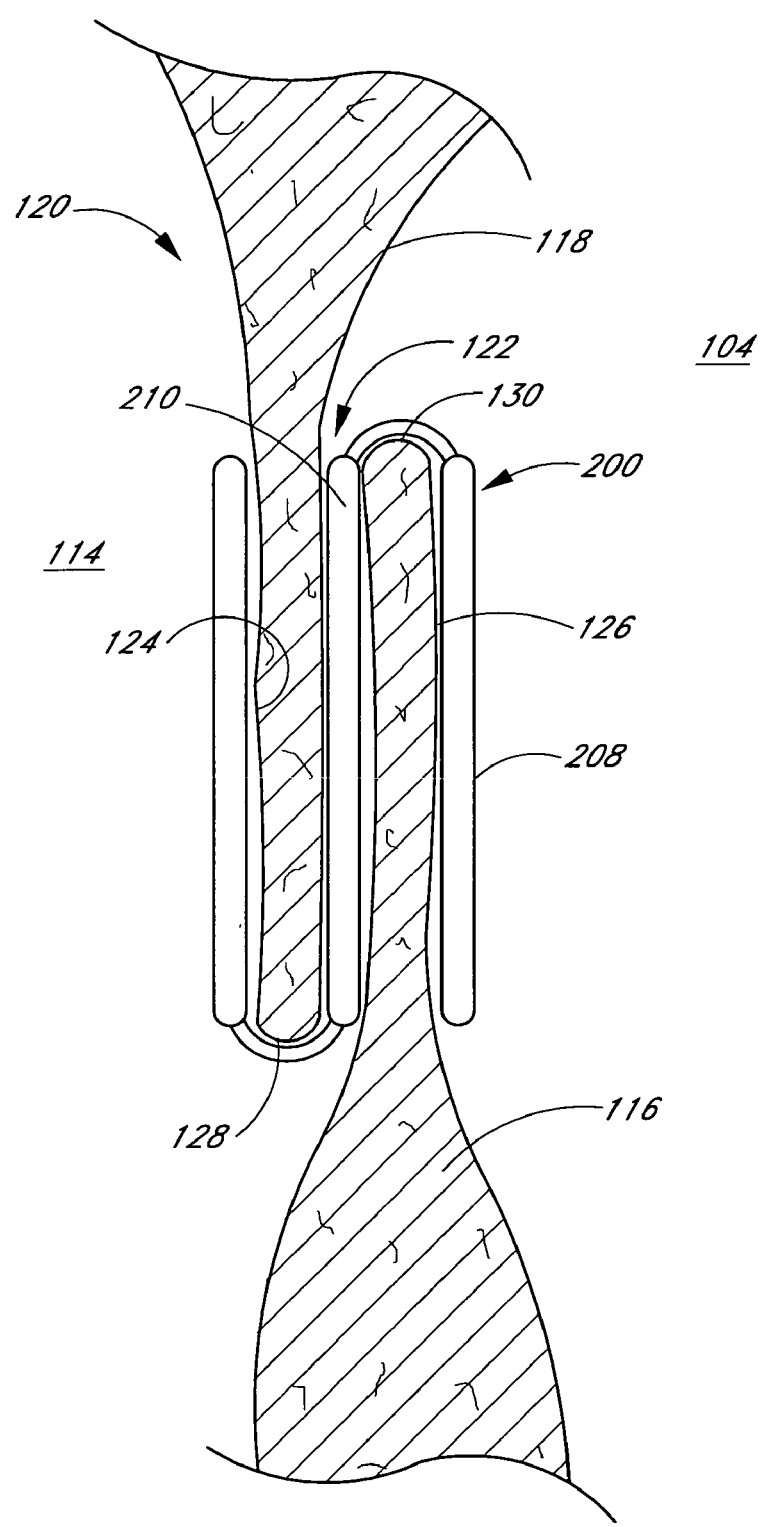
FIG. 5 is a cross-sectional view of a patent foramen ovale closed with the closure device of FIG. 2A, shown schematically.

FIG. 5 illustrates the closure device 200 implanted in a patent foramen ovale 120. The patent foramen ovale 120 includes a septum primum 116 having a surface 126 adjacent the left atrium 104, and a septum secundum 118 having a surface 124 adjacent the right atrium 114. A tunnel or channel 122 is located between the septum primum 116 and septum secundum 118. The closure device 200 may be delivered to the patent foramen ovale 120 using any suitable technique, such as described below. Once positioned, the distal segment 208 is positioned over the tip 130 of the septum primum 116 and lies along the surface 126 of the septum primum 116 adjacent the left atrium 104. The intermediate segment 210 lies between the septum primum 116 and septum secundum 118 in channel 122. The proximal segment 206 is positioned over the tip 128 of the septum secundum 118 and lies along the surface 124 of the septum secundum 118 adjacent the right atrium 114. After being delivered, the closure device 200 exerts a force on the septum primum 116 and septum secundum 118 to draw the two closer together, either through mechanical actuation or self-expansion of the device. In one embodiment, the proximal and distal segments are identical in shape, and may have identical shapes that form mirror images of each other across the patent foramen ovale to equally apply compressive force to both sides of the patent foramen ovale.

Figure 6:
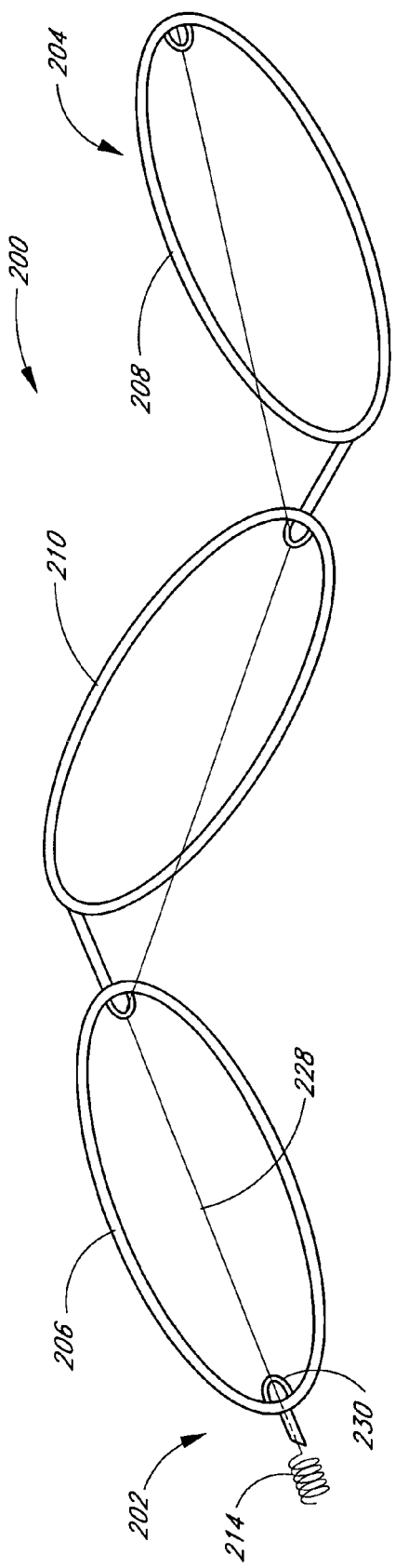
FIG. 6 is a perspective view of the closure device of FIG. 2A in a delivery state.
Figure 7:
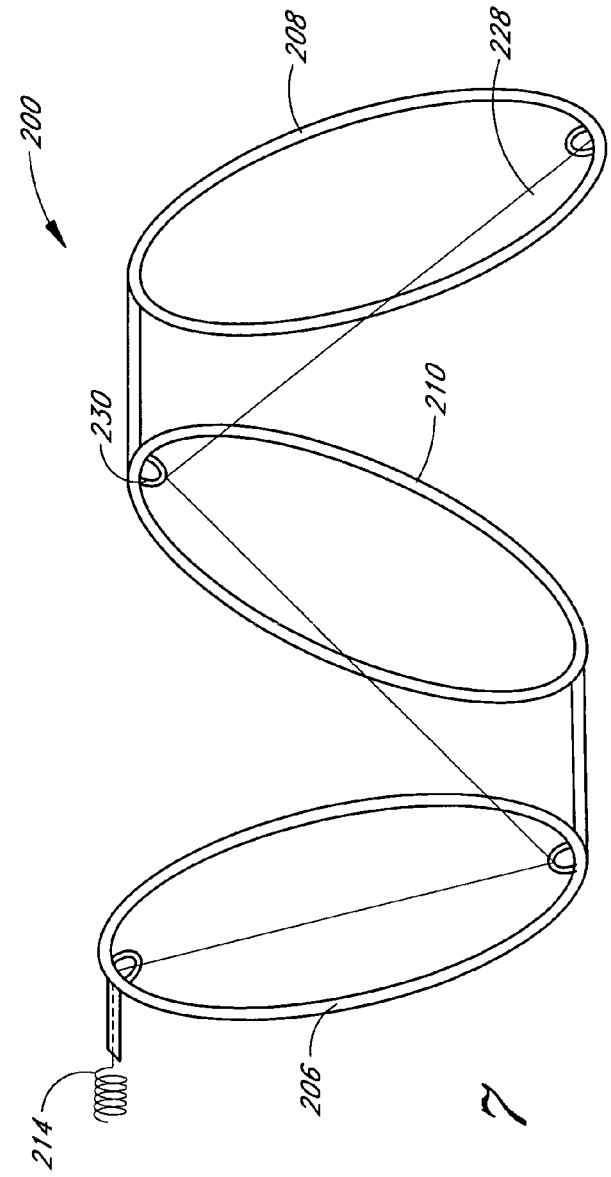
FIG. 7 is a perspective view of the closure device of FIG. 2A during a deployment state.

In one embodiment, the closure device 200 is designed to be implanted using a deployment catheter, such as described with respect to FIGS. 8-12 below. As shown in FIG. 6, the device 200 is designed to remain in a delivery or elongated state while in the catheter (not shown). In this delivery state, the device 200 can assume a generally elongate configuration wherein the proximal end 202 and distal end 204 are pulled apart from each other in a generally linear manner. Upon delivery to the patent foramen ovale, the device 200 is radially expanded (FIG. 7) into a clip or generally S-shaped configuration to occlude or close the patent foramen ovale. As illustrated, when expanded, the proximal and distal segments 202, 204 of the device are drawn relatively closer to the intermediate segment. In one embodiment, the device is preferably attached via detachment element 214 to a delivery device such as an actuator prior to deployment, and is then detached at detachment element 214 when properly positioned. In a further embodiment, the detachment element 214 may use a tether line in addition to or instead of a threaded fitting. Tether lines are described in detail in U.S. Pat. Nos. 6,214,029, 6,440,152, and 6,551,344, which are incorporated in their entirety herein. The procedure for placing the closure device and delivery device will be described in further detail hereinafter.

Figures 8, 9:
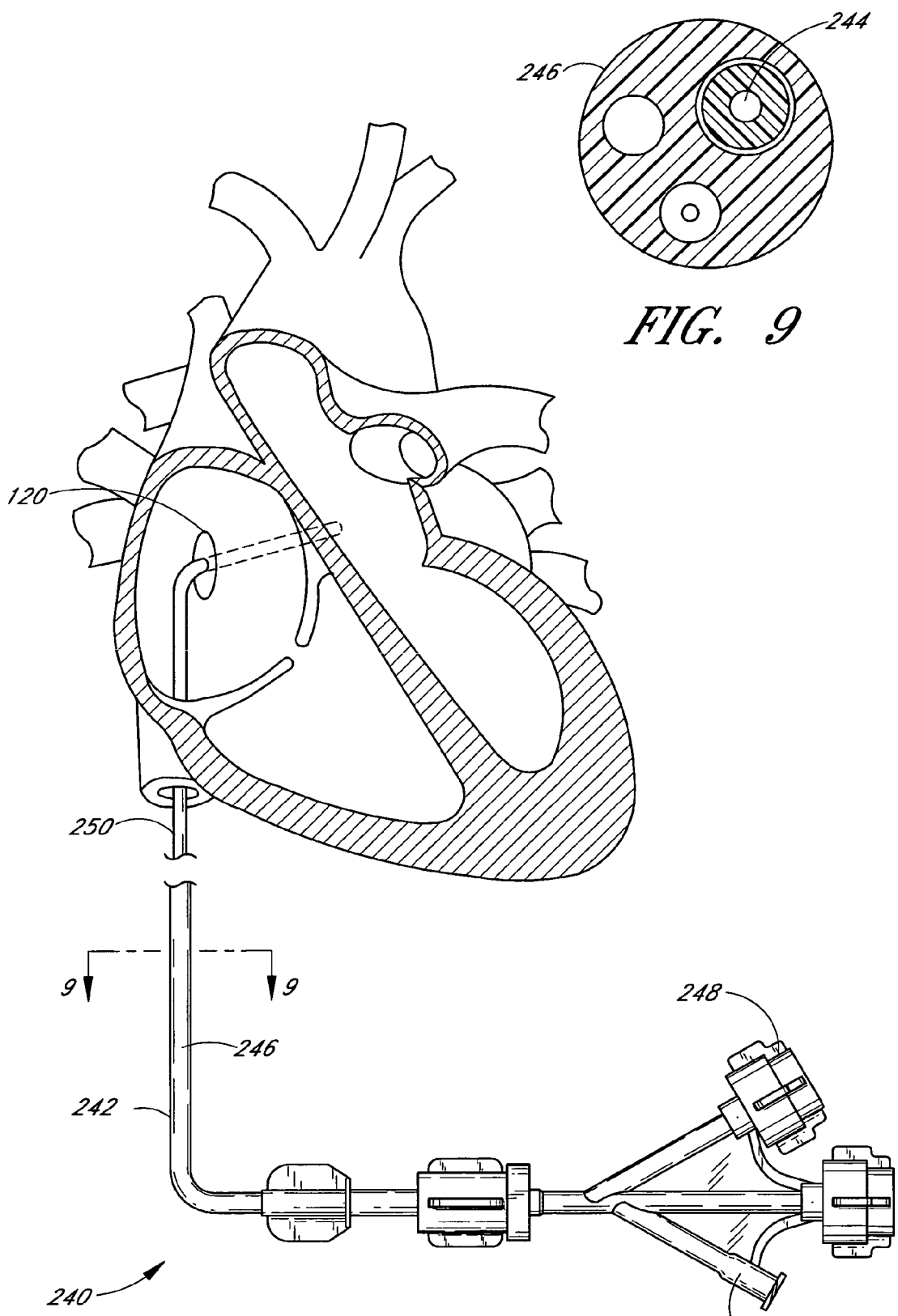
FIG. 8 is a schematic cross-sectional view through the heart with a transeptal catheter deployed at a patent foramen ovale.
FIG. 9 is a cross-sectional view of the catheter of FIG. 8 through line 9-9.

As shown in FIGS. 8-11, a closure device deployment system is provided for delivery of a closure device to a patent foramen ovale. Referring to FIG. 8, a closure device deployment system 240 comprises generally a catheter 242 for placing a detachable closure device 200 within a body cavity or lumen. The catheter 242 comprises an elongate flexible tubular body 246, extending between a proximal end 248 and a distal end 250. The catheter is shown in highly schematic form, for the purpose of illustrating the functional aspects thereof. The catheter body will have a sufficient length and diameter to permit percutaneous entry into the vascular system, and transluminal advancement through the vascular system to the desired deployment site. For example, in an embodiment intended for access at the femoral artery and deployment within the patent foramen ovale, the catheter 242 will have a length within the range of from about 50 cm to about 150 cm, and a diameter of generally no more than about 15 French. Further dimensions and physical characteristics of catheters for navigation to particular sites within the body are well understood in the art and will not be further described herein.

The flexible body can be manufactured in accordance with any of a variety of known techniques. In one embodiment, the flexible body 246 is extruded from any of a variety of materials such as HDPE, PEBAX, nylon, polyimide, and PEEK. Alternatively, at least a portion or all of the length of the tubular body may comprise a spring coil, solid walled hypodermic needle or other metal tubing, or braided reinforced wall, as are known in the art.

The tubular body 246 is further provided with a handle 252 generally on the proximal end 248 of the catheter 242. The handle 252 may be provided with a plurality of access ports. Generally, handle 252 is provided with an access port which may be used as a guidewire port in an over the wire embodiment, and a deployment wire or actuator port. Additional access ports such as a contrast media introduction port, or others may be provided as needed, depending upon the functional requirements of the catheter. The handle 252 permits manipulation of the various aspects of the closure device deployment system 240, as will be discussed below. Handle 252 may be manufactured in any of a variety of ways, typically by injection molding or otherwise forming a handpiece for single-hand operation, using materials and construction techniques well known in the medical device arts.

An actuator 244, as described below, is provided in accordance with one embodiment of the present invention, used to releasably engage and deploy the closure device 200. Any of a variety of structures such as solid cores, polymeric or metal single or multiple strand wires, ribbons, or tubes can be used. The actuator 244 may be retracted as with a pullwire design, or rotated as with a torque rod design, as will be discussed herein. The actuator 244 may be hollow or solid.

In use, the deployment catheter is percutaneously introduced into the vascular system and transluminally advanced into the heart and, subsequently, to the patent foramen ovale using techniques which are known in the art.

The patent foramen ovale may be accessed via catheter through a variety of pathways. It may be accessed from the arterial circuit. The catheter is introduced into the arterial vascular system, preferably in the femoral artery, and guided up the descending thoracic and/or abdominal aorta. The catheter may then be advanced into the left ventricle through the aortic outflow tract. Once in the left ventricle, the catheter may be directed up through the mitral valve and into the left atrium. When the catheter is in the left atrium, it may be directed into the patent foramen ovale and the closure device deployed.

Alternatively, the patent foramen ovale may be accessed from the venous circuit. The catheter may be introduced into the venous system, preferably in the femoral vein, advanced into the inferior vena cava or superior vena cava and guided into the right atrium. The catheter may then be directed to the patent foramen ovale. Alternatively, once in the right atrium, the catheter may be advanced through the tricuspid valve and into the right ventricle and directed to the ventricular septal defect and the closure device deployed.

Figure 10:
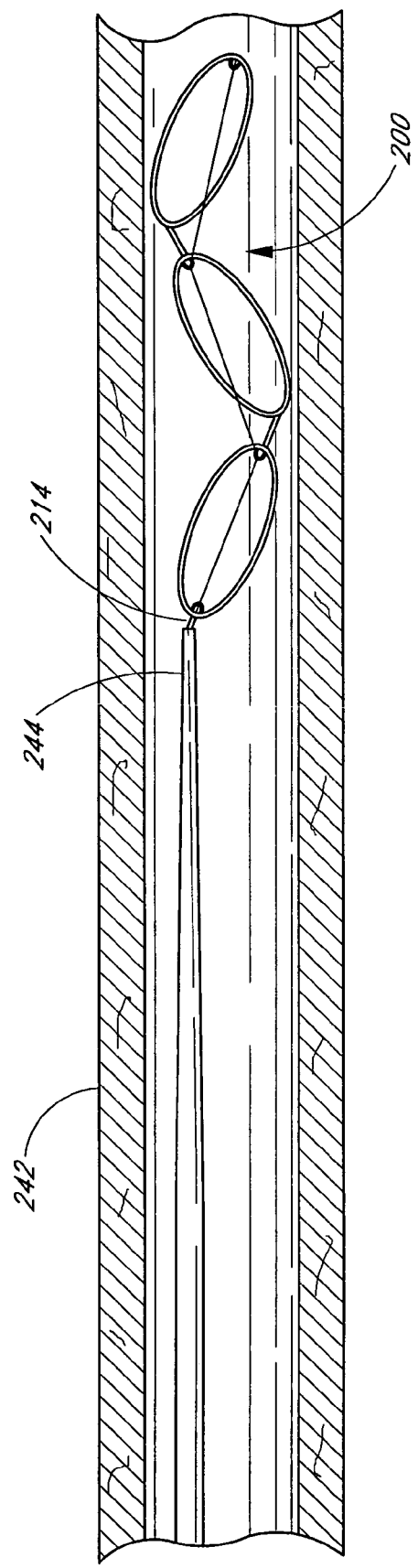

As shown in FIG. 10, in a preferred construction, a catheter 242 having a single lumen is illustrated. Also shown is an actuator 244 that acts as the actuator for deploying the device 200. In the illustrated embodiment, the actuator may be an elongate body such as a core wire that extends to the handle 252, and more preferably may be hollow to provide a passageway for the locking element 228 described with respect to FIG. 2B above. The actuator 244 may be removably attached to the proximal end 202 or other point of attachment on the closure device 200, such as through a threaded attachment at detachment element 214. Proximal retraction of the actutator 244 while resisting proximal motion of the closure device 200 or distally pulling on the closure device will cause elongating of the closure device 200 into its delivery state, as has been discussed. The closure device 200 is preferably loaded into the deployment catheter 242 as shown in FIG. 10. The actuator 244 may be locked or removably attached with respect to the closure device 200, and later severed or otherwise detached to enable removal of the deployment catheter 242 and proximal retraction of the actuator 244. In addition to a threaded connection, locking of the actuator 244 with respect to the closure device 200 may be accomplished in any of a variety of ways. For example, depending upon the desired catheter design, locking may be accomplished by using interference fit or friction fit structures, tether line, adhesives, a knot, or other technique known to one of ordinary skill in the art.

In the embodiment illustrated in FIG. 10, the actuator 244 is releasably connected to the proximal end of the closure device 200. This permits distal advancement of the closure device 200 through the catheter 242 by distal movement of the actuator 244. The proximal end of the actuator 244 may be connected to any of a variety of controls, including rotational knobs, levers and slider switches, depending upon the design preference. To deploy the device 200, the actuator is pushed distally until closure device 200 exits the catheter 242. Upon exiting the catheter, the locking element as described above may be actuated to cause the device to move to its deployed configuration. Alternatively, the device 200 may self-expand as it exits the catheter. After positioning of the device is confirmed, the actuator 244 is released from the device 200, and the actuator and deployment catheter are removed. Where a locking element is used, this locking element may be cut, released or otherwise secured to fix the position of the closure device. Further details on delivery methods are described below with respect to FIGS. 12A-12E.

When delivering a device such as in the embodiment of FIG. 2B, in another embodiment, a detachment element 214 may be provided that comprises a threaded attachment located on the distal segment 208. In this embodiment, the core wire 259 is inserted through the eyelets 230 of the closure device 200 and is distally threaded to connect with the detachment element, causing elongation of the device 200 into its delivery state. The closure device 200 is inserted into the deployment catheter 242 with the core wire inserted through the eyelets 230 of the device 200 and attached at the distal segment 208. The core wire may be advanced out of the deployment catheter to position the closure device in the patent foramen ovale, as discussed below. The core wire may then be detached from the distal segment 208 and retracted proximally to deploy the device 200. A hollow push rod positioned proximal to the closure device and over the core wire 259 may be used to assist in releasing the closure device from the core wire. Alternatively, the closure device may be positioned distally beyond the distal end of the deployment catheter 242, and interference between the deployment catheter 242 and the closure device 200 may be used to assist in releasing the closure device from the core wire. As discussed, the detachment element 214 may alternatively comprise a tether line, a threaded fitting, or other technique as is known to one of ordinary skill in the art to releasably secure the closure device 200 to the core wire 259. It will also be appreciated that in the embodiment of FIG. 2B, no detachment element may even be necessary other than the eyelets 230 that secure the closure device 200 to the core wire 259. As the core wire is retracted proximally from the eyelets 230 in the segments 206, 208, 210, the device 200 is released to its deployed shape, securing the septa 116, 118 of the patent foramen ovale, as described further below.

The actutator 244 or core wire 259 in one embodiment extends axially throughout the length of the catheter body 246, and is attached at its proximal end to a control on the handle 252. The actuator 244 or core wire 259 may comprise any of a variety of structures which has sufficient lateral flexibility to permit navigation of the vascular system, and sufficient axial column strength to be pushed through the catheter 242. Any of a variety of structures such as hypotube, solid core wire, "bottomed out" coil spring structures, or combinations thereof may be used, depending upon the desired performance of the finished device. In one embodiment, the core wire comprises stainless steel tubing.

As used herein, the term "core wire" is intended to include any of a wide variety of structures which are capable of transmitting axial tension or compression such as a pushing or pulling force with or without rotation from the proximal end 248 to the distal end 250 of the catheter 242. Thus, monofilament or multifilament metal or polymeric rods or wires, woven or braided structures may be utilized. Alternatively, tubular elements such as a concentric tube positioned within the outer tubular body 246 may also be used as will be apparent to those of skill in the art.

Figure 11A:
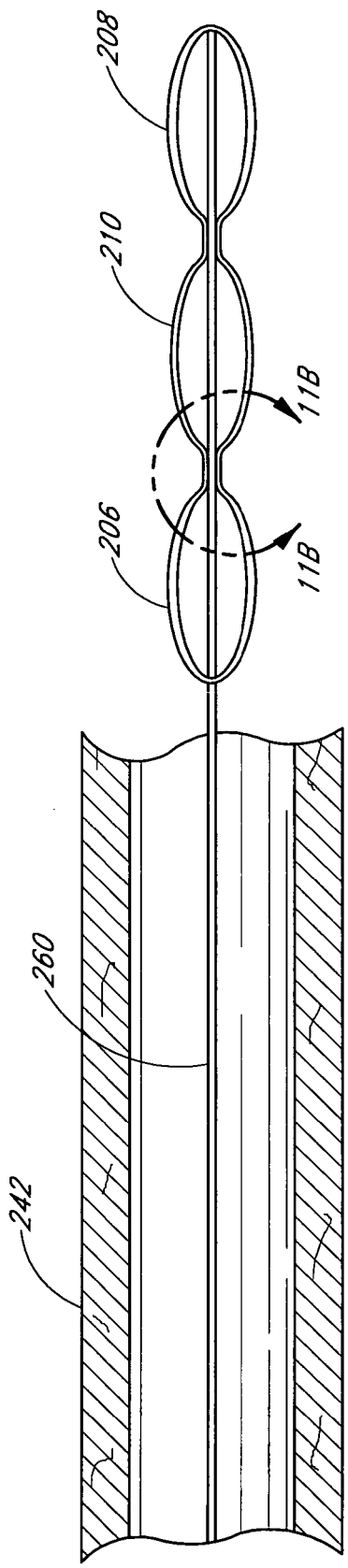
FIG. 11A is a partial cross-sectional view of an embodiment of the catheter of FIG. 8, with an embodiment of a closure device illustrated being delivered using a torque rod.
Figure 11B:
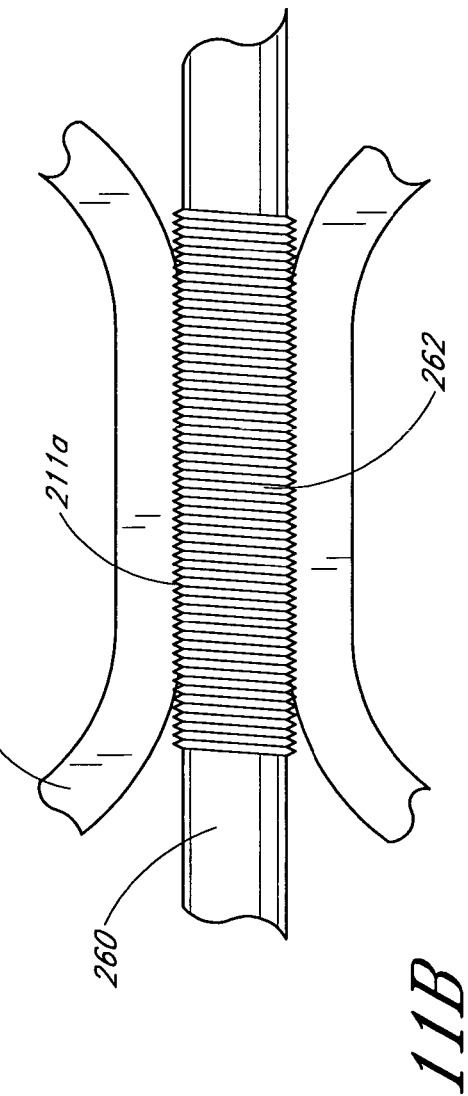
FIG. 11B is an enlarged view of a connecting portion of the closure device shown in FIG. 11A.
Figure 11C:
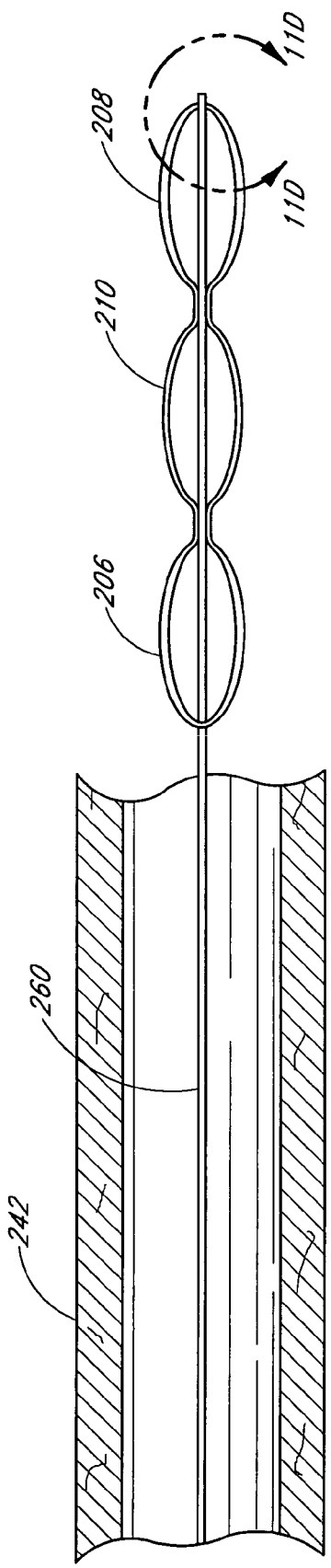

FIGS. 11A-11D illustrate an alternate construction wherein a closure device is biased toward its deployment configuration, such as being made from a shape memory material, and may be radially enlarged or reduced by rotating a torque element extending through the deployment catheter. Referring to FIGS. 11A and 11C, a rotatable torque rod 260 extends axially through the deployment catheter 242, and also extends through the closure device 200, preferably through at least one internally threaded portion provided in the closure device 200. For example, as shown in FIG. 11B, an externally threaded portion 262 of torque rod 260 may engage an internally threaded portion within connecting segment 211a. The rotatable torque rod may be encased in a plurality of tubes (not shown) within the closure device that are positioned approximately diametrically within any or all of segments 206, 208, and 210, said tubes preferably attached to the segments at each end of each tube. These tubes serve to guide the torque rod from the proximal end of the device through the connecting segments to the distal end. The proximal end of the torque rod 260 may be connected at a proximal manifold to a manual rotation device such as a hand crank, thumb wheel, rotatable knob or the like. Alternatively, the torque rod 260 may be connected to a power driven source of rotational energy such as a motor drive or air turbine.

The terms torque rod or torque element are intended to include any of a wide variety of structures which are capable of transmitting a rotational torque throughout the length of a catheter body. For example, solid core elements such as stainless steel, nitinol or other nickel titanium alloys, or polymeric materials may be utilized. In an embodiment intended for implantation over a guidewire, the torque rod 260 is preferably provided with an axially extending central guidewire lumen. This may be accomplished by constructing the torque rod 260 from a section of hypodermic needle tubing, having an inside diameter of from about 0.001 inches to about 0.005 inches or more greater than the outside diameter of the intended guidewire. Tubular torque rods 260 may also be fabricated or constructed utilizing any of a wide variety of polymeric constructions which include woven or braided reinforcing layers in the wall. Torque transmitting tubes and their methods of construction are well understood in the intracranial access and rotational atherectomy catheter arts, among others, and are not described in greater detail herein.

Figure 11D:
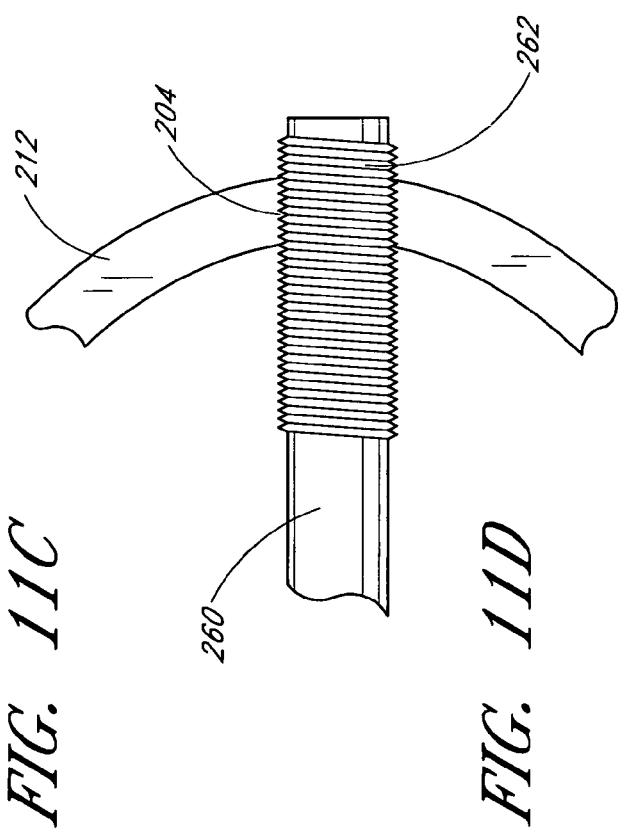
FIG. 11D is an enlarged view of a distal portion of the closure device shown in FIG. 11C.

One or more distal portions of the torque rod may be threaded as shown in FIGS. 11B and 11D. More particularly, threaded portions 262 may be provided on torque rod 260, to correspond to internally threaded portions of the distal segment 208 (FIG. 11D) or the connecting portions 211a and 211b (FIG. 11B). A distal threaded portion or distal rotating coupler, not shown, may be provided at the distal end 204 of the device to receive the distal end of the torque rod. As will be appreciated by those of skill in the art in view of the disclosure herein, in one embodiment, rotation of the torque rod 260 in a first direction relative to the closure device 200 will cause the torque rod 260 to advance distally. This distal advancement will stress the device and result in an axial elongation and radial reduction of the closure device 200 as the torque rod 260 is advanced distally into the threaded apertures of the closure device 200. Rotation of the torque rod 260 in a reverse direction will cause a proximal retraction of the torque rod 260, thus enabling a radial enlargement and axial shortening of the closure device 200.

In another embodiment, similar to that described with respect to FIG. 2B above where only the distal end 204 of the device 200 is threaded, the torque rod may be inserted through eyelets 230 formed at the proximal end 202 and connecting segments 211a and 211b of the device, thereby axially elongating the device 200, and threadingly engaging the distal end 204. Disengaging the torque rod 260 from the distal segment 208 will release the segment 208, permitting the segment 208 to collapse in its deployed position. The remaining segments 206, 210 may be released by proximally retracting the torque rod 260 from the eyelets 230 corresponding to each segment 206, 210.

With the torque rod 260 threadingly engaging the device 200, upon placement of the closure device 200 at the desired implantation site, the torque rod 260 is rotated in a direction that produces an axial proximal retraction. This allows radial enlargement of the radially outwardly biased closure device 200 at the implantation site. Continued rotation of the torque rod 260 will cause the threaded portion to exit proximally through the one or more threaded apertures provided on the closure device 200.

With the torque rod 260 extending through the deployment catheter 242, the device 200 may be provided beyond the distal end of the deployment catheter 242, so that when the torque rod is rotated to move the torque rod proximally, the distal force applied by the deployment catheter on the device 200 allows the device to release the torque rod. The deployment catheter 242 may also be provided with an antirotation lock (not shown) between a distal end of the catheter 242 and the closure device 200. In general, the rotational lock may be conveniently provided by cooperation between a first surface on the distal end of the deployment catheter 242, which engages a second surface on the closure device 200, to rotationally link the deployment catheter 242 and the closure device 200. Any of a variety of complementary surface structures may be provided, such as an axial extension on one of the first and second surfaces for coupling with a corresponding recess on the other of the first and second surfaces. Such extensions and recesses may be positioned laterally offset from the axis of the catheter. Alternatively, they may be provided on the longitudinal axis with any of a variety of axially releasable anti-rotational couplings having at least one flat such as a hexagonal or other multifaceted cross sectional configuration.

Any other means known may be used for temporarily attaching the closure device to a delivery system such as a deployment catheter or actuator. For example, any of a variety of interference fit such as threaded fit or snap fit, pin/loop combinations, interfering diameters, or heat dissociable solders or polymer bonds may be utilized.

The closure device deployment system 240 thus permits the closure device 200 to be maintained in a low crossing profile configuration, to enable transluminal navigation to a deployment site. Following positioning at or about the desired deployment site, distal advancement or proximal retraction of an actuator enables the closure device 200 to radially enlarge. Radial enlargement in one embodiment occurs under the device's own bias. Alternatively, certain embodiments of the closure device can be enlarged under positive force, such as by inflation of a balloon or by a mechanical mechanism as is discussed elsewhere herein. Once the clinician is satisfied with the position of the closure device 200, such as by injection of dye and visualization using conventional techniques, the actuator is proximally retracted thereby enabling detachment of the closure device 200 from the deployment system 240.

If, however, visualization reveals that the closure device 200 is not at the location desired by the clinician, the closure device 200 can be radially reduced and axially elongated, thereby enabling repositioning of the closure device 200 at the desired site. In the embodiment of FIG. 10, this repositioning is allowed by pulling the closure device 200 partially or wholly back into the catheter before release of the detachment element. In the embodiment of FIGS. 11A-D, the torque rod can be distally advanced to reengage the internal threading of the closure device. In some embodiments the torque rod will be guided within tubes attached to the segments (discussed previously). Thus, the closure device 200 can be enlarged or reduced by the clinician to permit repositioning and/or removal of the closure device 200 as may be desired.

Figure 12C:
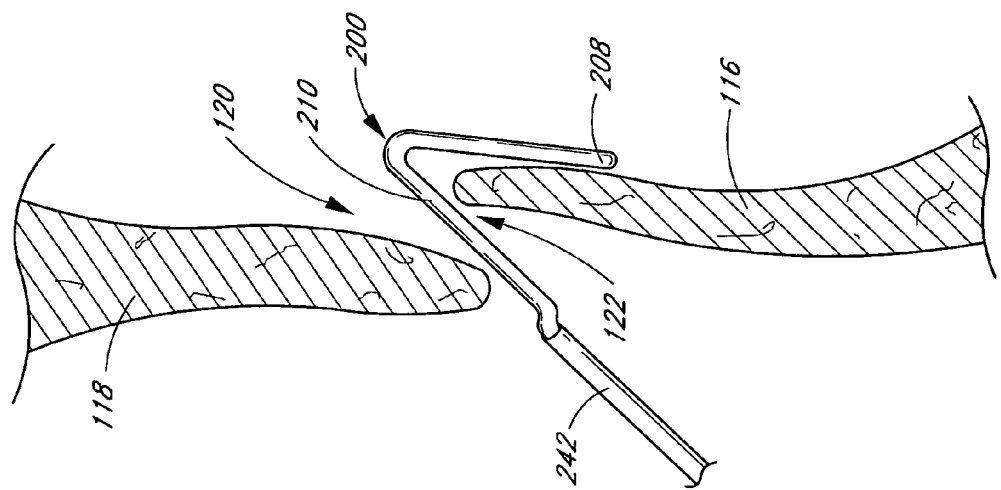
FIGS. 12A-E are schematic views of a patent foramen ovale closure procedure in accordance with one embodiment of the present invention.
Figure 12B:
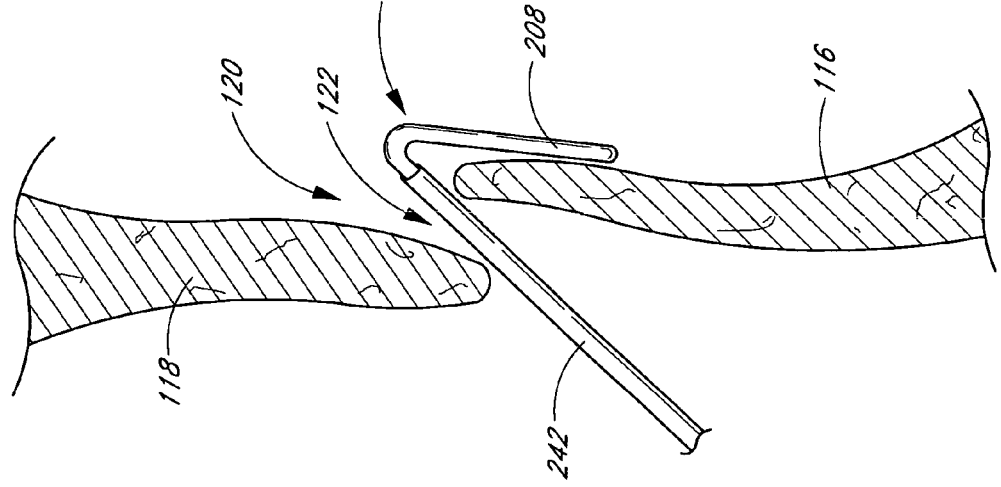
Figure 12A:
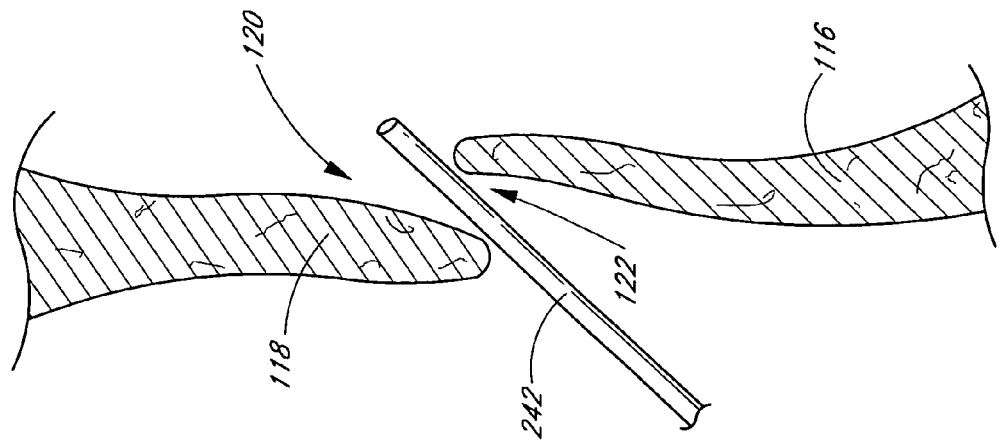
Figure 12D:
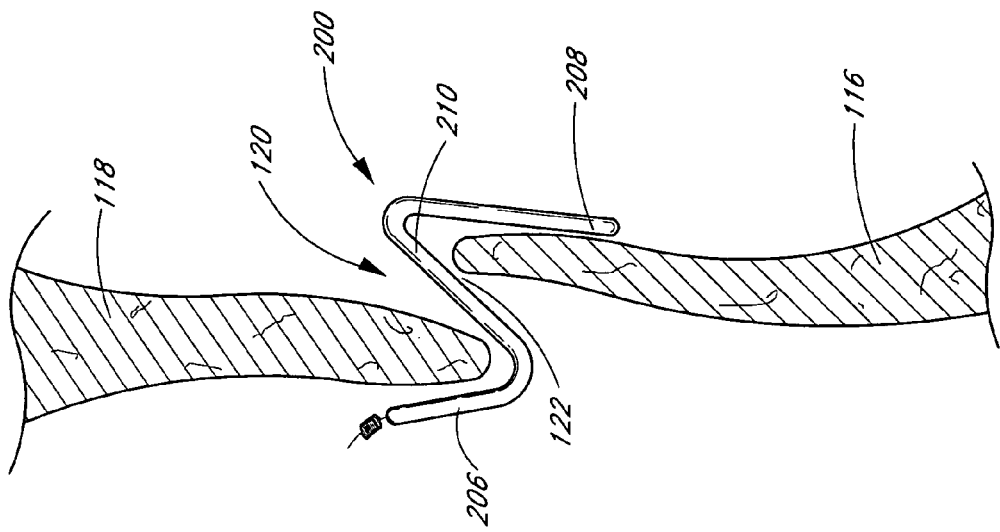

With reference to FIGS. 12A-12E, a closure device 200 (shown schematically) is preferably positioned within a patent foramen ovale. Initially, the device 200 is collapsed inside a deployment catheter 242. The catheter 242 is then positioned at or near the patent foramen ovale 120, as shown in FIG. 12A, more preferably through the channel 122 between the septum primum and septum secundum. Then, as shown in FIG. 12B, the distal segment 208 of the device is exposed and is pushed out, preferably using an actuator as described above, and deployed over the septum primum 116. The deployment catheter is retracted while releasing the intermediate segment 210 to be positioned inside the patent foramen ovale channel 122 (shown in FIG. 12C), along a surface of the septum primum and the septum secundum. Lastly, the proximal segment 206 is released from the deployment catheter and positioned against the septum secundum 118 (FIG. 12D). The positioning of each of the segments relative to the septum primum and septum secundum can occur due to a natural bias of the device as it exits the catheter, due to a mechanical actuation of the distal segment into this position, as described above, or due to a combination of natural bias and mechanical actuation. In another embodiment, a core may hold each segment 206, 208, 210 in a delivery or elongated state until proper positioning may be confirmed. The core may then be retracted, releasing the device 200 for deployment.

Figure 12E:
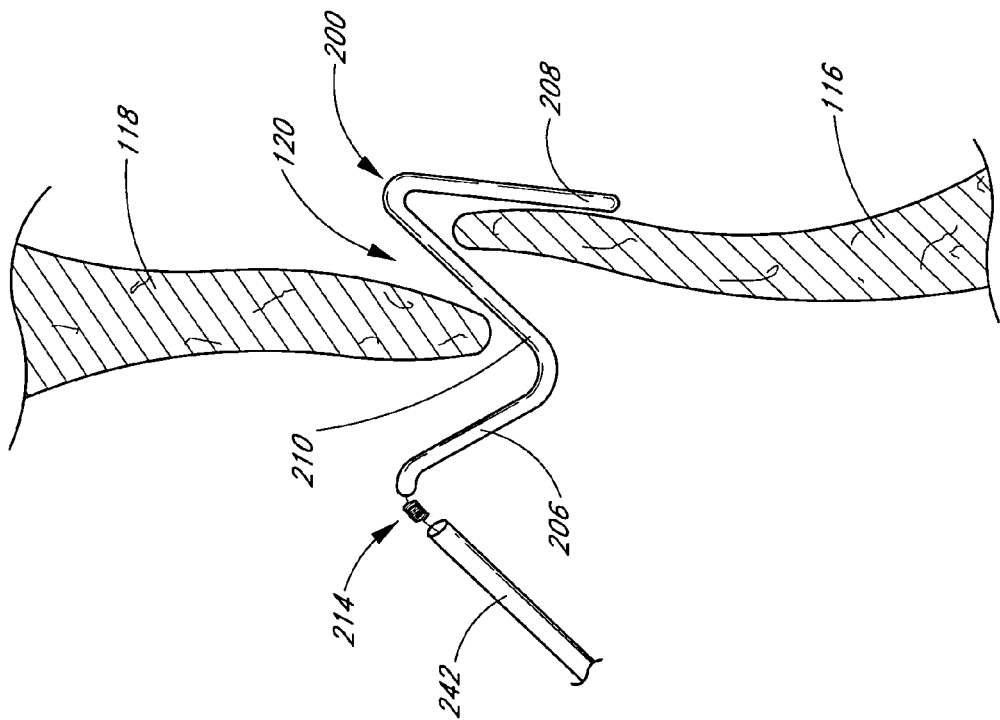

After optimal positioning and closure is achieved, the device 200 can then be detached from the delivery system, as shown in FIG. 12E. In one embodiment, detachment element 214 comprises a flexible segment such as a hinge or braid to allow the device 200 to assume a final implanted attitude without undue distortion applied to the implant or the septa from the deployment catheter. The device 200 can also be captured and retrieved at any time during the procedure as long as it is not fully detached from the delivery system. Once in position, the device clips the patent foramen ovale closed by exerting a force on the septum primum and septum secundum to draw the two together.

Figure 13:
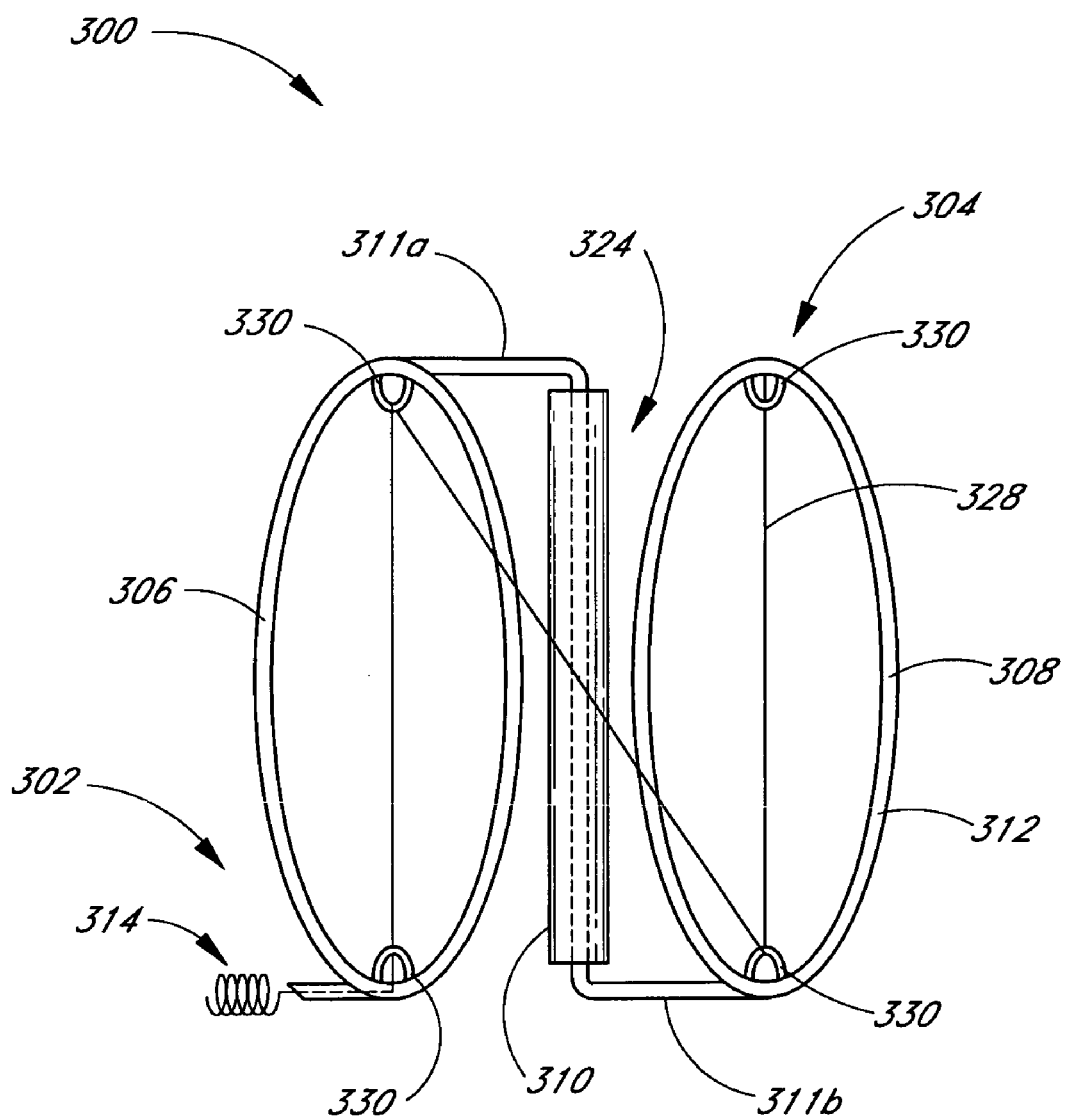
FIG. 13 is a perspective view of a closure device in accordance with another embodiment of the present invention.
Figure 14:
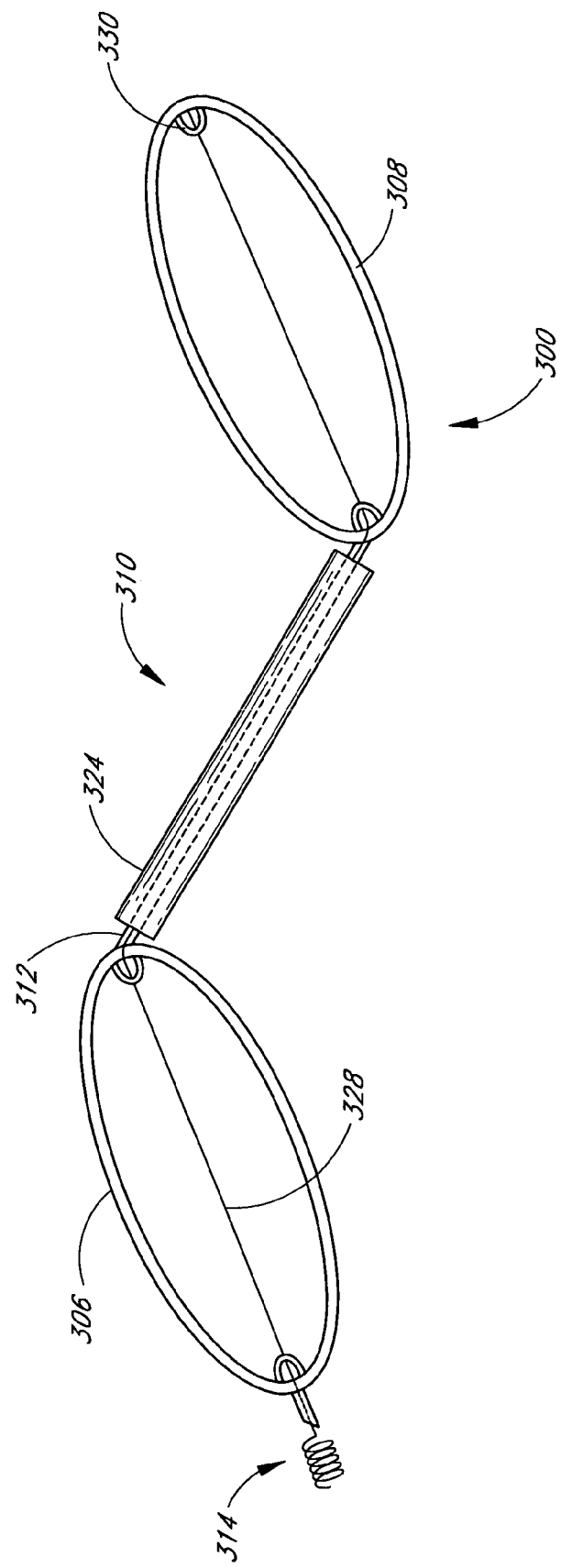
FIG. 14 is a perspective view of the closure device of FIG. 13 in a delivery state.

With reference to FIGS. 13-14, an alternative embodiment of a closure device in accordance with the present invention is shown. The closure device 300 preferably is shaped to form a clip-like device, similar to the closure device of FIG. 2A. The closure device has a proximal end 302 and a distal end 304. The closure device generally has three sections: a proximal segment 306, a distal segment 308, and an intermediate segment 310. In contrast to the device shown in FIG. 2A, in the closure device 300 shown in FIG. 13, the intermediate segment 310 is preferably a single straight wire preferably covered in a sleeve 324, rather than an elongated annular wire or loop. The intermediate segment 310 may also be cut from flat stock sheet Both the proximal and distal segments 306, 308 are generally annular in shape as described above. The segments 306, 308, 310 are formed from a wire 312 and are connected by connecting portions 311a and 311b, similar to the embodiment discussed above. The segments 306, 308, 310 form an integral structure for closing or occluding a patent foramen ovale. The closure device 300 is also preferably provided with a detachment element 314 on proximal end, as discussed above.

When delivered, the intermediate segment 310 is positioned in the channel between the septum primum 116 and the septum secundum 118 to close the patent foramen ovale 120, as was described in the embodiment above. The distal segment 308 is preferably positioned in the left atrium, while the proximal segment 306 is positioned in the right atrium. The closure device 300 is designed to be implanted using a delivery system, such as described above, and may have a collapsed or delivery state, as shown in FIG. 14.

Preferably, the wire 312 comprises a metal such as stainless steel, Nitinol, Elgiloy, or others which can be determined through routine experimentation by those of skill in the art. The wire may also be biodegradable. Wires having a circular or rectangular cross-section may be utilized depending upon the manufacturing technique. In one embodiment, a circular cross section wire is cut such as by known laser cutting techniques from tube stock. The closure device is preferably an integral structure, such as a single ribbon or wire, or element cut from a tube stock.

The intermediate segment 310 is preferably covered with a sleeve 324. The wire of the proximal and distal segments 306, 308 may also be covered with a sleeve. The sleeve 324 may comprise any of a variety of materials which facilitate cellular in-growth, such as ePTFE. The suitability of alternate materials for sleeve 324 can be determined through routine experimentation by those of skill in the art. In one embodiment, the sleeve 324 comprises two layers. The two layers may be bonded to each other around the wire 312 in any of a variety of ways, such as by heat bonding with or without an intermediate bonding layer such as polyethylene or FEP, adhesives, sutures, and other techniques which will be apparent to those of skill in the art in view of the disclosure herein. The sleeve 324 in one embodiment preferably is securely attached to the device 300 and retains a sufficient porosity to facilitate cellular ingrowth and/or attachment. In one embodiment, the segments 324, 310 may be configured to occlude the channel 122 in addition to the closure of the patent foramen ovale induced by the proximal and distal segments 306, 308.

Preferably, the device 300 includes a locking element 328 and retention elements 330 for retaining the locking element 328 to the closure device 300, as described above. The locking element 328 is used to longitudinally collapse the device and hold it in place at the patent foramen ovale. The locking element 328 preferably comprises a locking string which is preferably used to both expand and lock the device at the patent foramen ovale 120.

For use in a patent foramen ovale, the closure device 300 has an expanded diameter within the range of from about 1 cm to about 5 cm, and, in one embodiment, about 2.5 cm. The overall length of the closure device 300 from the distal end 308 to the proximal end 306 is preferably within the range of from about 4 cm to about 20 cm and, in one embodiment, about 8 cm. Preferably the wire has a diameter of 0.001-0.03 in.

Single Clip or Hook Embodiment

Figure 15:
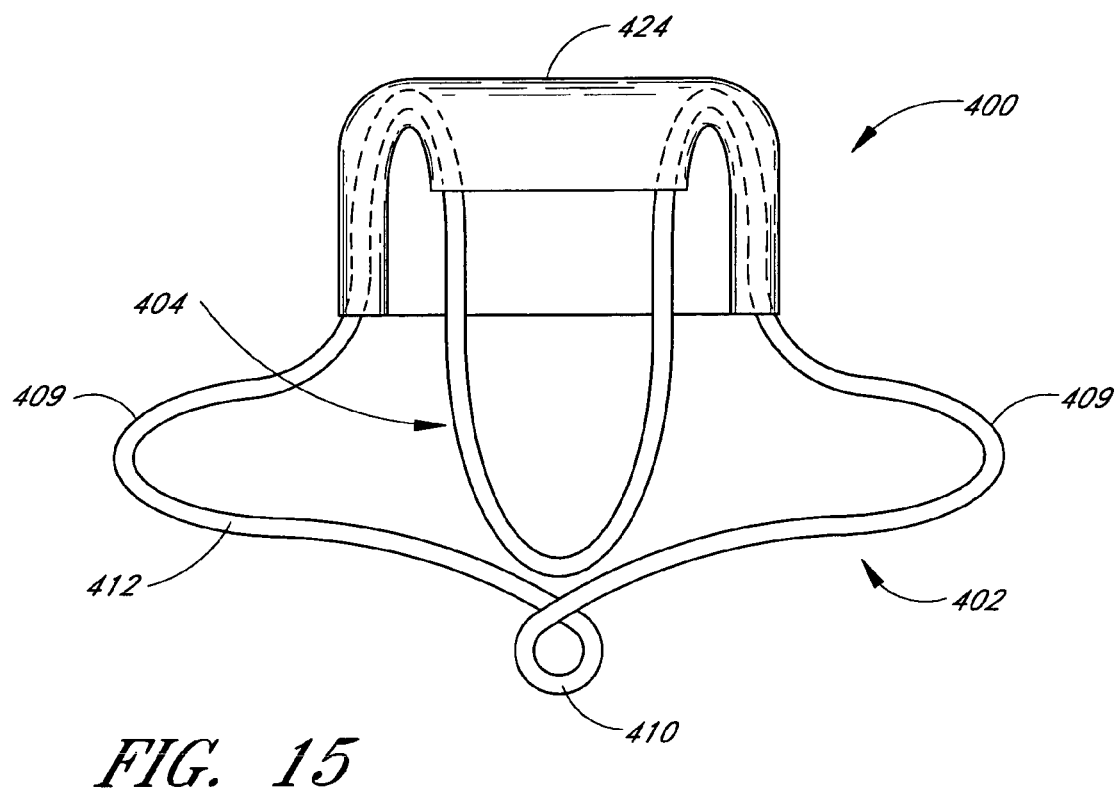
FIG. 15 is a back elevational view of a closure device in accordance with another embodiment of the present invention.
Figure 16:
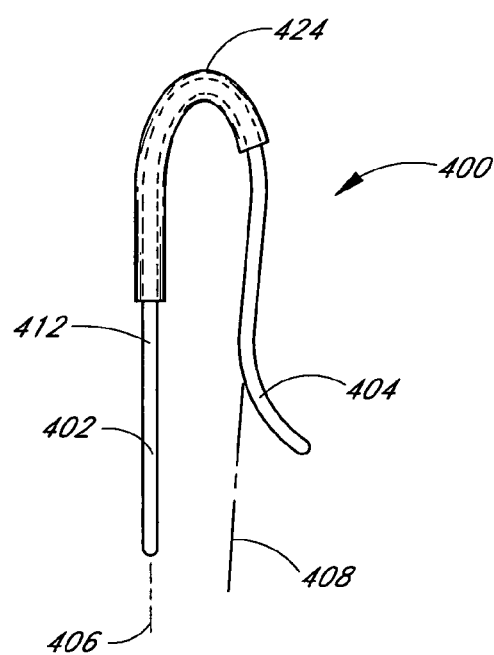
FIG. 16 is a side view of the closure device of FIG. 15.
Figure 17:
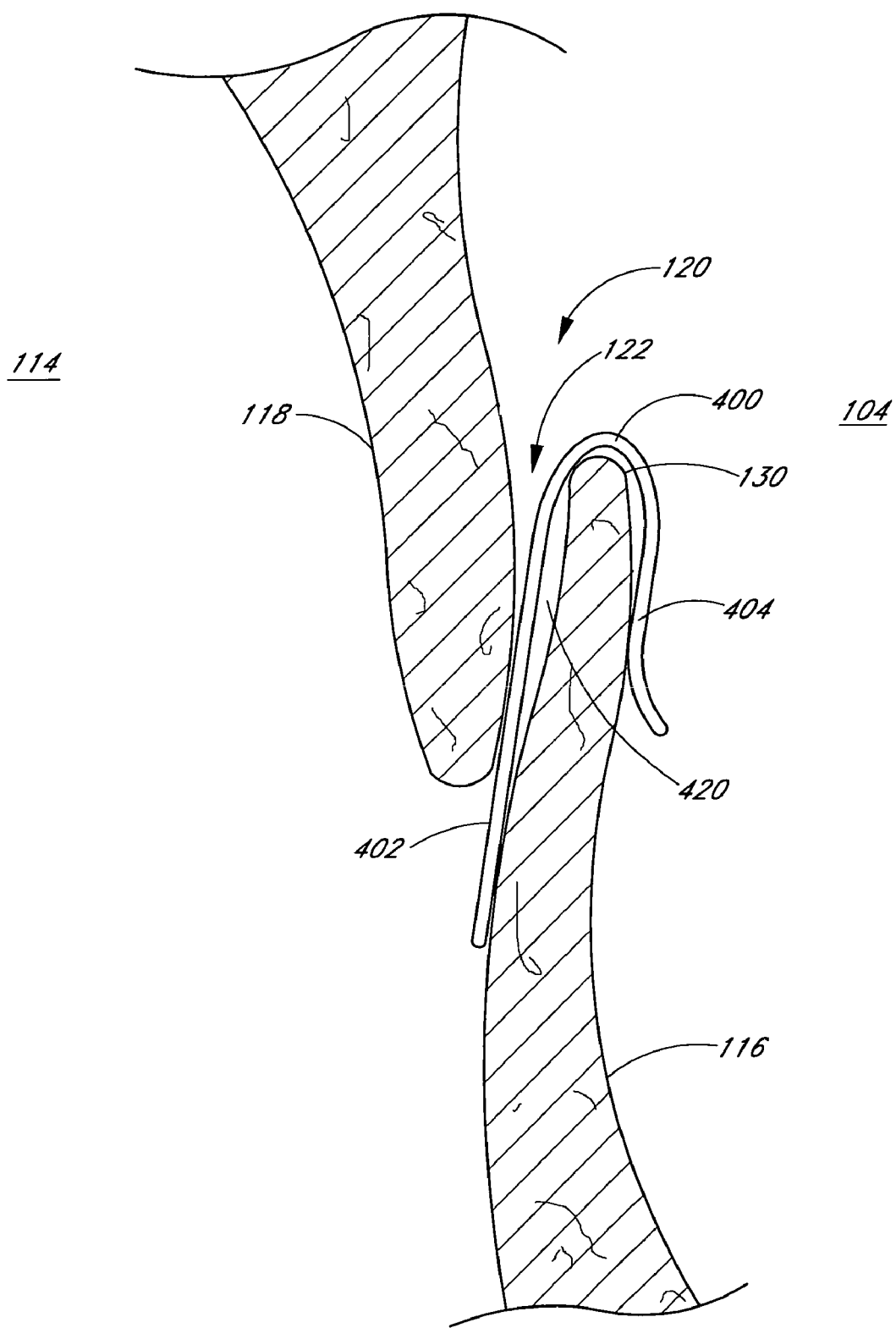
FIG. 17 is a cross-sectional view of a patent foramen ovale closed with the closure device of FIG. 15.

With reference to FIGS. 15-17, there is illustrated an additional embodiment of a closure device 400. The device comprises a proximal or an anterior section 402 and a distal or posterior section 404. A first axis 406 passing through the anterior section 402, and a second axis 408 passing through the posterior section 404, generally parallel to one another, are shown. The anterior section 402 comprises wings 409, which are used to anchor the device into the correct atrium, preferably the right atrium. The wings 409 preferably extend to beyond the edges of the patent foramen ovale to provide additional support to device 400. The anterior and posterior sections 402, 404 are integral and form a structure which hooks over the tip 130 of the septum primum 116. The device is provided with a loop 410 integral with the structure to attach the device 400 to the delivery device. The anterior section 402, posterior section 404, and loop 410 are an integral structure and are formed of a single wire 412. The device is preferably shaped like a hook, as can be seen with reference to FIG. 16, and is preferably self-expanding into the hook shape.

The anterior section 402 and posterior section 404 are positioned between the septum primum 116 and the septum secundum 118 and hook over the septum primum 116 to close a patent foramen ovale 120, as shown in FIG. 17. This embodiment stabilizes the flap of the patent foramen ovale 120. The posterior section 404 is positioned in the left atrium, while the anterior section 402 is positioned in the patent foramen ovale and extends out into the right atrium. The anterior section 402 is preferably of such a length as to extend along the septum primum 116 to prevent the septum primum 116 from displacing into the left atrium 104. The posterior section 404 prevents the tip 130 of the septum primum 116 from displacing into the left atrium 104 while the anterior section 402 secures the device 400 to the septum primum 116. The anterior section 402 is preferably sized and configured to extend along the right atrium 114 side of the septum primum 116 such that the base of the septum primum 116 provides support to the device 400, which prevents displacement of the septum primum tip 130 into the left atrium 104.

Preferably, the wire 412 comprises a metal such as stainless steel, Nitinol, Elgiloy, or others which can be determined through routine experimentation by those of skill in the art. The wire may also be biodegradable. Wires having a circular or rectangular cross-section may be utilized depending upon the manufacturing technique. In one embodiment, a circular cross section wire is cut such as by known laser cutting techniques from tube stock. The closure device is preferably an integral structure, such as a single ribbon or wire, or element cut from a tube stock.

A portion of the device 400 is preferably covered with a sleeve 424 as shown in FIG. 16. The sleeve 424 bridges the fossa and patent foramen ovale 120, while the wire structure stabilizes the flap of the patent foramen ovale 120. The sleeve 424 may comprise any of a variety of materials which facilitate cellular in-growth, such as ePTFE. The suitability of alternate materials for sleeve 424 can be determined through routine experimentation by those of skill in the art. In one embodiment, the sleeve 424 comprises two layers. The two layers may be bonded to each other around the wire 412 in any of a variety of ways, such as by heat bonding with or without an intermediate bonding layer such as polyethylene or FEP, adhesives, sutures, and other techniques which will be apparent to those of skill in the art in view of the disclosure herein. The sleeve 424 in one embodiment preferably is securely attached to the device 400 and retains a sufficient porosity to facilitate cellular ingrowth and/or attachment.

Figure 18C:
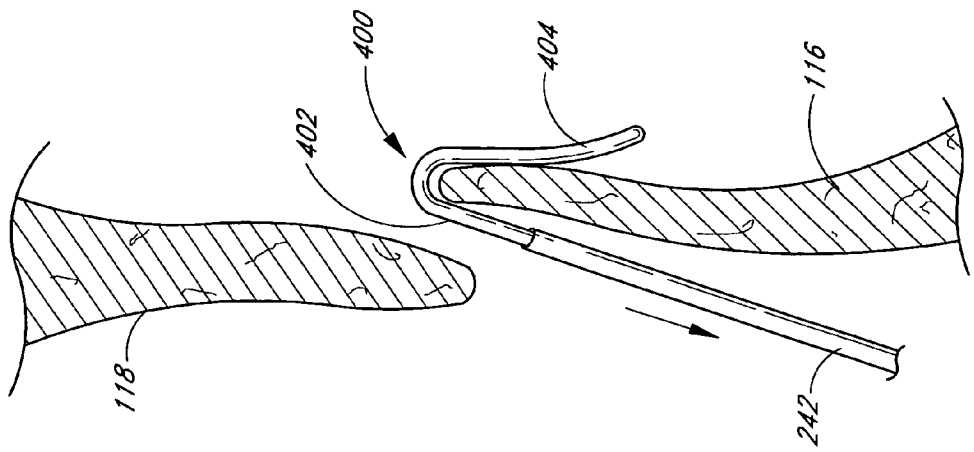
FIGS. 18A-E are schematic views of a patent foramen ovale closure procedure in accordance with one embodiment of the present invention.
Figure 18B:
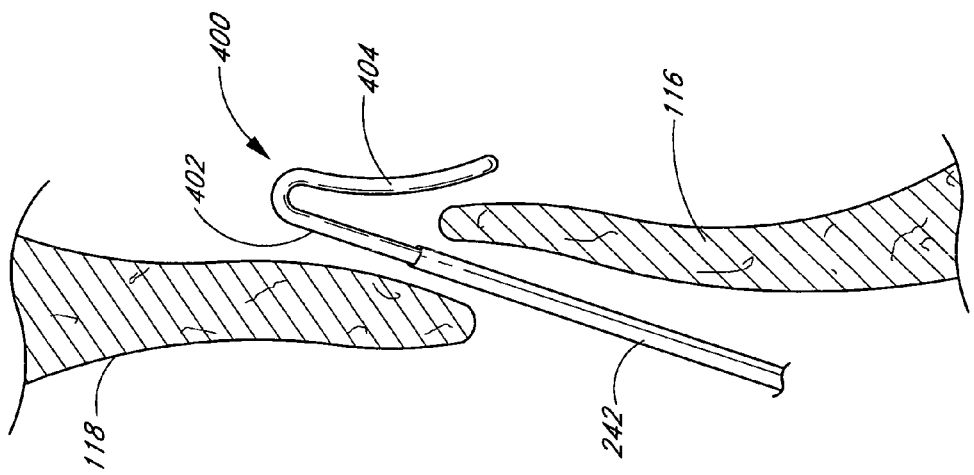
Figure 18A:
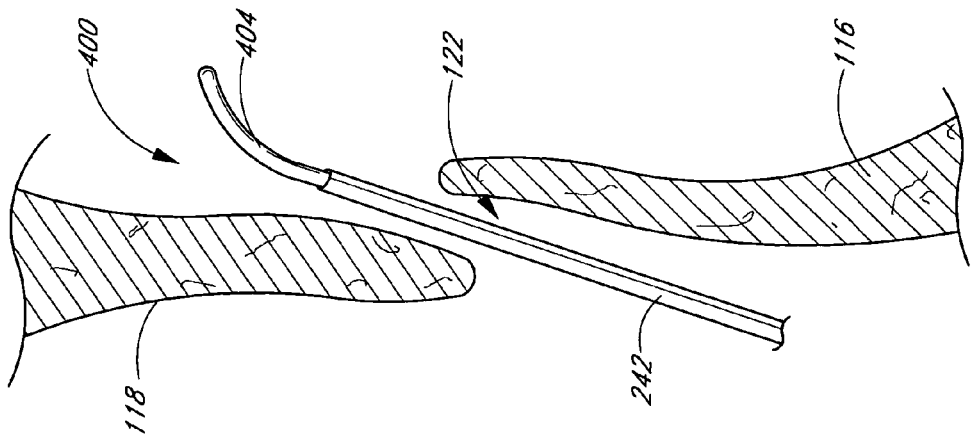

Referring to FIGS. 18A-E, a closure device 400 such as described above is preferably positioned within a patent foramen ovale to be closed or occluded. In a patent foramen ovale application, the distal end of a deployment catheter 242 is positioned at or near the patent foramen ovale 120, as shown in FIG. 18A. The position may be confirmed using fluoroscopy, echocardiography, or other imaging. The device 400 is initially in a collapsed state within catheter 242, such as described above. The left atrium segment 404 of the device 400 is exposed and positioned on the septum primum 116 by advancing or rotating actuator 244 (not shown), as discussed herein. See FIG. 18B. The anterior segment 402 is then positioned inside the patent foramen ovale channel 122 and on the septum secundum 118 again by advancing or rotating actuator 244 (not shown) (FIG. 18C). One of ordinary skill in the art will recognize that actuation of the device 400 may be accomplished as mentioned above. For example, actuation of the device 400 may be mechanically induced, self-expanding, a combination of mechanical and self-expanding. Additionally, deployment and detachment of the device may be accomplished as discussed above. For example, the device may be deployed via a tether line or torque rod, and detached accordingly as discussed previously. In one embodiment, a tether line, core wire or other actuator 244 may be attached to loop 410 for releasably deploying the device.

Figure 18E:
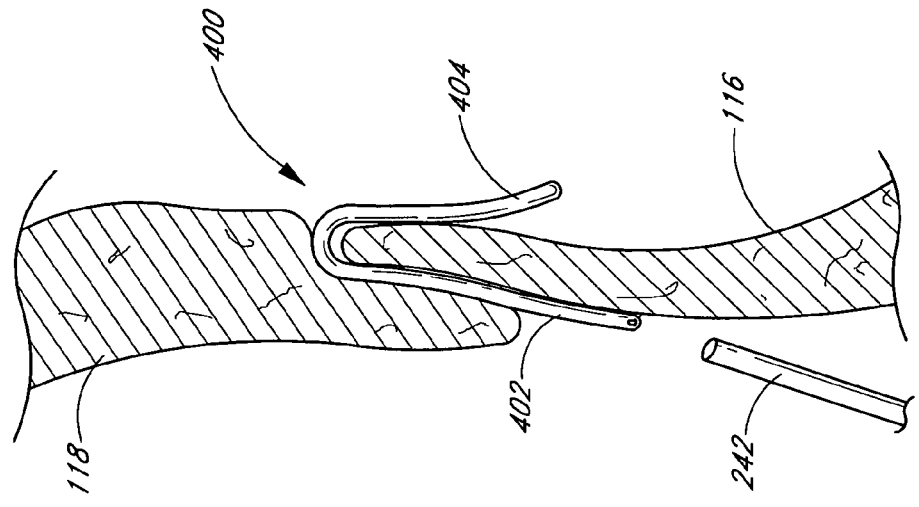
Figure 18D:
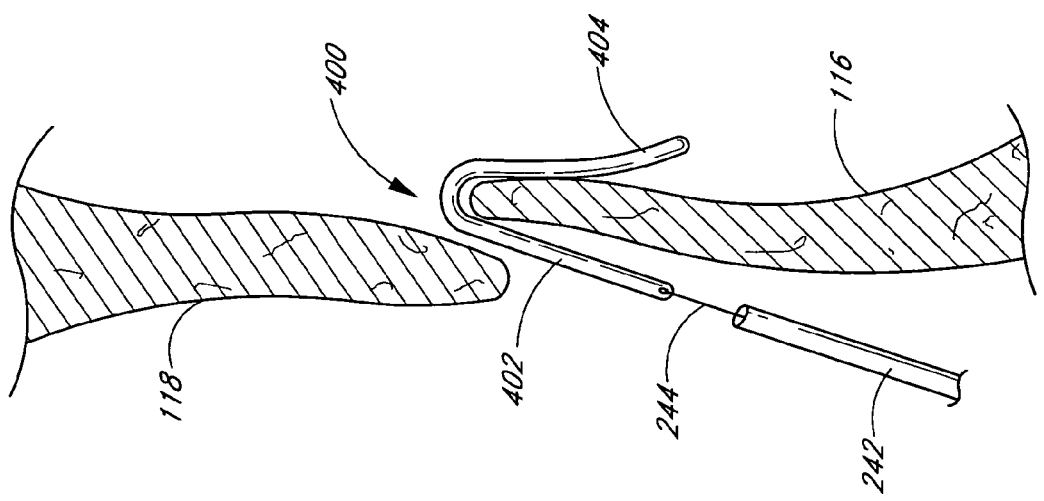

After optimal positioning and sealing is achieved, as shown in FIG. 18D, the device 400 can then be detached from the delivery system, as shown in FIG. 18E. The device 400 can also be captured and retrieved at any time during the procedure as long as it is not detached from the actuator 244.

Other Clip Embodiments

Referring to FIGS. 19-20, there is illustrated another preferred embodiment of the present invention. The closure device 440 comprises a proximal or an anterior section 442, a distal or posterior section 444 and an intermediate section 446. The posterior section 444 comprises two legs 449 that extend generally parallel to a longitudinal axis of the device which form an exaggerated "T" shape with the intermediate section 446. The anterior section 442 has a generally rectangular shape. Sections 442, 444, and 446 may be self-expanding and form an integral structure 452, or may be separately joined such as by a hinged connection. In some embodiments, anchors 447 may be provided to secure the implant against the septum primum 116 and septum secundum 118. As illustrated, the anchors may be punched in the anterior and intermediate section 442 and 446 and heat set or deformed to extend proud of device 440 surface. Hole 448 may be provided in proximal end of anterior section 442 to facilitate attachment of a tether and the like to closure device 440.

The anterior section 442 is configured and positioned in the right atrium, the posterior section 444 is configured to be positioned in the left atrium, and the intermediate section 446 is configured to be positioned between the septum primum 116 and the septum secundum 118. The posterior section 444 hooks over the septum primum 116 and the anterior section 442 hooks over the septum secundum 118 to occlude or close a patent foramen ovale 120, as shown in FIG. 20. The septum primum 116 and septum secundum 118 are held together by the clamping force exerted by the clips defined between sections 444 and 446, and sections 442 and 446. The design minimizes the amount of material exposed to blood flow in the left and right atria, thereby reducing the chance of clot formation. The shape is designed to fit the anatomy without distending tissue, thereby reducing the chance of leaks and promoting health.

In some embodiments, the clip structure can be made by laser cutting flat stock sheet. Preferably, the clip structure comprises a metal such as stainless steel, Nitinol, Elgiloy, or others which can be determined through routine experimentation by those of skill in the art.

Figure 21A:
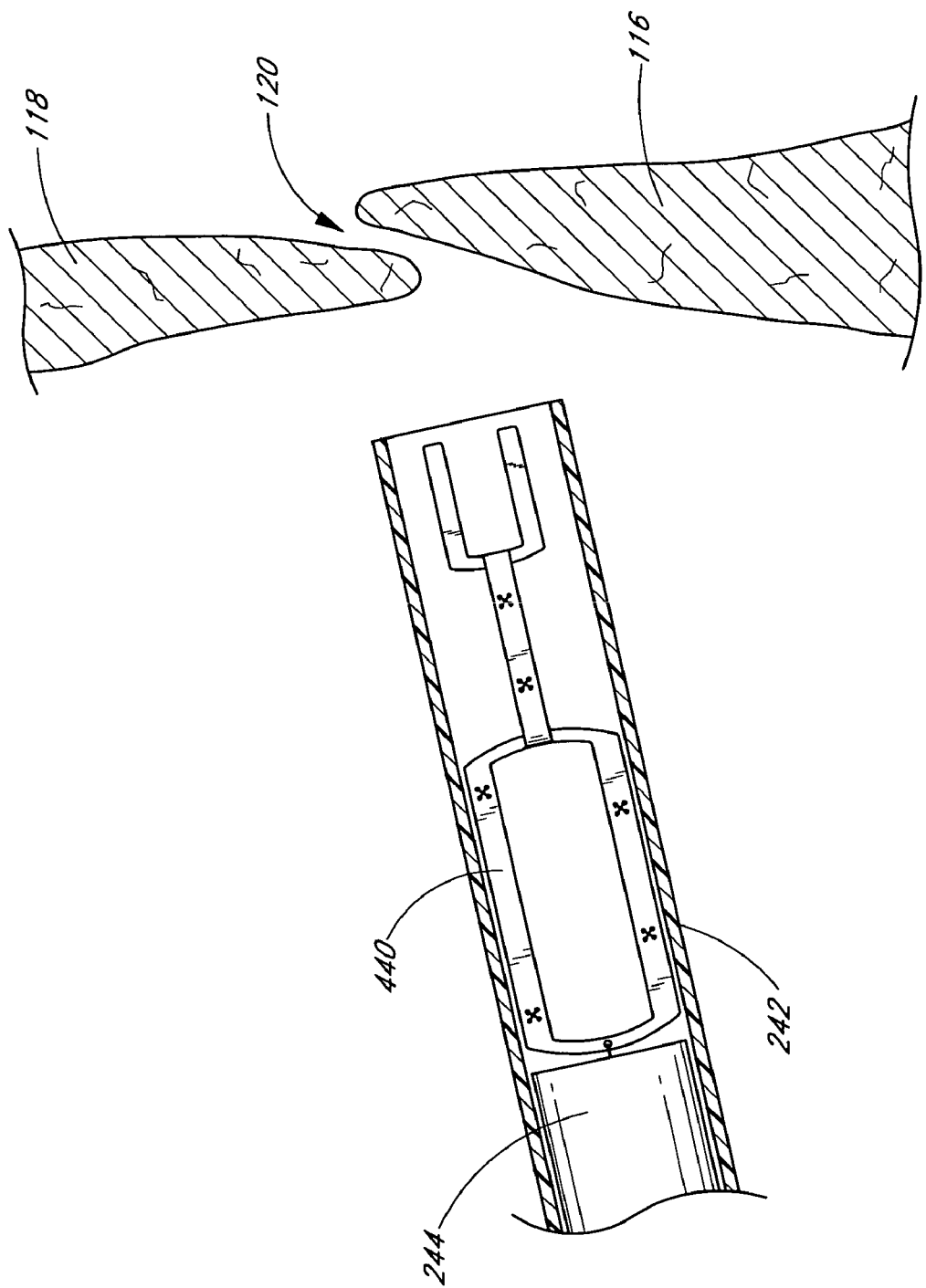
FIGS. 21A-D are schematic views of a patent foramen ovale closure procedure in accordance with another embodiment of the present invention.
Figure 21B:
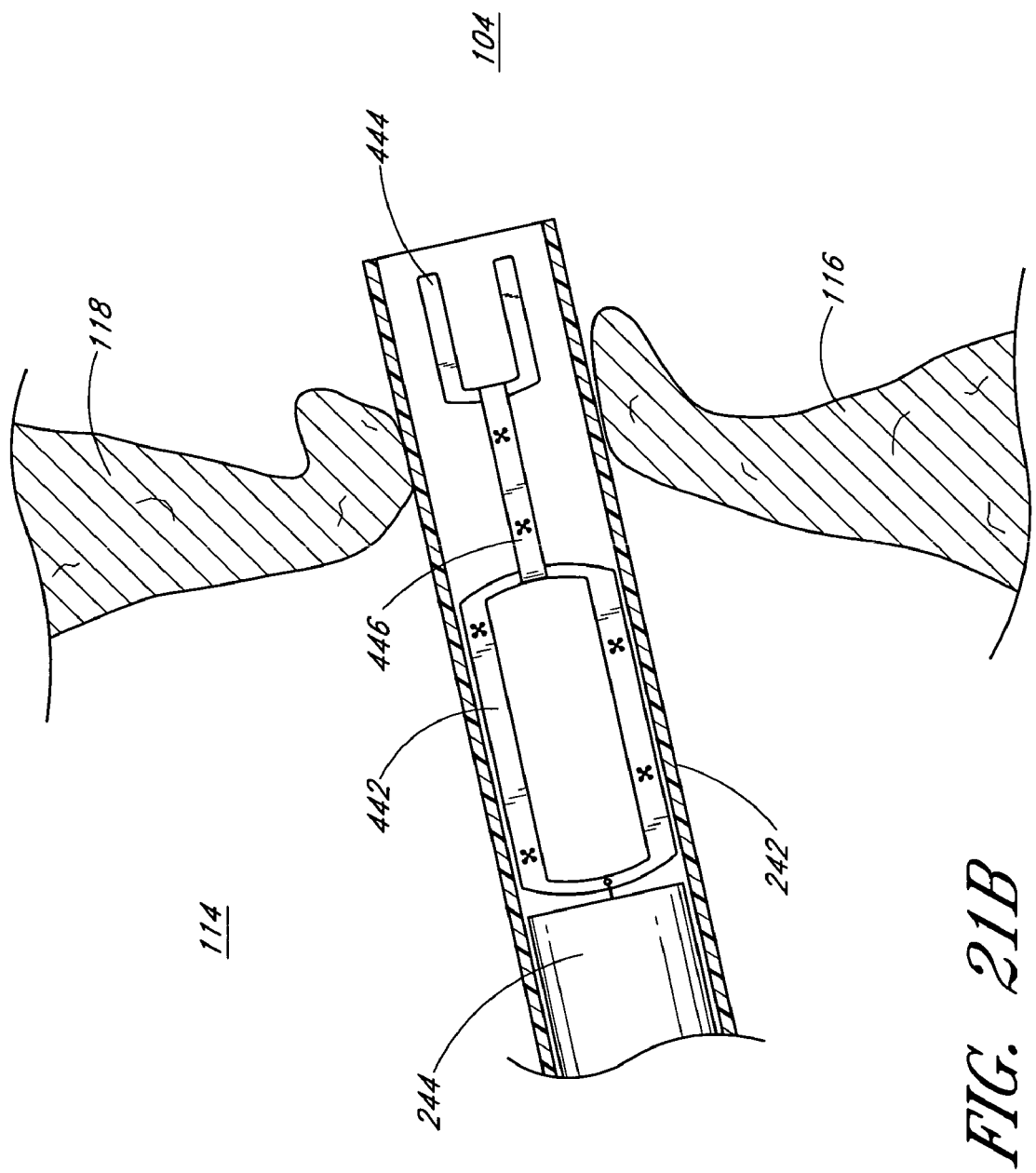
Figure 21C:
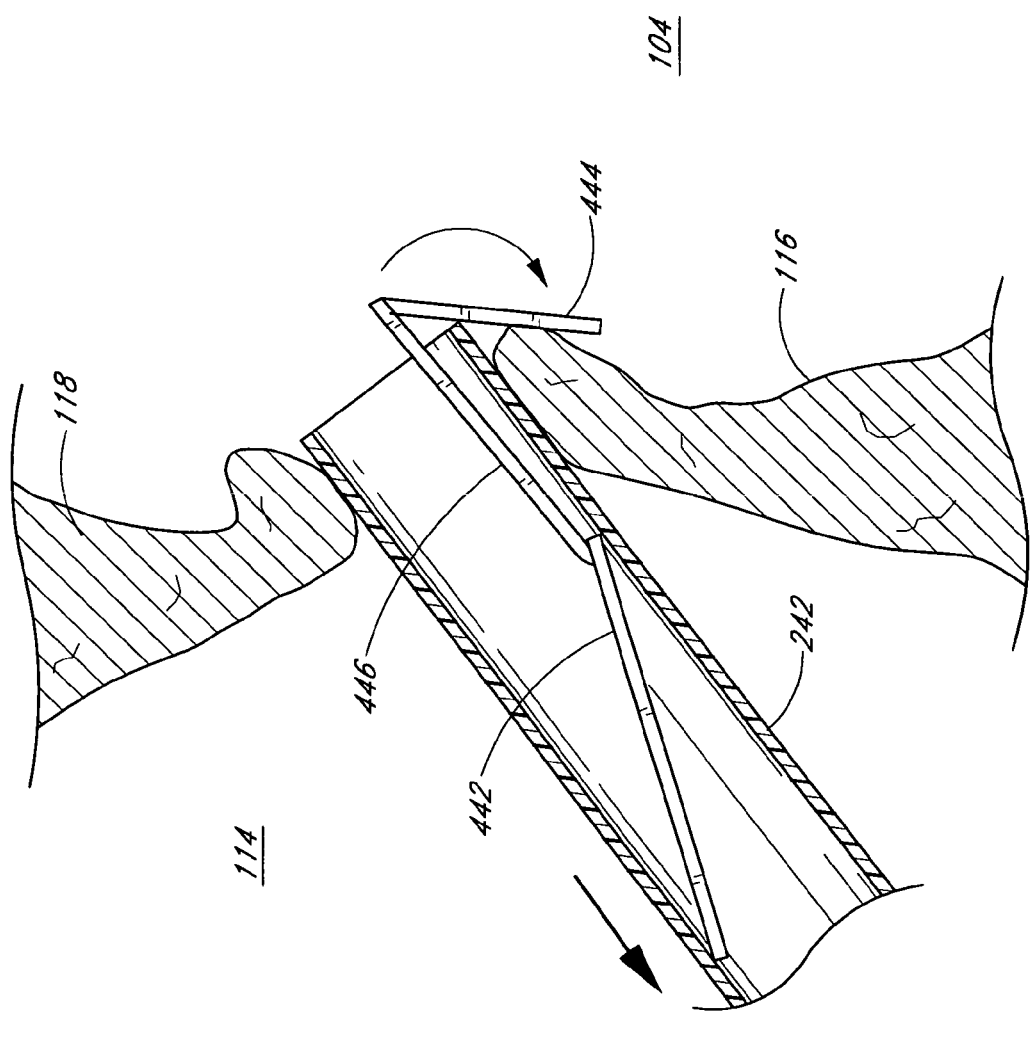
Figure 21D:
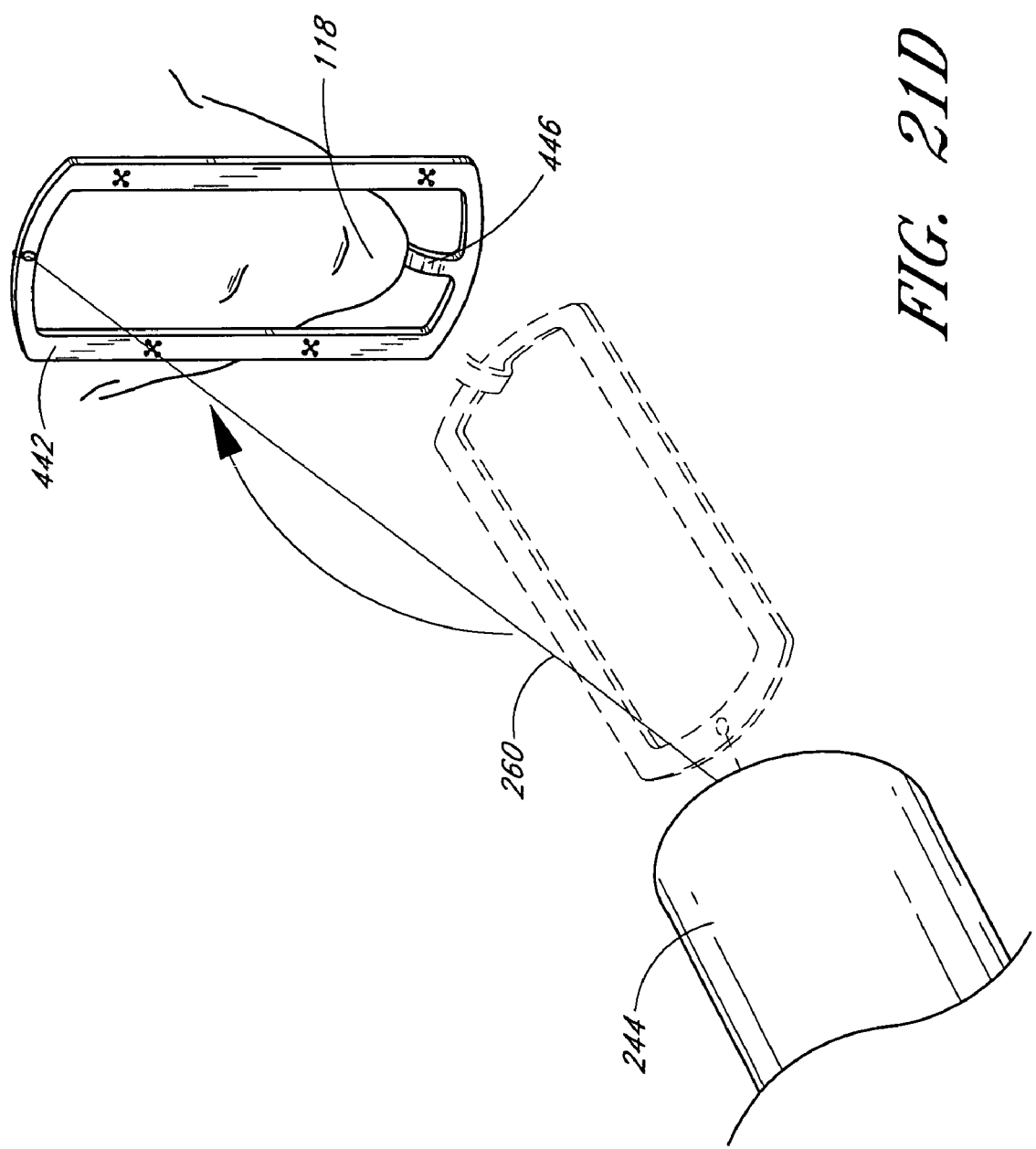

Referring to FIG. 21A, a closure device 440 is preferably delivered to a defect to be occluded, such as a patent foramen ovale. In a patent foramen ovale application, the distal end of the deployment catheter 242 is positioned at or near the patent foramen ovale 120, as shown in FIG. 21A. The position may be confirmed using fluoroscopy, echocardiography, or other imaging. The device 440 is initially in a collapsed state within catheter 242. The device 440 may be releasably attached to an actuator 244, which may be a push rod. The distal end of the deployment catheter 242 is advanced between the septum primum 116 and septum secundum 118 as shown in FIG. 21B. The posterior portion 444 is advanced out of the distal end of the deployment catheter 242 and over the septum primum 116, as shown in FIG. 21C, preferably by withdrawing the catheter 242 proximally. As the catheter 242 is withdrawn, the posterior portion 444 flips over into the left atrium 104 and hooks over the septum primum 116. The intermediate section 446 and anterior sections 442 are then delivered, as shown in FIG. 21D, by further withdrawing the catheter 242 until anterior section 442 flips over the septum secundum 188. After optimal positioning and sealing is achieved, as shown in FIG. 21D, the device 440 can then be detached from the actuator or tether line 260 and deployment catheter 242. The device 440 can also be captured and retrieved at any time during the procedure as long as it is not detached from the actuator.

In one embodiment, the device 440, and more particularly the anterior portion 442, has a length L of about 1 inch, thickness t of about 0.02", and a width W of about 0.475". The length and width of the anterior portion are preferably greater than the length and width of the posterior portion. More preferably, the anterior portion may be approximately twice as long or greater than the posterior portion, and about 25% or more wider than the posterior portion.

Figure 22A:
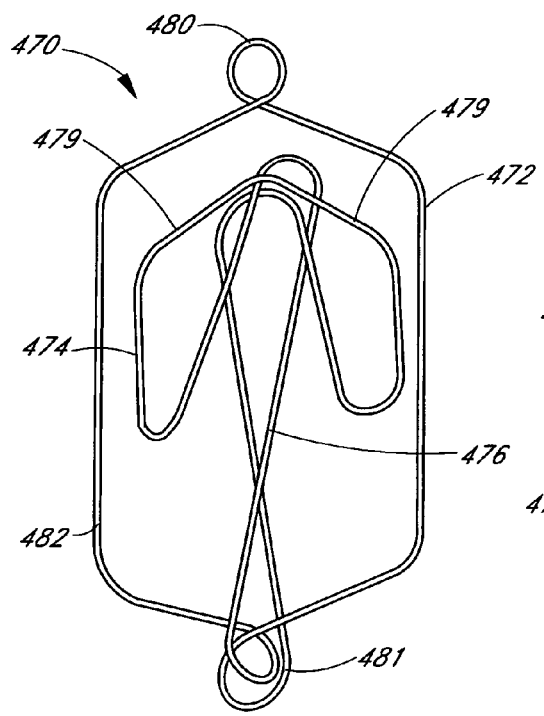
FIG. 22A is a back view of a closure device in accordance with another embodiment of the present invention.
Figure 22B:
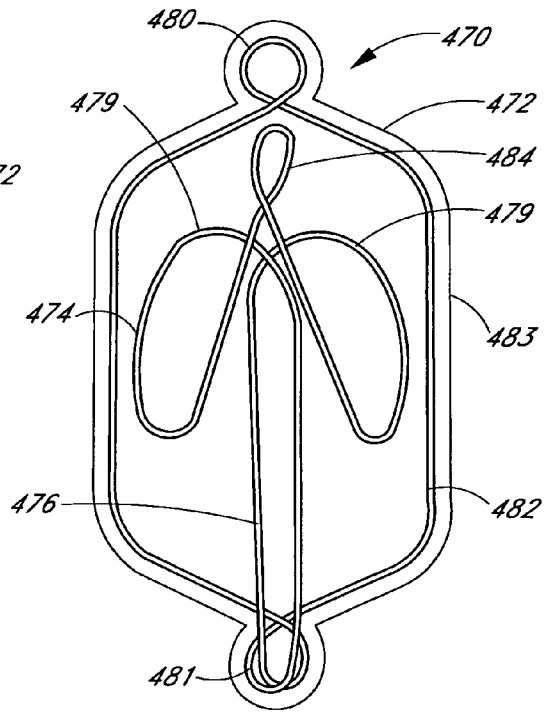
FIG. 22B is a back view of a closure device in accordance with another embodiment of the present invention.

With reference to FIGS. 22A-C and 23, there is illustrated another preferred embodiment of the present invention. The device 470 is preferably made from a single wire structure, and comprises a proximal or an anterior section 472, a distal or posterior section 474, and an intermediate section 476. The posterior section 474 comprises wings 479 which are used to anchor the device into the left atrium. The intermediate section 476 may include crossed wire portions as shown in FIG. 22A or non-crossed wire portions as shown in FIG. 22B. The anterior section may be hexagonal in shape. The anterior, posterior, and intermediate sections 472, 474, 476 are integral and form a structure which hooks over the septum primum and the septum secundum. The device may be provided with at least one loop 480 at a proximal end of the device integral with the structure. A second loop 481 may be provided at the intersection of the anterior and intermediate sections. As shown in FIG. 22B, the device 470 may also comprise a third loop 484 at the distal end of the posterior section 474. The function of the first loop 480, second loop 481, and third loop 484 will be discussed below with reference to loading and deployment of the device 470. The anterior section 472, posterior section 474, intermediate section 476 and at least one loop 480 are preferably an integral structure and are formed of a single wire 482. The device is preferably shaped like a clip, as can be seen with reference to FIG. 23, when the device is deployed.

Figure 23:
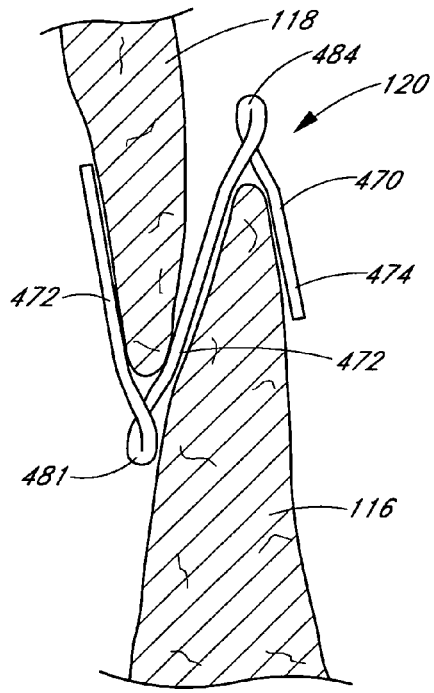
FIG. 23 is a cross-sectional view of a patent foramen ovale closed with the closure device of FIG. 22A or FIG. 22B, shown schematically.

As shown in FIG. 23, the anterior section 472 is positioned in the right atrium, the posterior section 474 is positioned in the left atrium, and the intermediate section 476 is positioned between the septum primum 116 and the septum secundum 118. The posterior section 474 hooks over the septum primum 116 and the anterior section 472 hooks over the septum secundum 118 to occlude a patent foramen ovale 120, as shown in FIG. 23.

Preferably, the wire 482 comprises a metal such as stainless steel, Nitinol, Elgiloy, or others which can be determined through routine experimentation by those of skill in the art. The wire may also be biodegradable. Wires having a circular or rectangular cross-section may be utilized depending upon the manufacturing technique. In one embodiment, a circular cross section wire is cut such as by known laser cutting techniques from tube stock. The closure device is preferably an integral structure, such as a single ribbon or wire, or element cut from a tube stock.

The device may be similarly dimensioned as the embodiment of FIG. 19A. For use in a patent foramen ovale, the overall width of device 470 may be any value or range of values from about 1 cm to about 5 cm, and, in one embodiment, may be about 2.5 cm. The overall length of the closure device 470 may be any value or range of values from about 4 cm to about 20 cm and is, in one embodiment, about 8 cm. Preferably the diameter of the wire may be any value or range of values from about 0.001-0.030 in, and in one preferred embodiment is about 0.015 in.

Figure 22C:
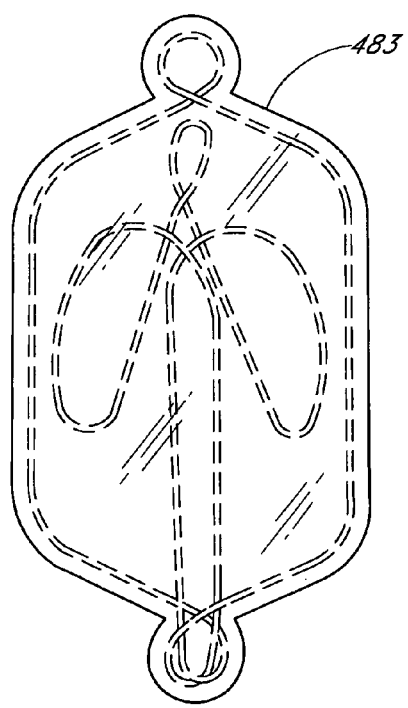
FIG. 22C is a front view of the device of FIG. 22B, showing a laminated structure attached thereto.
Figure 25:
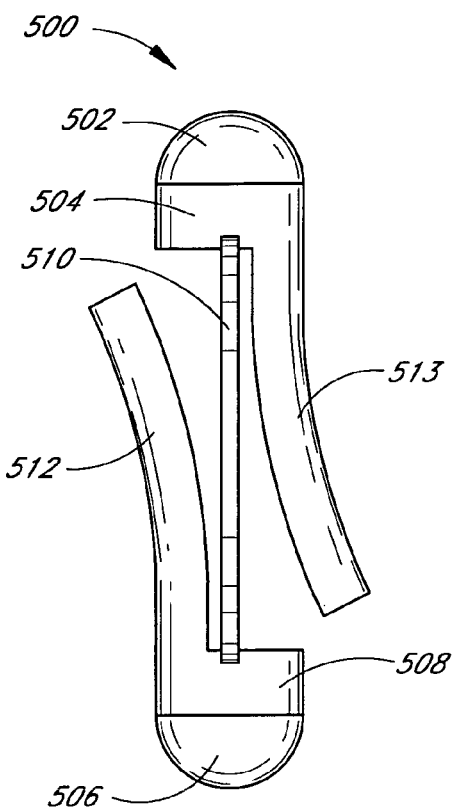
FIG. 25 is a side elevational view of a closure device in accordance with another embodiment of the present invention.
Figure 26:
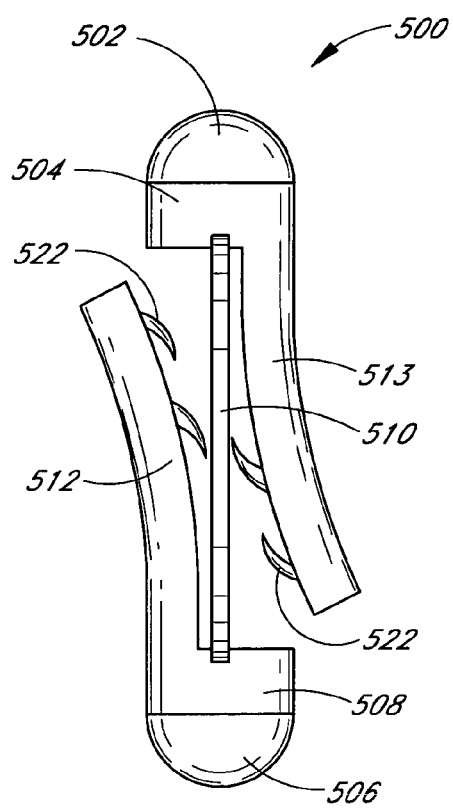
FIG. 26 is a side elevational view of the closure device of FIG. 25 having a plurality of retention structures.

In some embodiments, the anterior section 472 may have a covering or be laminated. FIGS. 22B and 22C show the device of FIG. 22B with a laminate structure 483 covering the anterior section 472. In some embodiments, the lamination may comprise any of a variety of materials which facilitate cellular in-growth, such as ePTFE. The suitability of alternate materials for the lamination material can be determined through routine experimentation by those of skill in the art. In one embodiment, two layers of lamination are provided. The two layers may be bonded to each other around the wire 482 on the anterior section 472 in any of a variety of ways, such as by heat bonding with or without an intermediate bonding layer such as polyethylene or FEP, adhesives, sutures, and other techniques which will be apparent to those of skill in the art in view of the disclosure herein. The lamination material in one embodiment preferably is securely attached to the device 470 and retains a sufficient porosity to facilitate cellular ingrowth and/or attachment.

Referring to FIGS. 24A-D, there is illustrated a preferred method of loading the device illustrated in FIG. 22B for delivery. A mounting shaft 486 is inserted through the second loop 481 of the device 470 such that the anterior section 472 is closer to the proximal end 490 of the mounting shaft 486 and the posterior section 474 is closer to the distal end 488 of the mounting shaft 486, as shown in FIG. 24A. As shown in FIG. 24B, the posterior section 474 and the intermediate section 476 are bent distally such that each wire of the intermediate section 476 is placed along opposite sides of the mounting shaft 486. The portion between the intermediate section 476 and the posterior section 474 rests on the mounting shaft 486 with the third loop 484 extending somewhat radially from the mounting shaft 486. The third loop 484 is then bent over the distal end 488 of the mounting shaft 486, as shown in FIG. 24C.

A tether line 492 is looped through the first loop 480 on the proximal end of the device. A recapture wire 494 is inserted through the tether line 492 loop. The recapture wire 494 preferably does not pass through the first loop 480 of the device, as shown in FIG. 24D. When the tether line 492 is drawn proximally, the tether line cinches the first loop 480 of the device 470. The tether line 492 is then drawn proximally such that the anterior section 472 is an adjacent to the mounting shaft 486. In another embodiment, the mounting shaft 486 may first be inserted through the first loop 480 and fixed with a tether line 492, followed by the mounting procedure as explained previously. The device 470, tether line 492, recapture wire 494, and mounting shaft 486 are then inserted into a sheath (not shown).

The placement of the closure device 470 is schematically shown in FIG. 23. For deployment, the sheath is advanced through the channel 122 of the patent foramen ovale, such that the distal end of the sheath extends into the left atrium 104 beyond the tip 130 of the septum primum 116. The mounting shaft 486 is held in place while the sheath is slowly retracted proximally until the posterior section 474 is released from the sheath. The wings 479 of the posterior section 474 may be extended out by slightly advancing the sheath distally while holding the mounting shaft 486 in place. The mounting shaft 486 and the sheath are then retracted proximally until the wings 479 of the posterior section 474 engage the septum primum 116. The mounting shaft 486 is held in place while the sheath is retracted proximally allowing the wings 479 to secure the septum primum. The sheath is then retracted further until the entire device 470 is exposed.

The tether line 492 and recapture wire 494 are advanced distally, allowing the anterior section 472 to advance and oppose the right atrium side of the septum secundum. With the tether line 492 and recapture wire 494 still secured to the first loop 480, the entire device 470 may be recaptured if required. The tether line 492 and recapture wire 494 may also assist in repositioning the anterior section 472 of the device. Optimal positioning of the device may be confirmed using fluoroscopy, echocardiography, or other imaging. Once optimal positioning is confirmed, the mounting shaft is retracted proximally, and the recapture wire 494 is withdrawn proximally to release the tether line 492 loop. The mounting shaft 486, tether line 492, recapture wire 494, and sheath are then removed.

Figure 27:
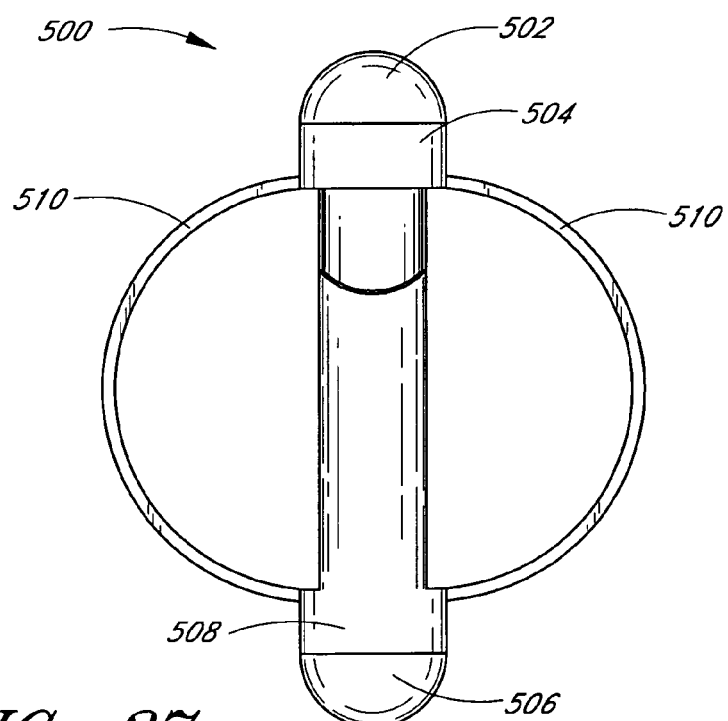
FIG. 27 is a rear elevational view of the closure device of FIG. 25.

Referring to FIGS. 25-32, there is illustrated another preferred embodiment of the present invention. The device is shown in an unexpanded state in FIGS. 25 and 26. A closure device 500 is provided having a soft distal tip 502, connected to a distal hub 504, and a soft proximal tip 506, connected to a proximal hub 508. The device also comprises at least two sealing arms 510. The sealing arms 510 are preferably heat-set. When the device is expanded, the arms 510 have a generally round shape, as shown in FIG. 27. The device 500 also comprises at least two anchors 512, 513 integrally formed with the distal and proximal hubs 504, 508 and the sealing arms 510. The anchors deflect outwards upon expansion to retain the septum primum 116 and septum secundum 118, as will be described. The device 500 is preferably made from a laser-cut hypotube. The distal hub 504 and proximal hub 508 are drawn together, thereby compressing the device 500 and expanding the sealing arms 510 for positioning in a patent foramen ovale 120 channel 122.

Preferably, the closure device 500 is provided with one or more retention structures for retaining the device in the patent foramen ovale or other similar septal defects. See FIG. 26. In the illustrated embodiment, a plurality of barbs or other anchoring elements 522 are provided, for engaging adjacent tissue to retain the closure device 500 in its implanted position and to limit relative movement between the tissue and the closure device. The illustrated barbs 522 are provided on the anchors 512, 513. The barbs resist migration of the closure device away from the patent foramen ovale.

Figure 28:
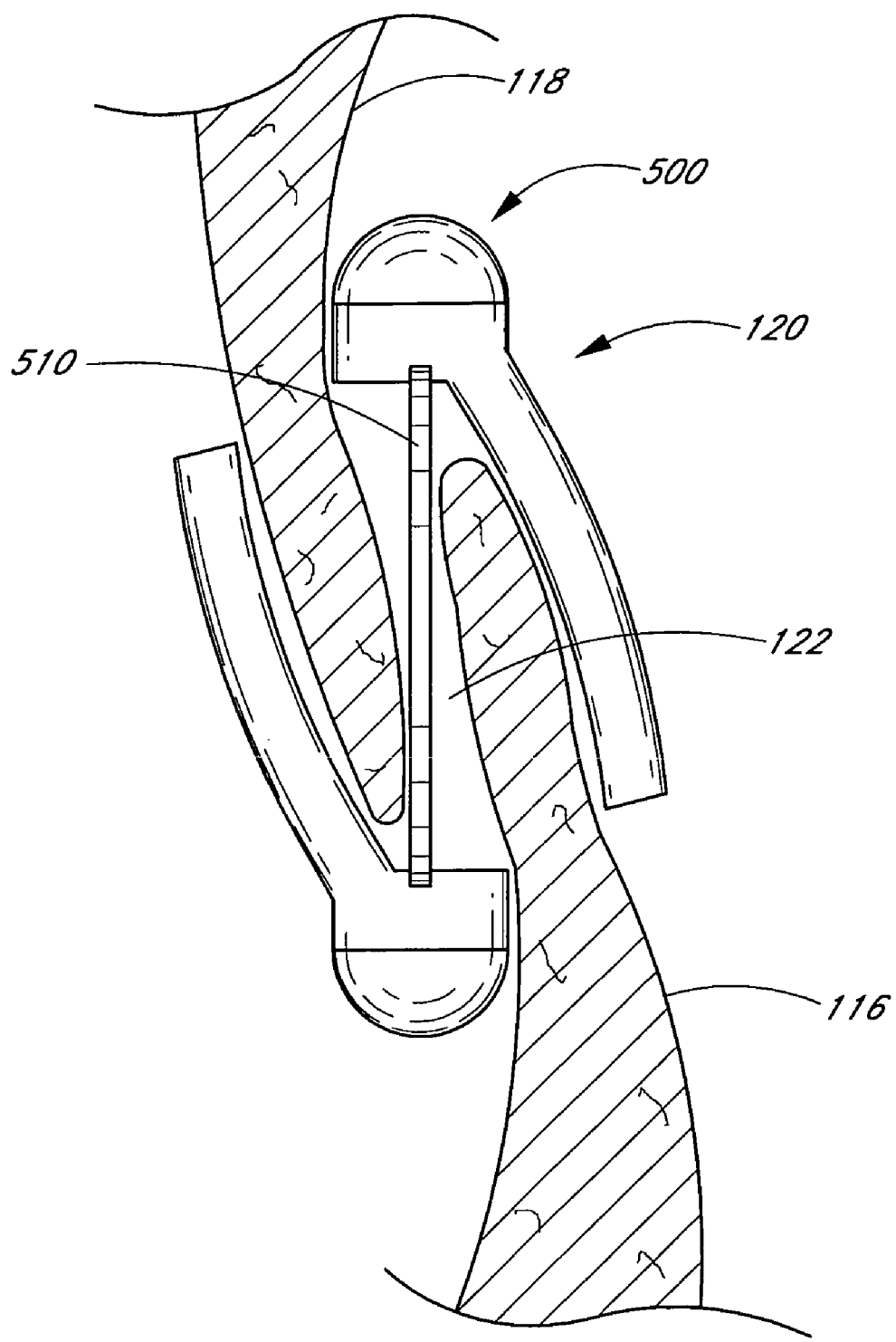
FIG. 28 is a partial cross-sectional view of a patent foramen ovale closed with the closure device of FIG. 25.
Figures 29, 30:
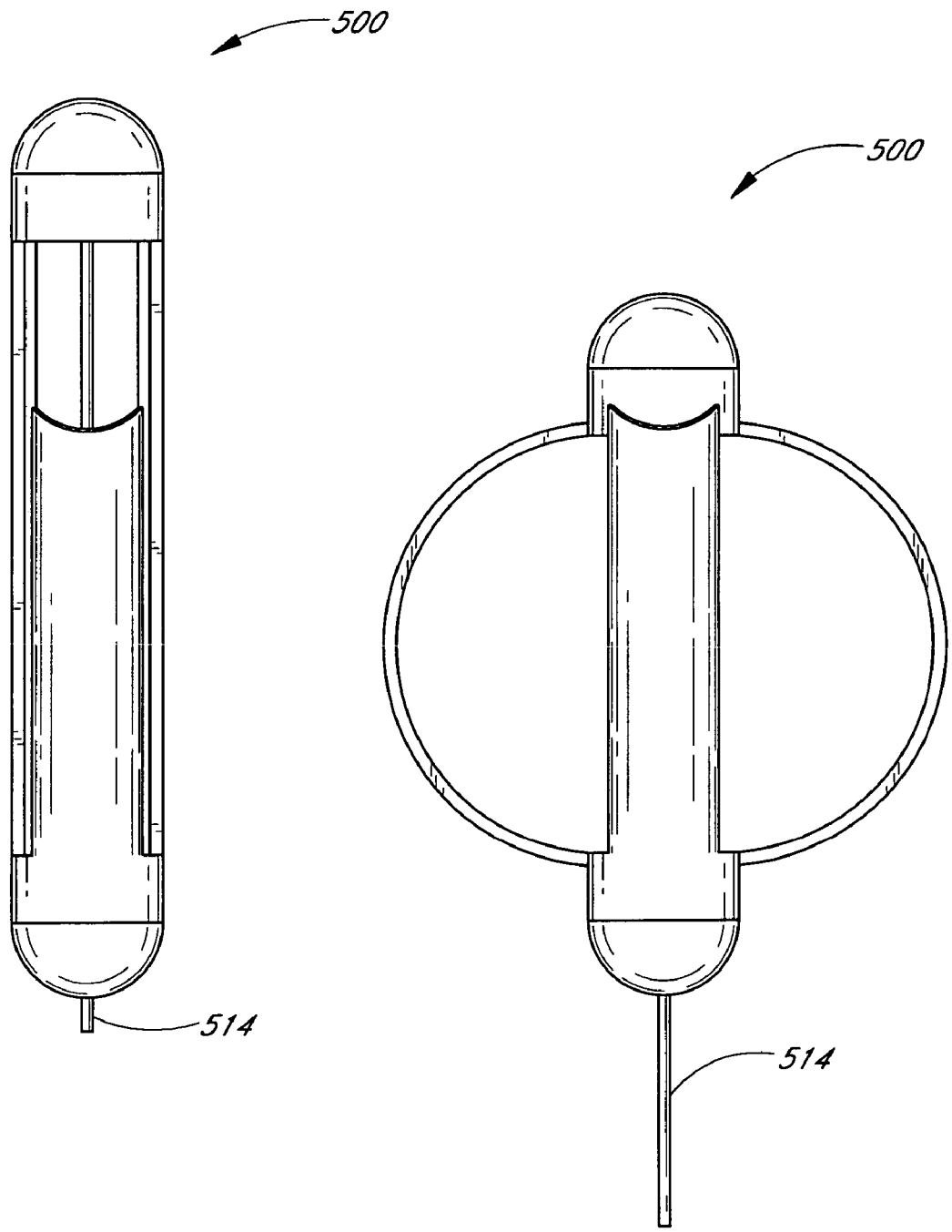
FIG. 29 is a front elevational view of the closure device of FIG. 25 prior to expansion having a pull wire expansion system.
FIG. 30 is a front elevational view of the closure device of FIG. 25 after expansion having a pull wire expansion system.
Figures 31, 32:
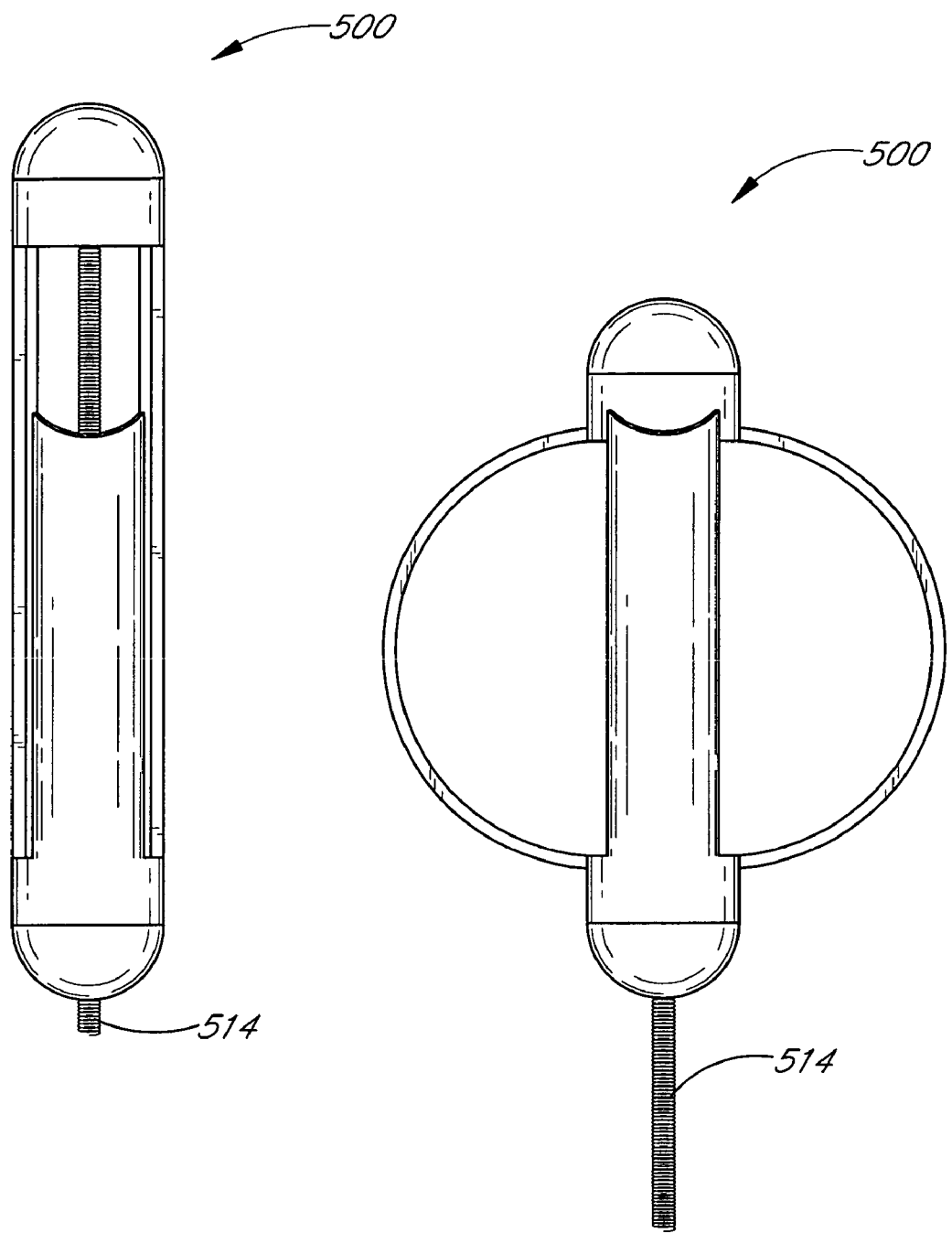
FIG. 31 is a front elevational view of the closure device of FIG. 25 prior to expansion having a twisting expansion system.
FIG. 32 is a front elevational view of the closure device of FIG. 25 after expansion having a twisting expansion system.

The arms 510 are preferably positioned in the channel 122 between the septum primum 116 and the septum secundum 118 to close the patent foramen ovale 120, as shown in FIG. 28. A first anchor 513 is positioned in the left atrium, while a second anchor 512 is positioned in the right atrium. The anchors 512, 513 deflect outwardly to secure the septum primum 116 and septum secundum 118, to close the patent foramen ovale 120.

Preferably, the device 500 is formed of a metal such as stainless steel, Nitinol, Elgiloy, or others which can be determined through routine experimentation by those of skill in the art. The material may also be biodegradable. Material having a circular, rectangular, or other cross-section may be utilized depending upon the manufacturing technique. One of ordinary skill in the art will recognize various methods of manufacturing the device 500. In one embodiment, for example, material with a circular cross section is cut such as by known laser cutting techniques from tube stock. The closure device is preferably an integral structure, such as a single ribbon or wire, or element cut from a tube stock.

The device may also comprise a sleeve over at least a portion of the device. The sleeve may comprise any of a variety of materials which facilitate cellular in-growth, such as ePTFE. The suitability of alternate materials for sleeve can be determined through routine experimentation by those of skill in the art. In one embodiment, the sleeve comprises two layers. The two layers may be bonded to each other around the device in any of a variety of ways, such as by heat bonding with or without an intermediate bonding layer such as polyethylene or FEP, adhesives, sutures, and other techniques which will be apparent to those of skill in the art in view of the disclosure herein. The sleeve in one embodiment preferably is securely attached to the device 500 and retains a sufficient porosity to facilitate cellular ingrowth and/or attachment.

The device 500 is further provided with an expansion and detachment element 514 at its distal end. The expansion and detachment element 514 may be either a pull wire design (FIGS. 29-30), a turn screw design (FIGS. 31-32), a tether line, or other method known by one of ordinary skill in the art that may be used to collapse and lock the closure device in its expanded state. In one embodiment, the device is preferably attached via detachment element 514 to a delivery system as described above prior to deployment, and is then detached at detachment element 514 when properly positioned. The device can then be detached from the delivery system at the same place. In one embodiment, deployment and detachment of the device may be accomplished by torque rods, as discussed previously with reference to FIGS. 11A-B. In another embodiment, deployment and detachment may be accomplished by tether lines as previously discussed. Other methods that are known by one of ordinary skill in the art may also be used.

Umbrella and Acorn Embodiments

Figure 33:
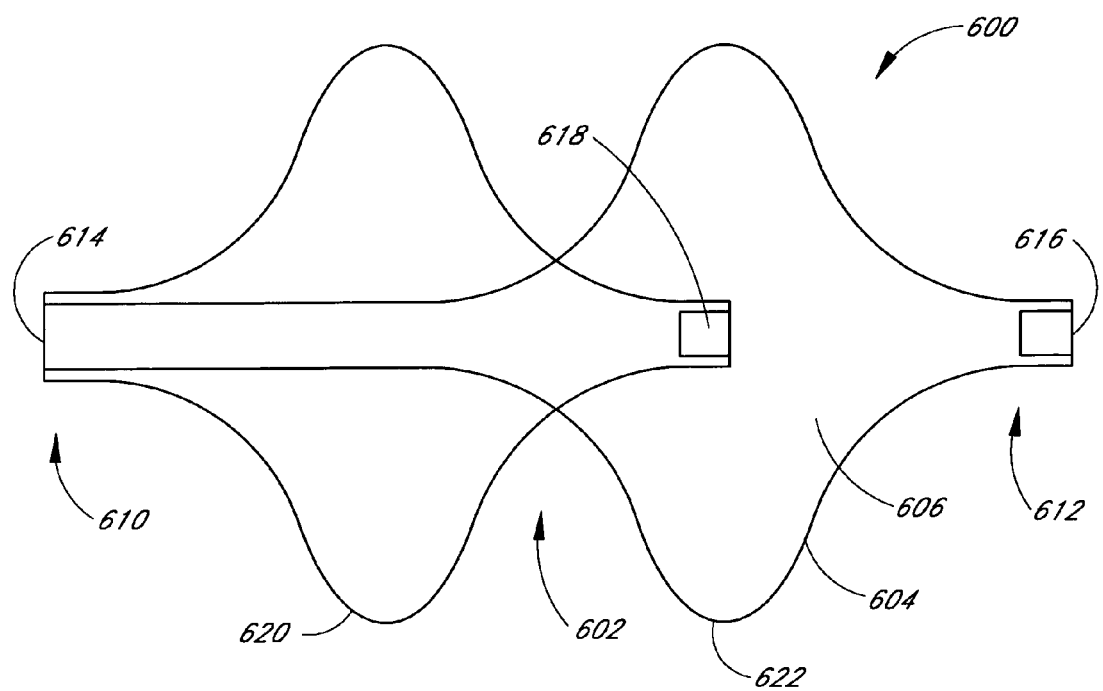
FIG. 33 is a schematic side view of a closure device in accordance with another embodiment of the present invention.
Figure 34:
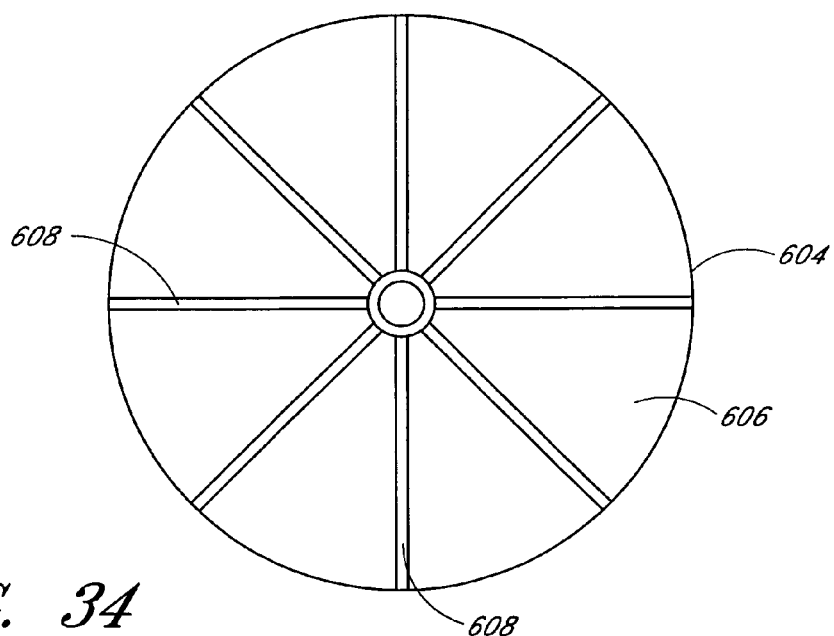
FIG. 34 is an end view of the closure device of FIG. 33.

Referring to FIGS. 33-34, alternate structures of a closure device in accordance with the present invention are illustrated. The closure device 600 comprises an occluding member 602 comprising a frame 604 and a barrier 606. In the illustrated embodiment the frame 604 comprises a plurality of radially outwardly extending spokes 608 each having a length within the range of from about 1 cm to 6 cm. The device has a proximal end 610 and a distal end 612 corresponding to a proximal hub 614 and a distal hub 616. A central hub 618 is also preferably provided between the proximal hub 614 and distal hub 616. The frame 604 and barrier 606 form a proximal segment 620 and a distal segment 622. The designation proximal or distal is not intended to indicate any particular anatomical orientation or deployment orientation within the deployment catheter. Proximal and distal segments 620, 622 are baskets which secure the septum primum 116 and septum secundum 118 on both sides, thus sealing the patent foramen ovale.

The spokes 608 are advanceable from a generally axially extending orientation such as from within a tubular introduction catheter to a radially inclined orientation. In a self-expandable embodiment, the spokes are biased radially outwardly such that the closure member expands to its enlarged, implantation cross-section under its own bias following deployment from the catheter. Alternatively, the closure member may be enlarged using any of a variety of enlargement structures such as an inflatable balloon, or a catheter for axially shortening the closure member, as is discussed further below. In yet a further embodiment, expansion of the device may be accomplished by torque rods, as discussed previously with reference to FIGS. 11A-B. The proximal hub 614 may threadingly engage the torque rod such that rotation of the torque rod will expand or contract the device 600. The distal hub 616 may operate to support the distal end of the torque rod, permitting the torque rod to rotate freely upon its axis with the distal hub 616. In another embodiment, the distal hub 616 may also be threadingly engaged to the torque rod.

For deployment, the device 600 is preferably advanced through the channel 122 of the patent foramen ovale 120 until the distal end of the catheter is beyond the tip 130 of the septum primum 116. The device 600 is preferably advanced until the distal end 616 of the device 600 extends into the left atrium 104. The distal segment 622 is exposed from the catheter, such that it expands to its enlarged, implantation cross-section and engages the septum primum 116 wall on the left atrium 104 side. The device 600 then is then drawn proximally to draw the septum primum 116 toward the septum secundum 118, closing the channel 122. The proximal segment 620 of the device 600 is then exposed and permitted to expand to its enlarged, implantation cross-section, securing the septum secundum 118 to the septum primum 116.

Depending upon the desired introduction crossing profile of the collapsed closure device 600, as well as structural strength requirements in the deployed device, anywhere within the range of from about 3 spokes to about 40 spokes may be utilized. In some embodiments, anywhere from about 12 to about 24 spokes are utilized, and 18 spokes are utilized in one embodiment.

Preferably, the spokes comprise a metal such as stainless steel, Nitinol, Elgiloy, or others which can be determined through routine experimentation by those of skill in the art. Wires having a circular or rectangular cross-section may be utilized depending upon the manufacturing technique. In one embodiment, rectangular cross section spokes are cut such as by known laser cutting techniques from tube stock, a portion of which forms the hubs 614, 616, 618.

The barrier 606 may comprise any of a variety of materials which facilitate cellular in-growth, such as ePTFE. The suitability of alternate materials for barrier 606 can be determined through routine experimentation by those of skill in the art. The barrier 606 may be provided on either one or preferably both axially facing sides of the closure member. In one embodiment, the barrier 606 comprises two layers, with one layer on each side of the frame 604. The two layers may be bonded to each other around the spokes 608 in any of a variety of ways, such as by heat bonding with or without an intermediate bonding layer such as polyethylene or FEP, adhesives, sutures, and other techniques which will be apparent to those of skill in the art in view of the disclosure herein. The barrier 606 preferably has a thickness of no more than about 0.003 in.

For use in a patent foramen ovale, the occluding member 600 has an expanded diameter within the range of from about 10 mm to about 40 mm, and, in one embodiment, about 20 mm. The overall length of the closure device 600 from the distal end 612 to the distal end 610 is within the range of from about 40 mm to about 100 mm and, in one embodiment, about 70 mm.

Figure 35:
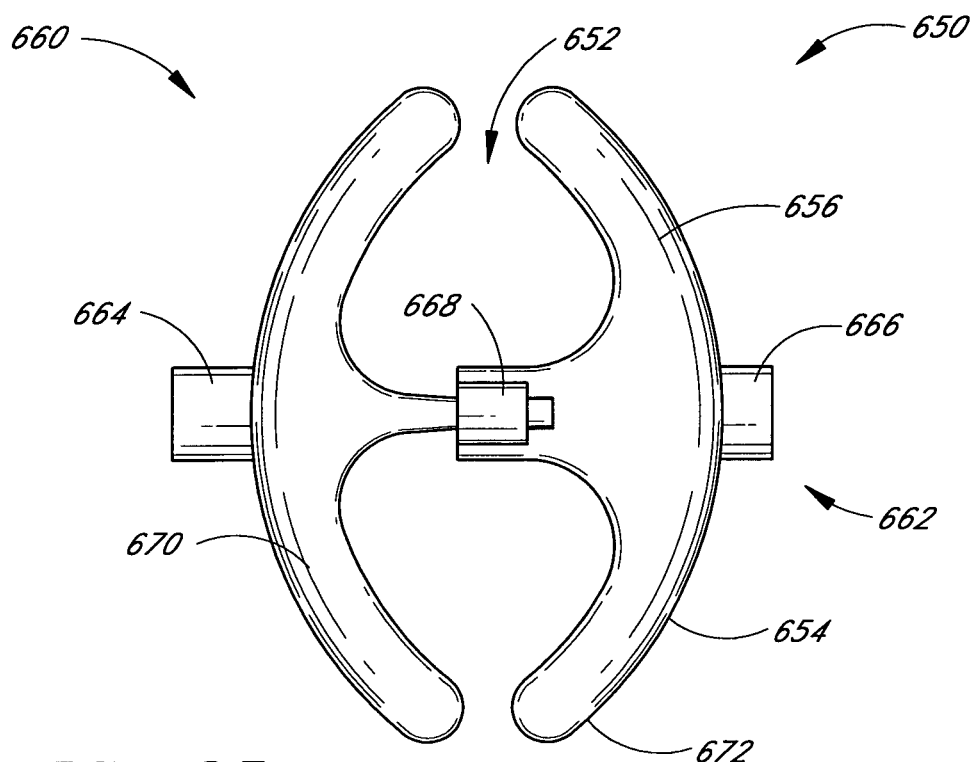
FIG. 35 is a side view of a closure device in accordance with another embodiment of the present invention.
Figure 36:
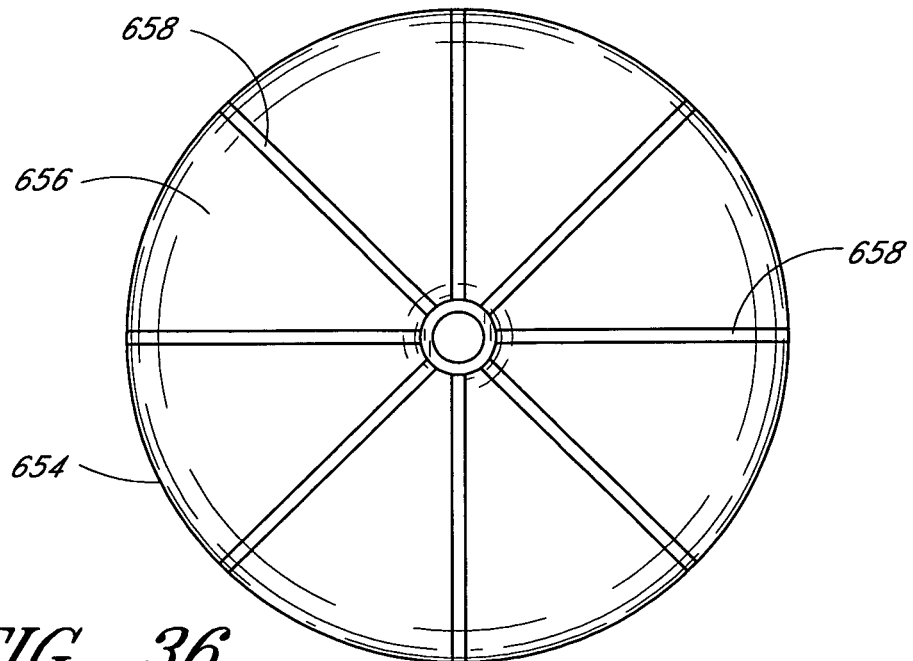
FIG. 36 is an end view of the closure device of FIG. 35.

Modifications to the closure device are illustrated in FIGS. 35-36. The closure device 650 comprises a closure member 652 comprising a frame 654 and a barrier 656. In the illustrated embodiment the frame 654 comprises a plurality of radially outwardly extending spokes 658. The device has a proximal end 660 and a distal end 662, corresponding to a proximal hub 664 and a distal hub 666. A central hub 668 is also preferably provided between the proximal hub 664 and distal hub 666. The frame 654 and barrier 656 form a proximal segment 670 and a distal segment 672. The designation proximal or distal is not intended to indicate any particular anatomical orientation or deployment orientation within the deployment catheter. Proximal and distal segments 670, 672 are concave faced baskets, which secure the septum primum and septum secundum on both sides, thus sealing the patent foramen ovale. Deployment of the device 650 preferably corresponds to the deployment discussed above with reference to FIGS. 33-34.

Figure 37:
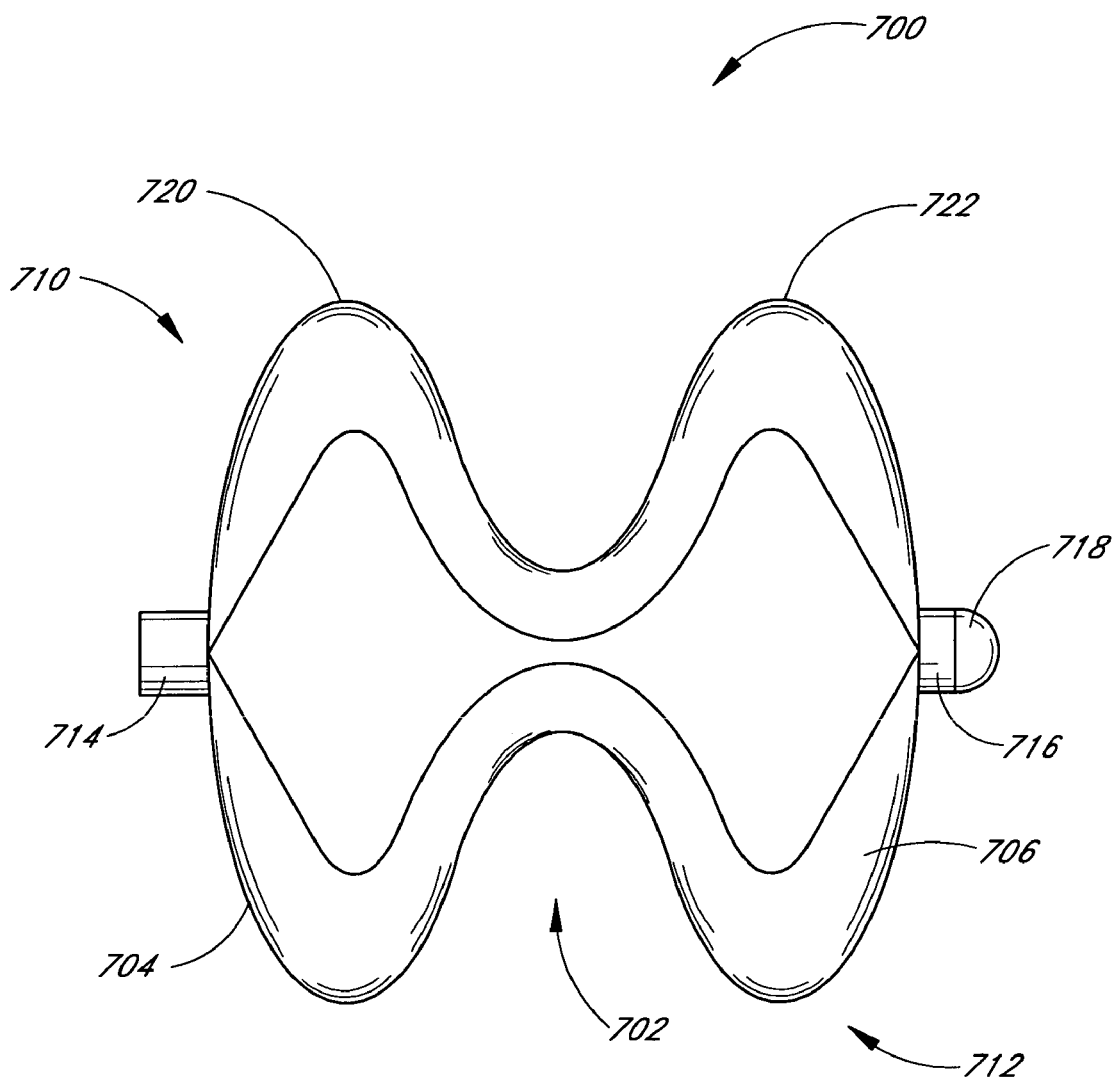
FIG. 37 is a side view of a closure device in accordance with another embodiment of the present invention.
Figure 38A:
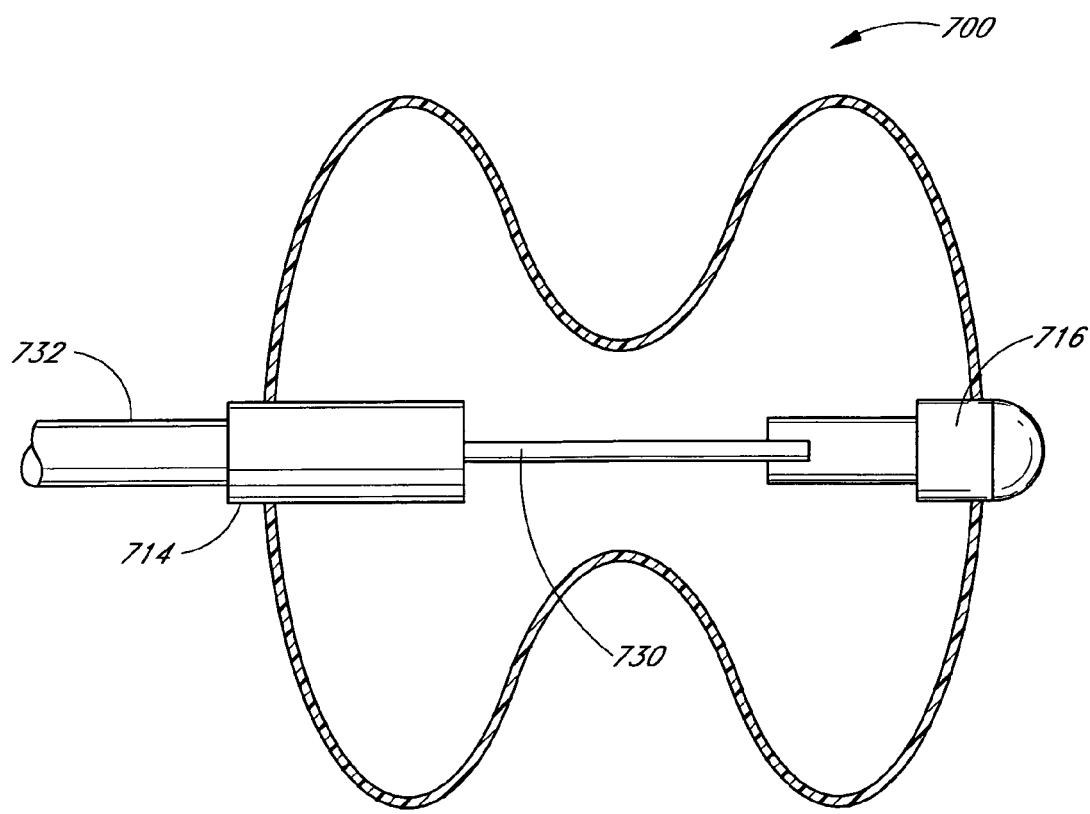
FIGS. 38A-B are side schematic views showing the expansion of the closure device of FIG. 37.
Figure 38B:
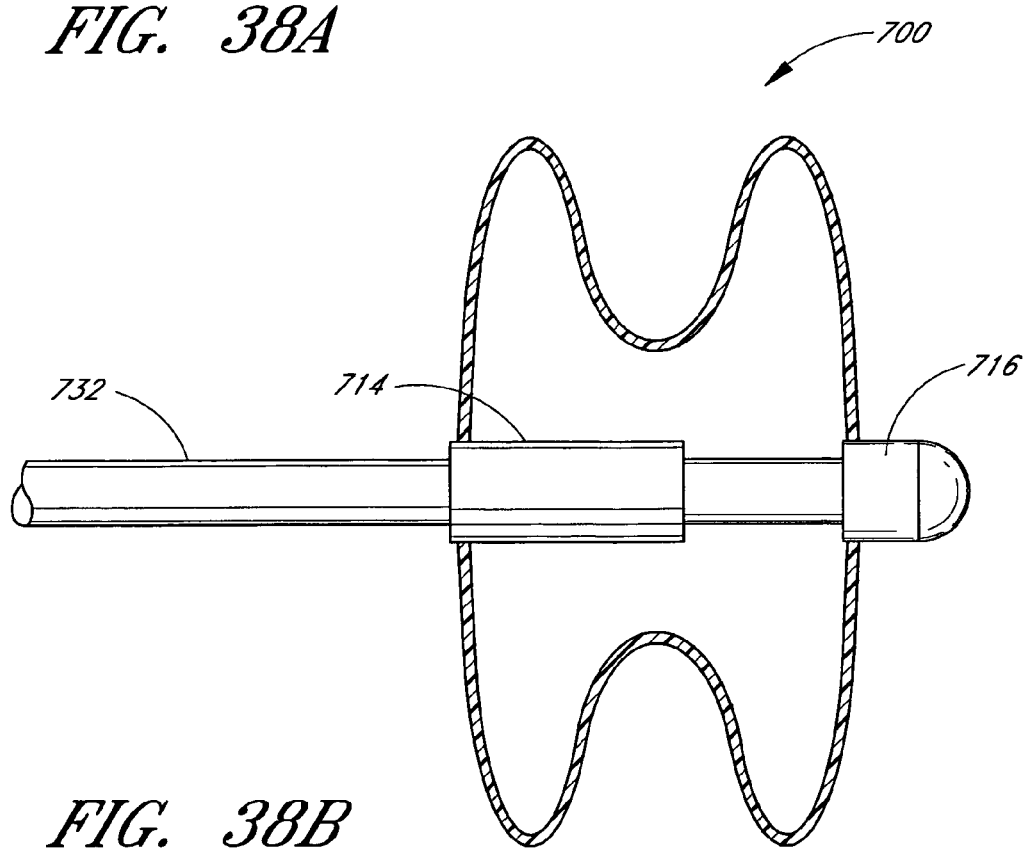

Referring to FIGS. 37 and 38A-B, a further variation of the closure device is shown. The closure device 700 comprises a closure member 702 comprising a frame 704 and a barrier 706. In one embodiment, the frame 704 comprises a plurality of radially outwardly extending supports (not shown). The device has a proximal end 710 and a distal end 712 corresponding to a proximal hub 714 and a distal hub 716. A soft distal tip 718 is also preferably provided at the distal end 712, and is connected to distal hub 716. The frame 704 and barrier 706 form a proximal segment 720 and a distal segment 722. The designation proximal or distal is not intended to indicate any particular anatomical orientation or deployment orientation within the deployment catheter. Proximal and distal segments 720, 722 behave like baskets to secure the septum primum and septum secundum on both sides, thus sealing the patent foramen ovale.

With reference to FIG. 38A, the device is shown in an unexpanded state. Proximal retraction on the deployment line 730 while resisting proximal movement of proximal hub 714 such as by using the distal end of the catheter 732 will cause the distal hub 716 to be drawn towards the proximal hub 714, thereby radially enlarging the cross-sectional area of the closure device 700, as shown in FIG. 38B. Depending upon the material utilized for the closure device 700, the supports 708 will retain the radially enlarged orientation by elastic deformation, or may be retained in the enlarged orientation such as by securing a slip knot immovably to the deployment line 730 at the fully radially enlarged orientation. This may be accomplished in any of a variety of ways, using additional knots, clips, adhesives, or other techniques known in the art. A variety of alternative structures may be utilized, to open or enlarge the closure device 700 under positive force, such as using a pullwire or a torque element, as will be discussed in further detail hereinafter. Deployment of the device 700 preferably corresponds to the deployment discussed above with reference to FIGS. 33-34.

Figure 39:
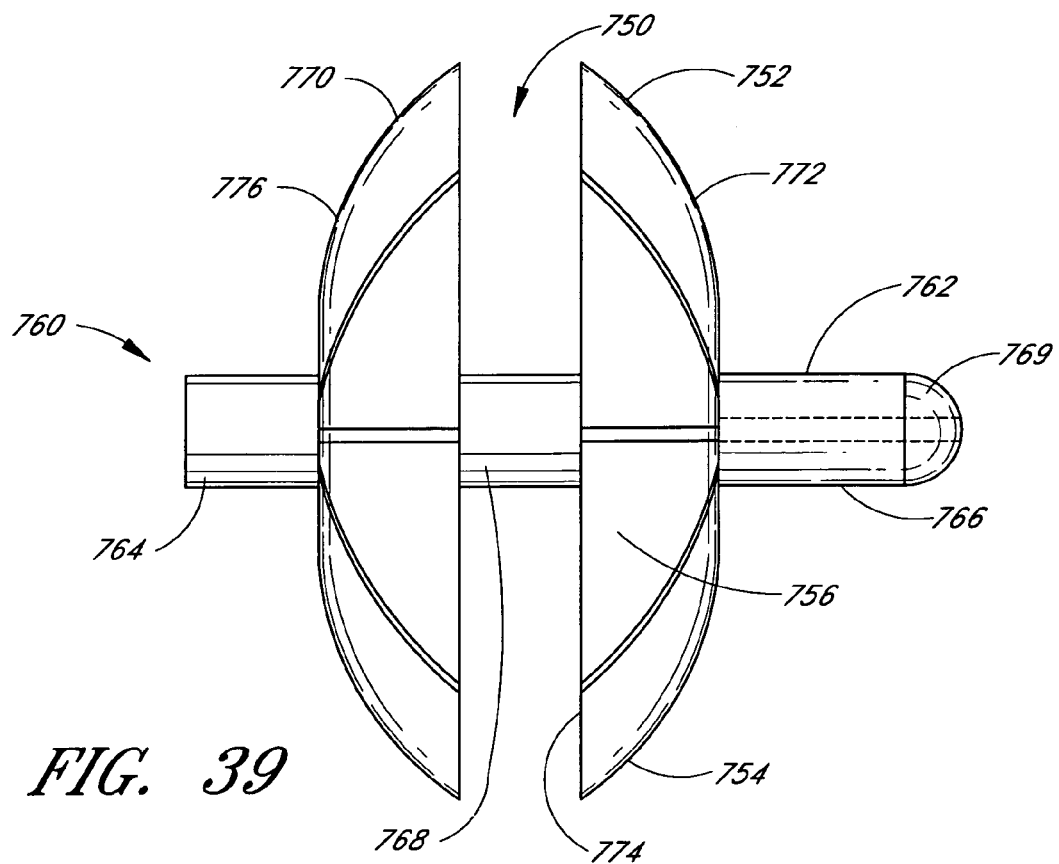
FIG. 39 is a side view of a closure device in accordance with another embodiment of the present invention.
Figure 40:
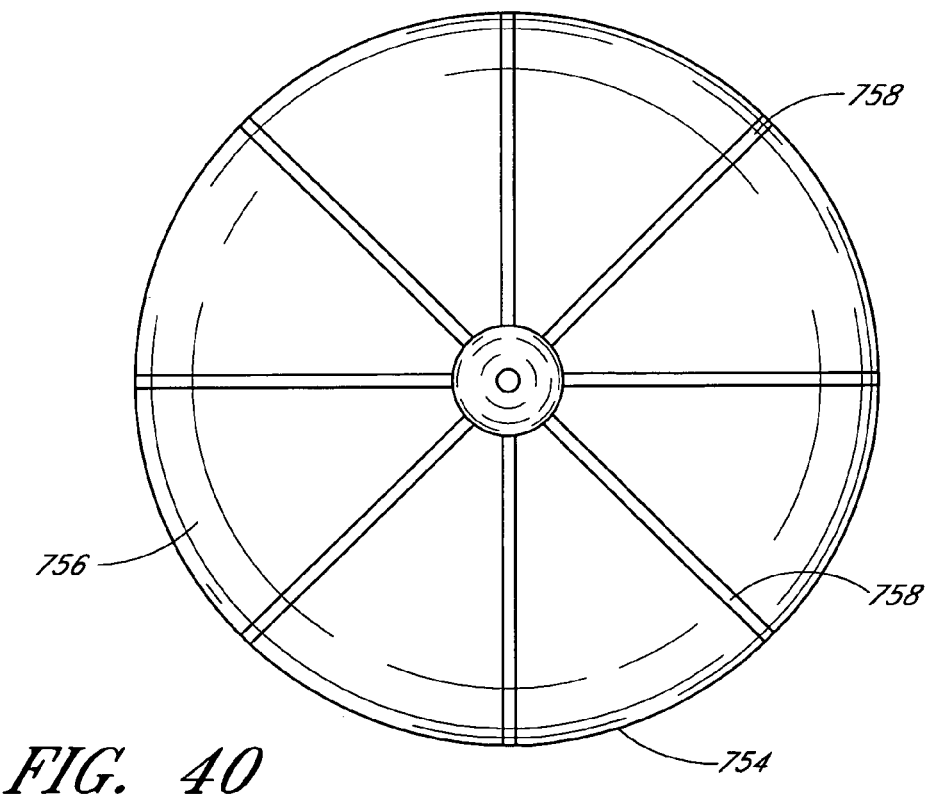
FIG. 40 is an end view of the closure device of FIG. 39.
Figure 41:
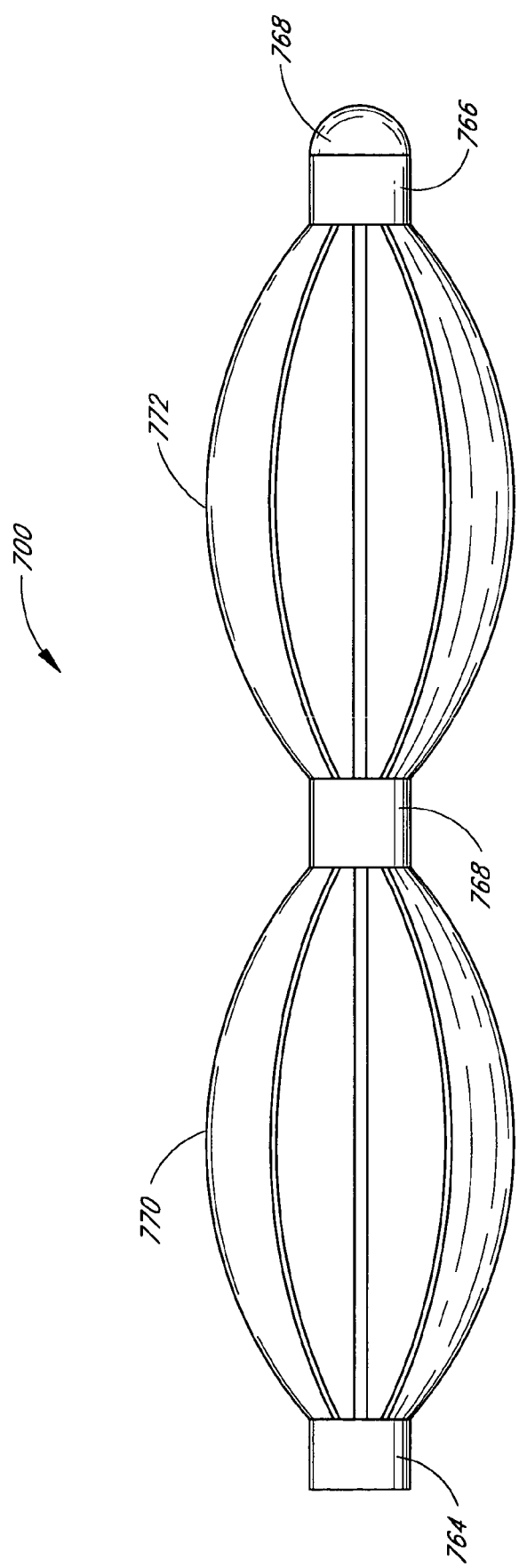
FIG. 41 is a side view of the closure device of FIG. 39 in a collapsed state.

With reference to FIGS. 39-41, the closure device 750 comprises an occluding member 752 comprising a frame 754 and a barrier 756. In the illustrated embodiment the frame 754 comprises a plurality of radially outwardly extending spokes 758. The device has a proximal end 760 a distal end 762 corresponding to a proximal hub 764 and a distal hub 766. A central hub 768 is also preferably provided between the proximal hub 764 and distal hub 766. A soft distal tip 769 is also preferably provided at the distal end 762, and is connected to distal hub 766. The frame 754 and barrier 756 form a proximal segment 770 and a distal segment 772. The designation proximal or distal is not intended to indicate any particular anatomical orientation or deployment orientation within the deployment catheter. Proximal and distal segments 770, 772 are umbrellas which secure the septum primum and septum secundum on both sides, sealing the patent foramen ovale. The proximal and distal segments 770, 772 have a generally concave inwardly facing surface 774 and convex outwardly facing surface 776. The device is shown in a collapsed state in FIG. 41. Deployment of the device 750 preferably corresponds to the deployment discussed above with reference to FIGS. 33-34.

Figure 42:
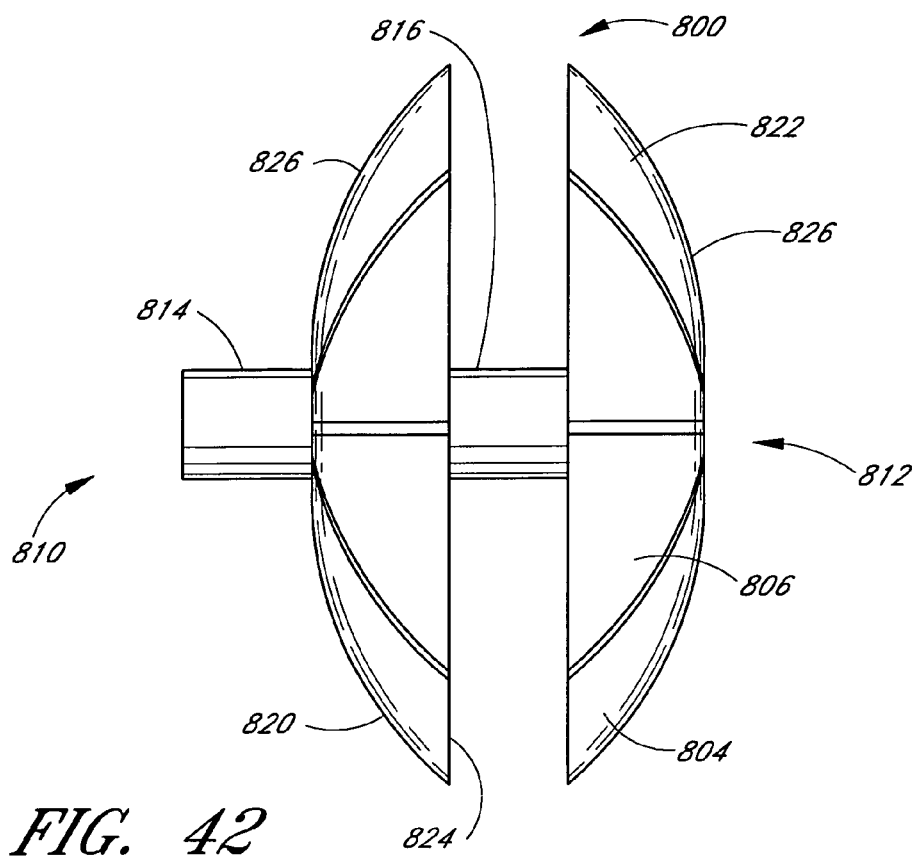
FIG. 42 is a side view of a closure device in accordance with another embodiment of the present invention.
Figure 43:
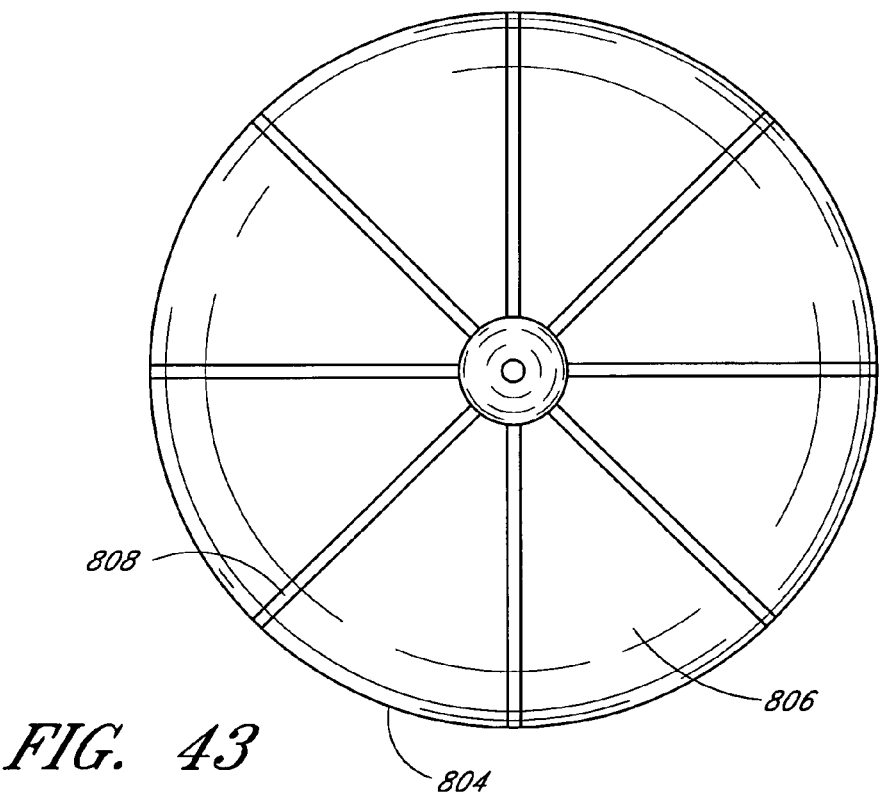
FIG. 43 is an end view of the closure device of FIG. 42.
Figure 45:
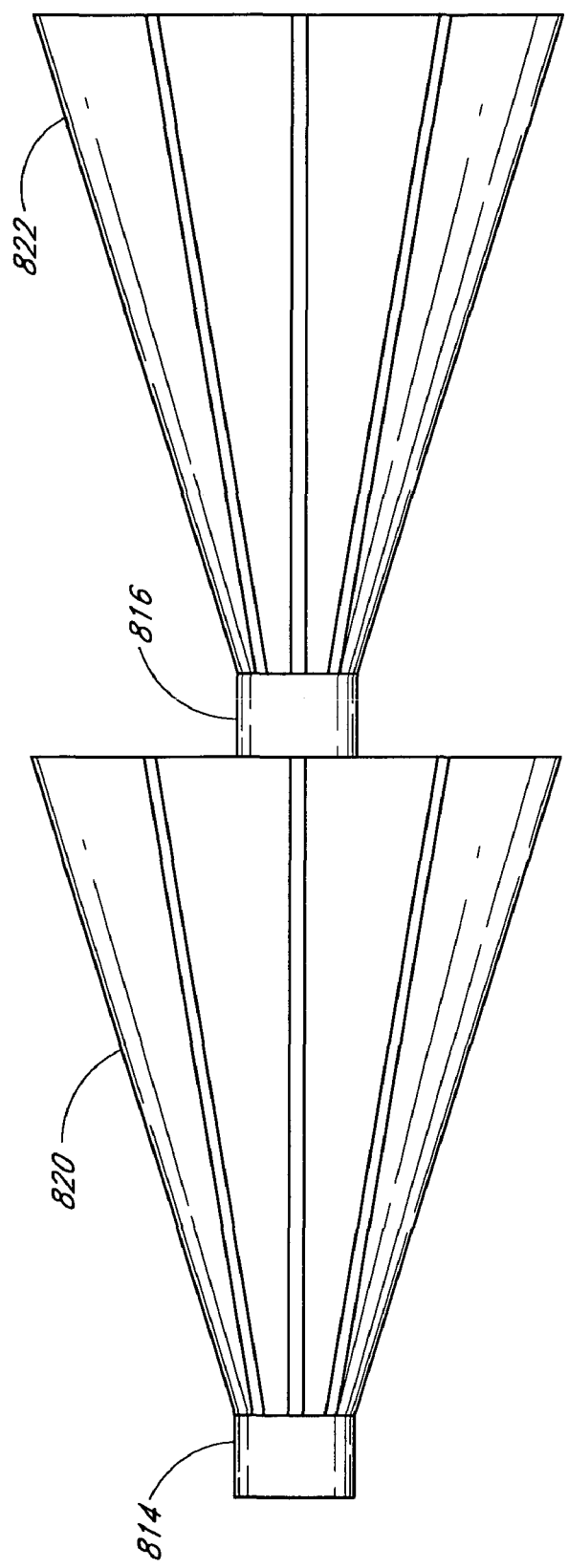
FIG. 45 is a side view of the closure device of FIG. 42 in a collapsed state.

Referring to FIGS. 42-43 and 45, a variation of the closure device is shown. The closure device 800 comprises a frame 804 and a barrier 806. In the illustrated embodiment the frame 804 comprises a plurality of radially outwardly extending spokes 808. The device has a proximal end 810 a distal end 812 corresponding to a proximal hub 814 and a distal hub 816. The frame 804 and barrier 806 form a proximal segment 820 and a distal segment 822. The designation proximal or distal is not intended to indicate any particular anatomical orientation or deployment orientation within the deployment catheter. Proximal and distal segments 820, 822 are umbrellas which secure the septum primum and septum secundum on both sides, thus sealing the patent foramen ovale. The proximal and distal segments 820, 822 have a generally flat inwardly facing surface 824 and an angled outwardly facing surface 826. The device 800 is shown in a collapsed position in FIG. 45. Deployment of the device 800 preferably corresponds to the deployment discussed above with reference to FIGS. 33-34.

Figure 44A:
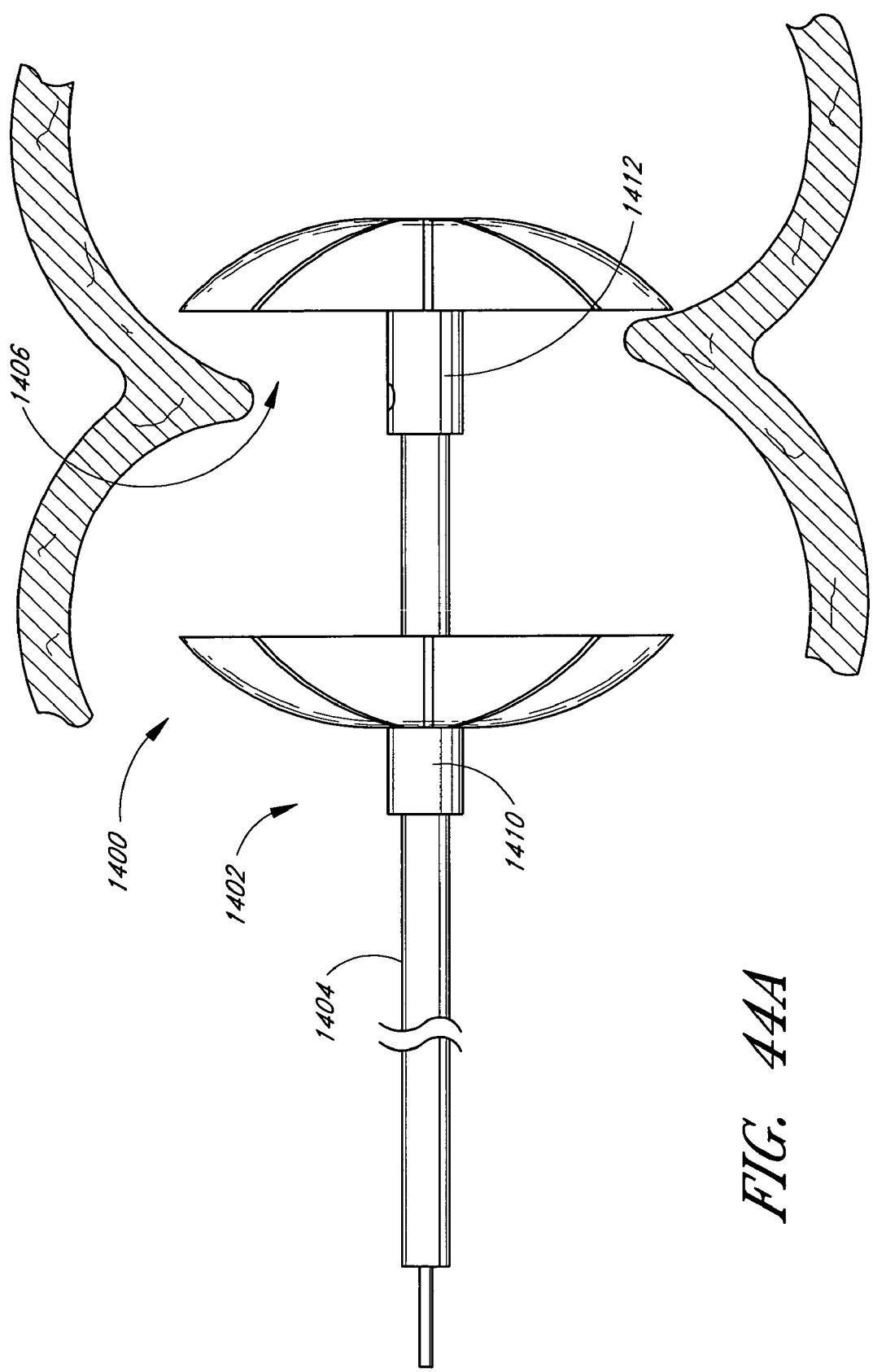
FIGS. 44A-C are schematic views of a defect closure procedure in accordance with one embodiment of the present invention.
Figure 44B:
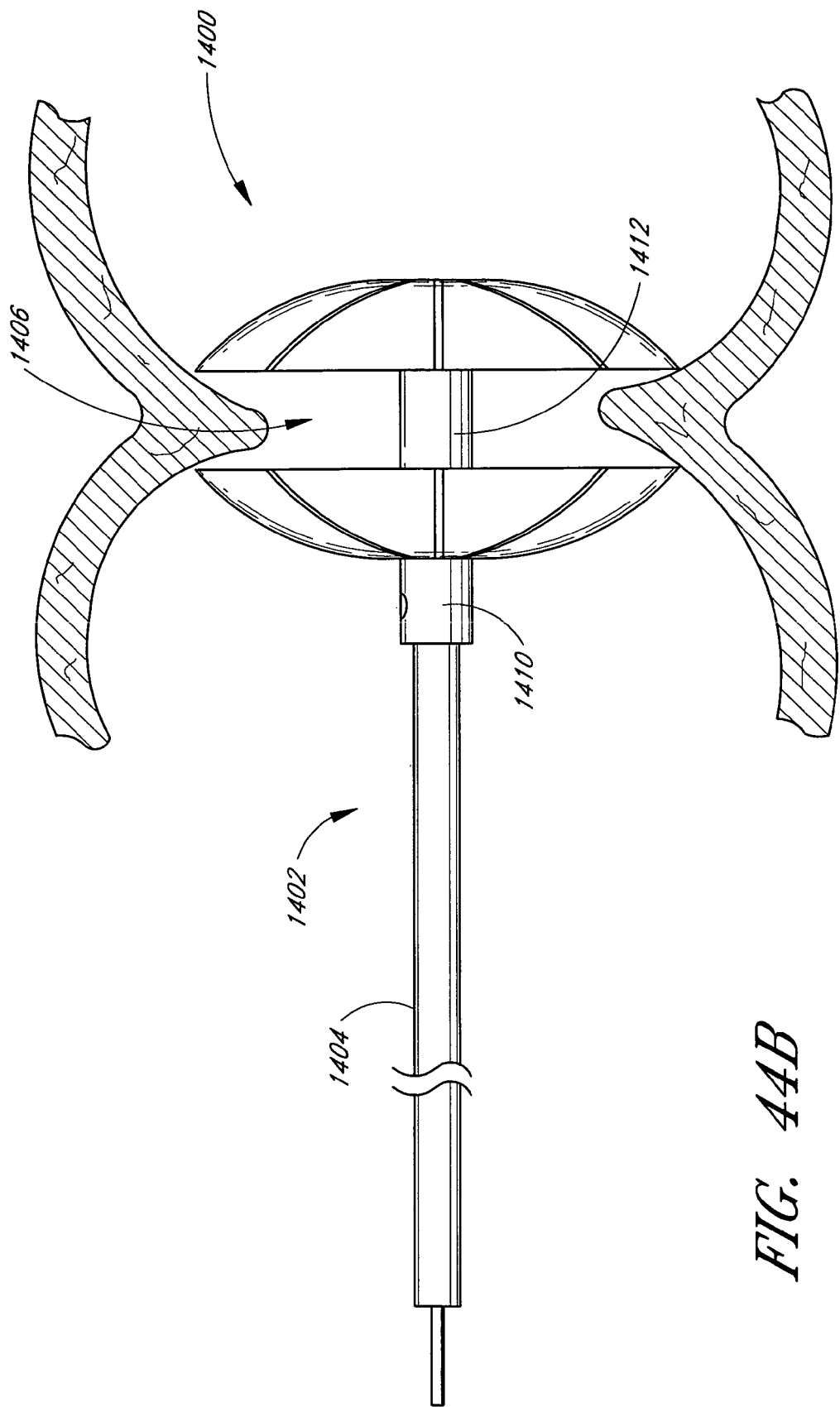
Figure 44C:
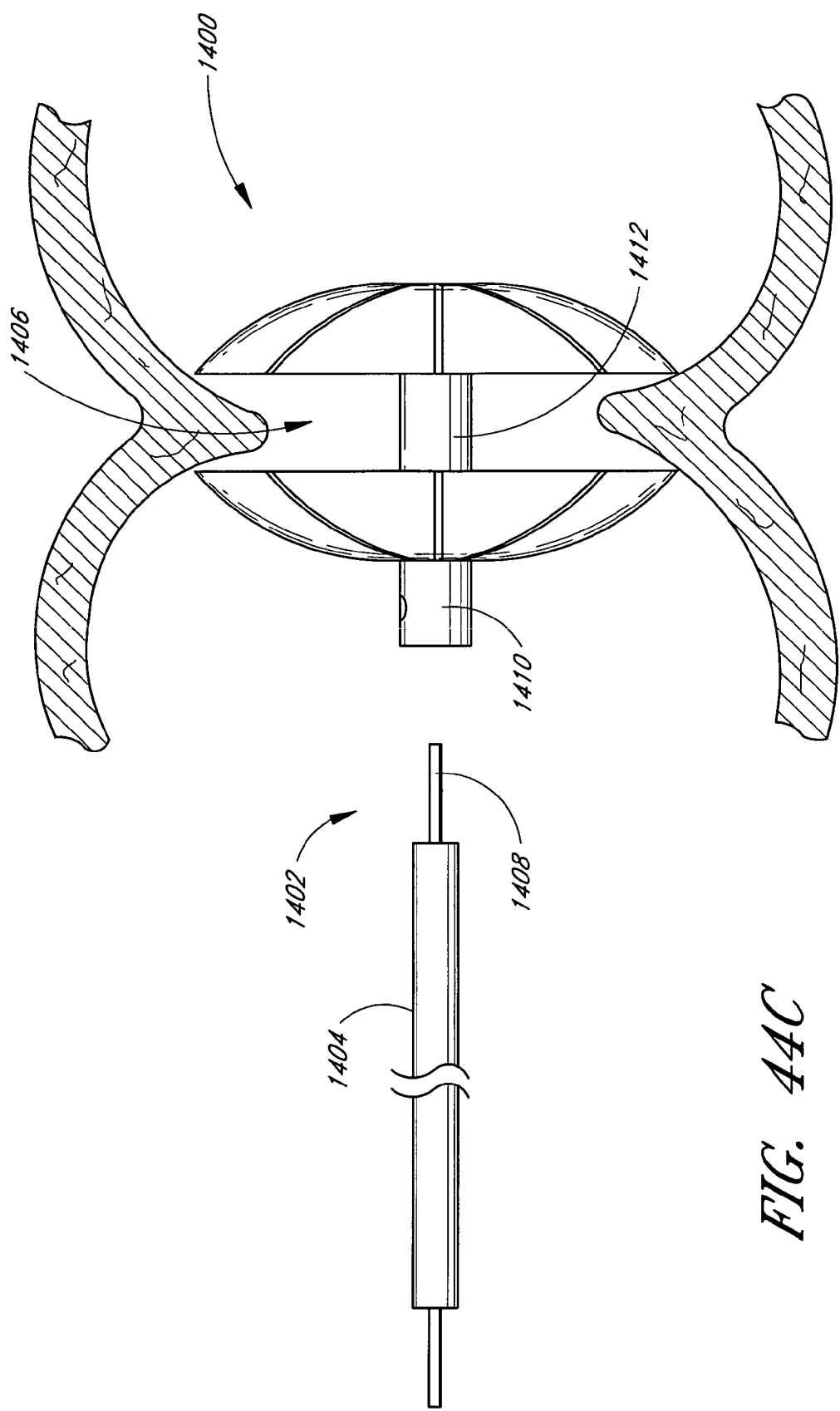

Referring to FIGS. 44A-C, a closure device 1400 is preferably positioned within a septal defect to be occluded, such as a patent foramen ovale or an atrial septal defect. In a patent foramen ovale application, the distal end 1402 of the delivery catheter 1404 is positioned at or near the patent foramen ovale 120. The position may be confirmed using fluoroscopy, echocardiography, or other imaging. The device 1400 is initially in a collapsed state in catheter 1404. The actuator 1408 (shown in FIG. 44C) is thereafter proximally retracted or rotated, as with a torque rod, to place and expand the closure device 1400 at the patent foramen ovale 120.

As will be apparent from FIG. 44B, proximal retraction or rotation on the actuator 1408 while resisting proximal movement of proximal hub 1410 such as by using the distal end of the catheter 1404 will cause the distal hub 1412 to be drawn towards the proximal hub 1410. The closure device 1400 engages the septa walls thereby closing the patent foramen ovale.

The actuator may then be locked with respect to the proximal hub and severed or otherwise detached to enable removal of the deployment catheter and proximal extension of the actuator. Locking of the actuator 1408 with respect to the closure device 1400 may be accomplished in a variety of ways, such as by using interference fit or friction fit structures, adhesives, a knot or other techniques depending upon the desired catheter design, as discussed herein. After the device 1400 is locked in placed, the catheter 1402 is detached from the device 1400 and removed from the patient. See FIG. 44. The device 1400 can also be captured and retrieved at any time during the procedure as long as it is not detached from the delivery catheter.

Figure 46:
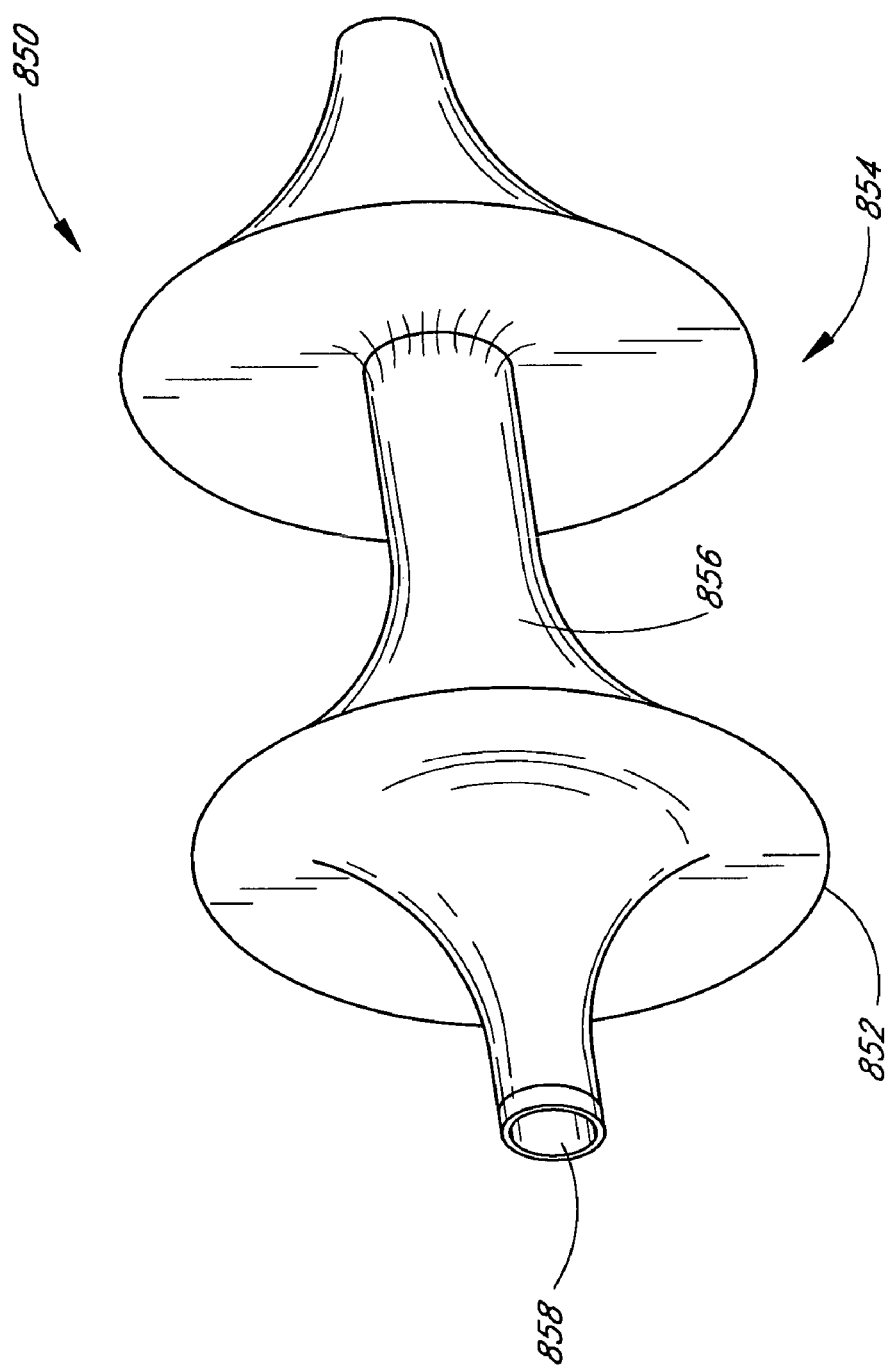
FIG. 46 is a perspective view of a closure device in accordance with another embodiment of the present invention.

With reference to FIG. 46, an alternative embodiment of the closure device is shown. The closure device 850 comprises a proximal inflatable balloon 852 and a distal inflatable balloon 854 joined together at a central hub 856. The device 850 may also comprise a frame, comprising a plurality of supports. The device 850 is preferably expanded by inflating the balloons 852, 854 via an inflation catheter by inserting inflation fluid through inflation lumen 858. The central hub 856 is positioned within the patent foramen ovale, while the proximal balloon 852 is preferably positioned in the right atrium and the distal balloon 854 is positioned in the left atrium, to occlude the patent foramen ovale.

Any modifications to the device to accommodate these various aspects of the closure device as discussed herein may be readily accomplished by those of skill in the art in view of the disclosure herein.

Tack Embodiments

Figure 48:
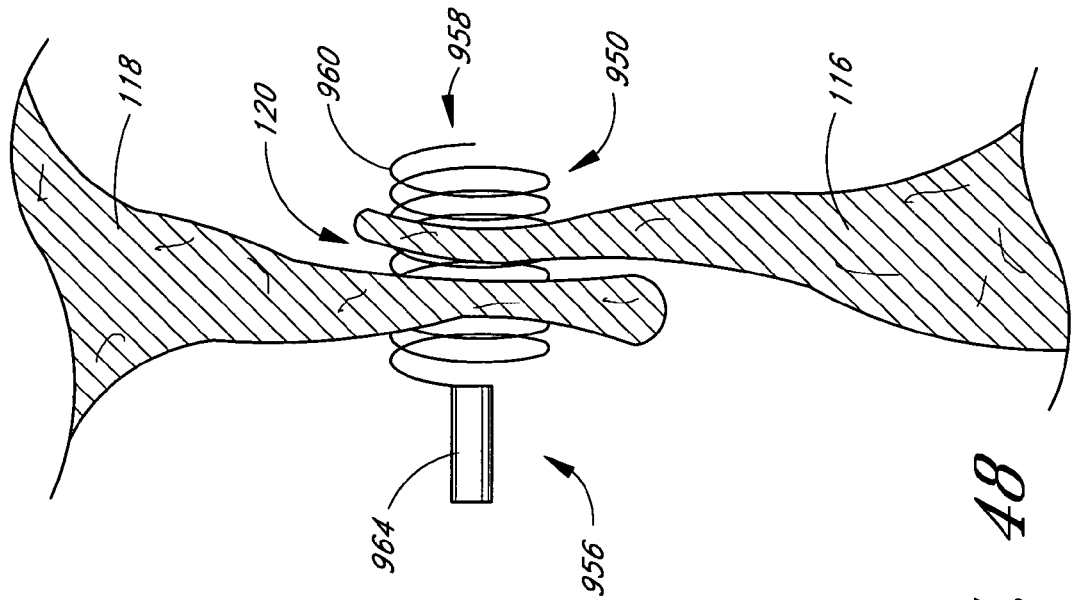
FIG. 48 is a cross-sectional view of a patent foramen ovale closed with a closure device in accordance with another embodiment of the present invention.
Figure 47:
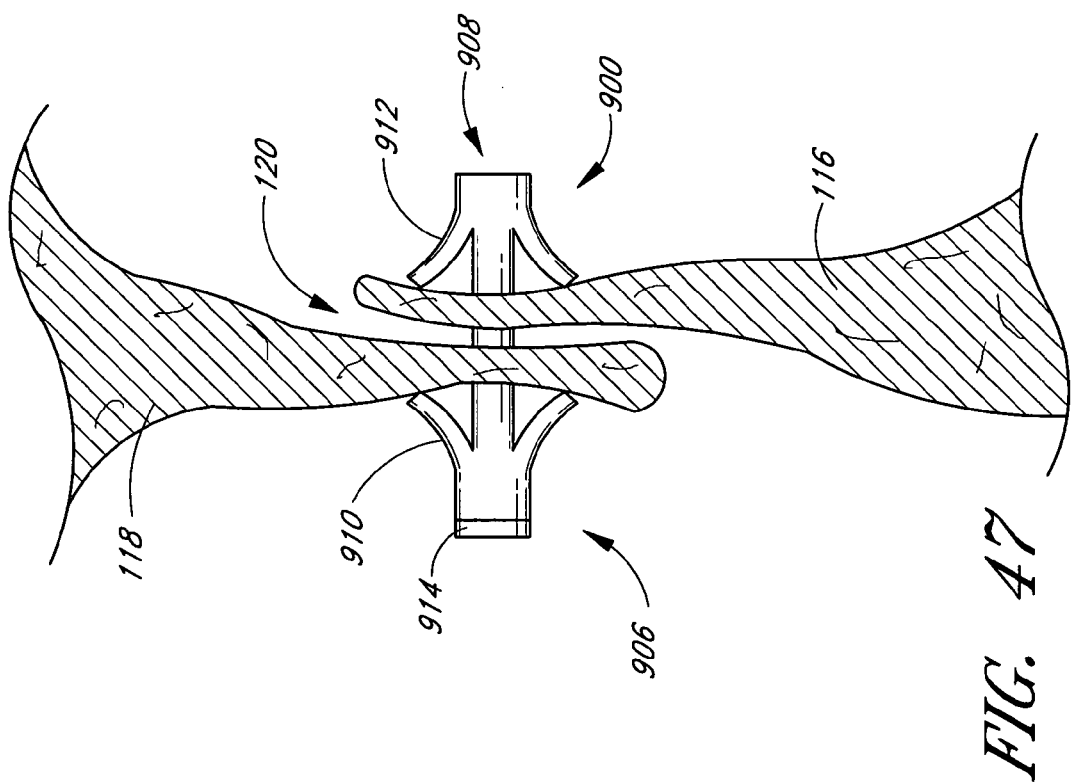
FIG. 47 is a cross-sectional view of a patent foramen ovale closed with a closure device in accordance with another embodiment of the present invention.

With reference to FIGS. 47 and 48, alternative embodiments are shown. In these embodiments, the patent foramen ovale is simply held together by positioning a device 900, 950 to hold the septum primum 116 and septum secundum 118 together. In a first embodiment, the device 900 comprises a proximal end 906 and a distal end 908, having a proximal anchor 910 and a distal anchor 912. Alternatively, a device 950 comprises a proximal end 956 and a distal end 958. The device has a screw-like configuration and comprises a coiled wire or threaded screw 960. The proximal end 906, 956 is preferably positioned in the right atrium, while the distal end 908, 958 is positioned in the left atrium. The device 900, 950 includes a detachment zone 914, 964. The device may also be provided with a sleeve, as has been discussed with previous embodiments.

Preferably, the device 900, 950 is formed of a metal such as stainless steel, Nitinol, Elgiloy, or others which can be determined through routine experimentation by those of skill in the art. The wire may also be biodegradable. Wires having a circular or rectangular cross-section may be utilized depending upon the manufacturing technique. In one embodiment, a circular cross section wire is cut such as by known laser cutting techniques from tube stock. The closure device is preferably an integral structure, such as a single ribbon or wire, or element cut from a tube stock.

Figure 49:
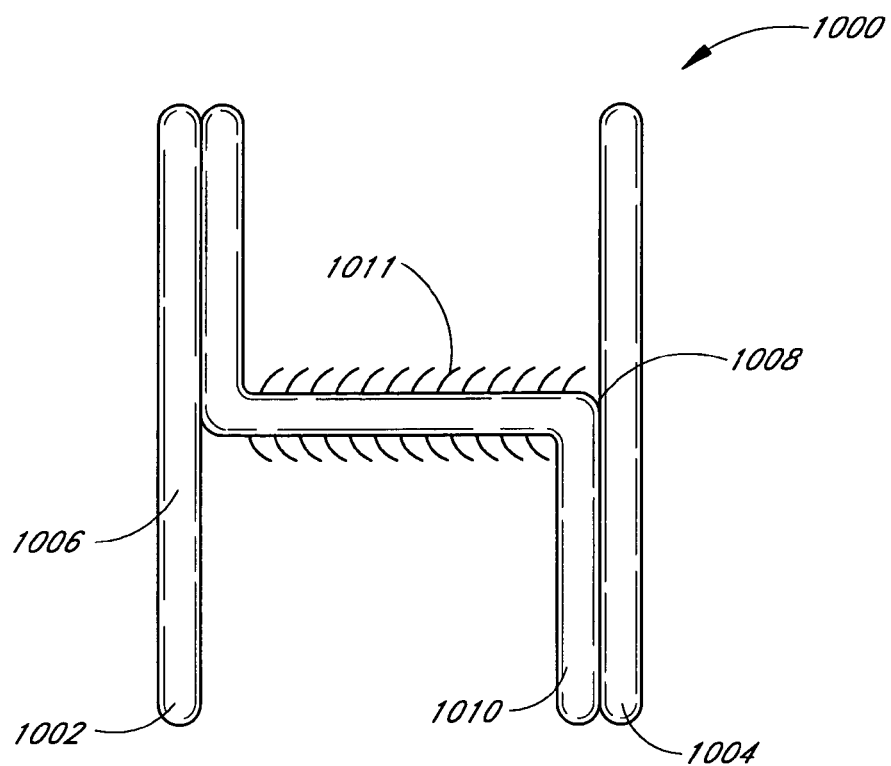
FIG. 49 is a side elevational view of a closure device in accordance with another embodiment of the present invention.
Figure 50:
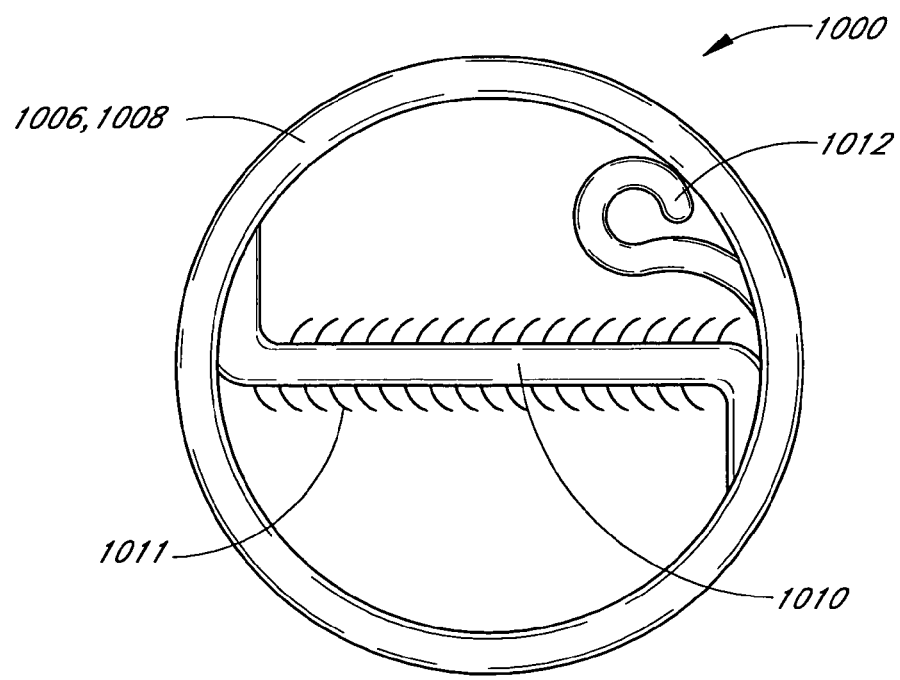
FIG. 50 is a front view of the closure device of FIG. 49.
Figure 51:
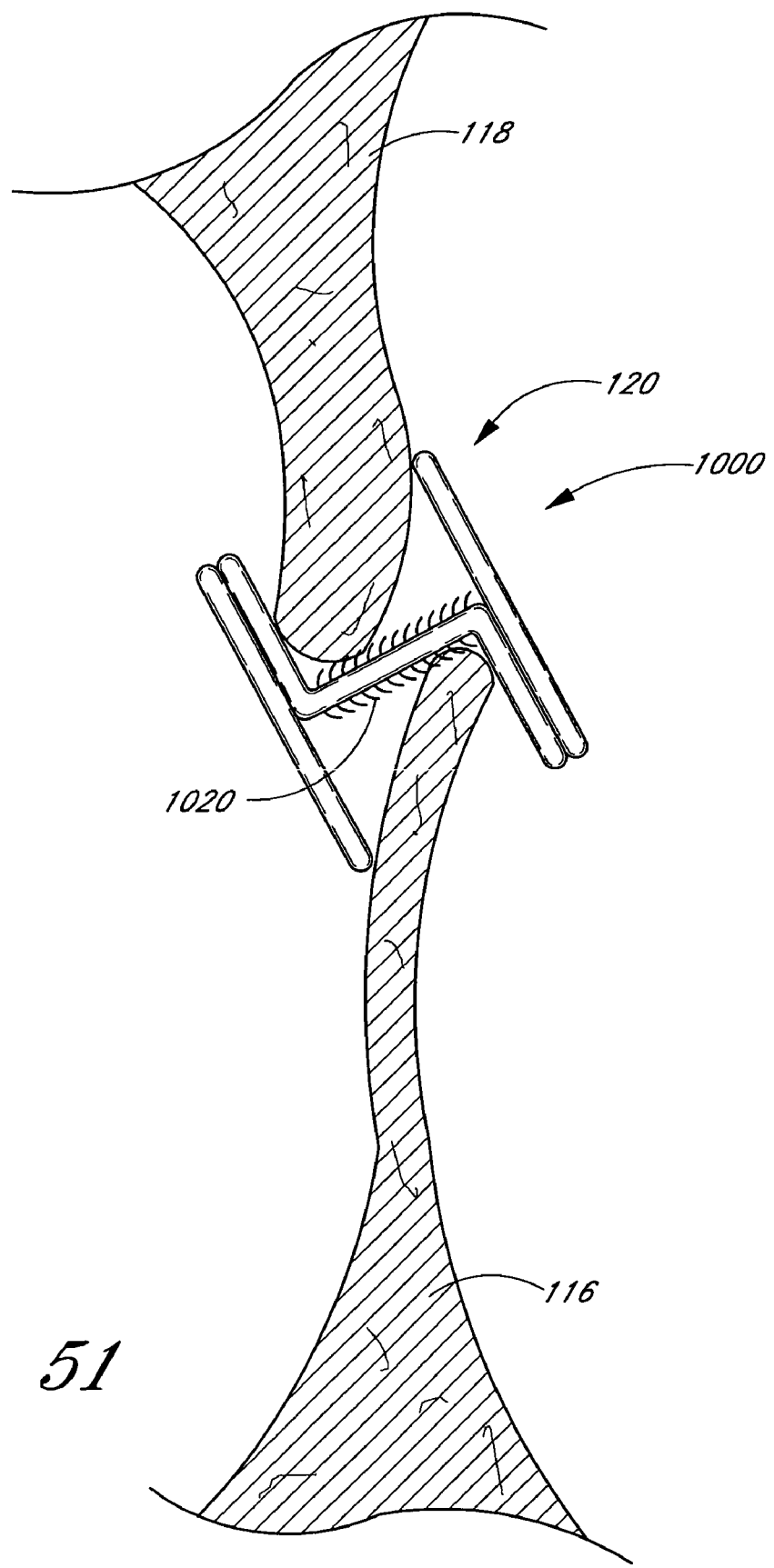
FIG. 51 is a cross-sectional view of a patent foramen ovale closed with the closure device of FIG. 40.

In another preferred embodiment, with reference to FIGS. 49-51, a closure device 1000 comprising a closure member is shown. The device comprises a proximal end 1002 and a distal end 1004, and a circular proximal section 1006 and circular distal section 1008, which are connected via a center strut 1010, forming an integral structure. The center strut 1010 preferably contains a closure or thrombotic material 1011. A loop 1012 is provided for holding and retrieving the device 1000. The proximal and distal sections 1006, 1008 act like springs, and maintain stability and help to squeeze the patent foramen ovale.

The center strut 1010 rests within the patent foramen ovale 120 for occluding the channel 122, engaging the septum primum 116 and the septum secundum 118. The proximal section 1006 is preferably positioned in the right atrium, while the distal section 1008 is positioned in the left atrium.

Preferably, the device 1000 is formed of a metal such as stainless steel, Nitinol, Elgiloy, or others which can be determined through routine experimentation by those of skill in the art. The wire may also be biodegradable. Wires having a circular or rectangular cross-section may be utilized depending upon the manufacturing technique. In one embodiment, a circular cross section wire is cut such as by known laser cutting techniques from tube stock. The closure device is preferably an integral structure, such as a single ribbon or wire, or element cut from a tube stock.

The thrombotic material 1011 may include DACRON™, or others which can be determined through routine experimentation by those of skill in the art.

Channel-Filling Embodiments

Figure 52:
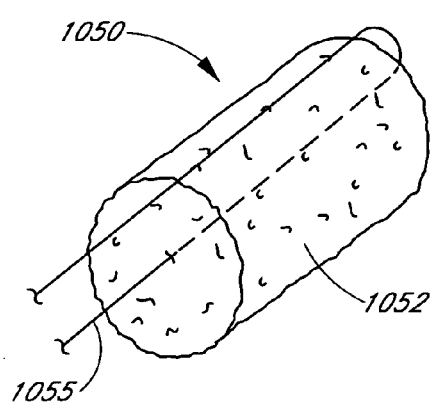
FIG. 52 is a perspective view of a closure device in accordance with another embodiment of the present invention.
Figure 53:
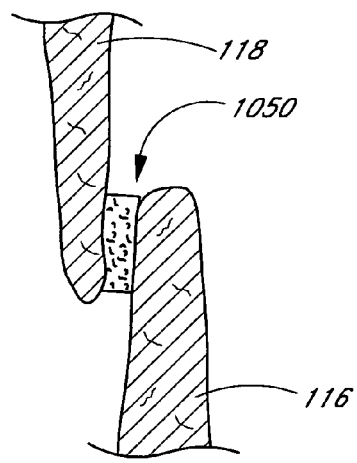
FIG. 53 is a cross-sectional view of a patent foramen ovale closed with the closure device of FIG. 52.

With reference to FIG. 52, there is illustrated another preferred embodiment of the present invention. A closure device 1050 comprising a porous sponge or sponge-like material is shown. Alternatively, the closure device 1050 may comprise a fluid-filled bag with a porous or semi-porous other covering. In some embodiments, the closure device 1050 has a generally cylindrical shape. In some embodiments, the sponge is at least as large as the defect to be filled. In some embodiments, tether 1055 extends through closure device 1050 and is used to attach closure device 1050 to delivery catheter 1504. FIG. 53 illustrates the sponge-like closure device 1050 positioned at a patent foramen ovale. The sponge expands upon placement to close the defect and is secured in place by the septum primum 116 and septum secundum 118.

In some embodiments, the sponge or sponge-like material may comprise collagen, PE, PTFE, Poly Vinyl Acetate (Ivalon), or Ethyl Vinyl Acetate. In some embodiments, the material may be bioresorbable. In some embodiments, the sponge promotes tissue ingrowth for more complete sealing of a septal defect, such as a patent foramen ovale.

Figure 54:
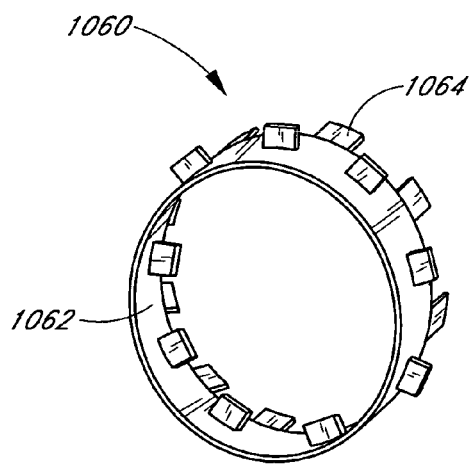
FIG. 54 is a perspective view of a closure device in accordance with another embodiment of the present invention.

With reference to FIG. 54, an anchor device 1060 is illustrated. The anchor device 1060 comprises a frame 1062 having a plurality of retention elements 1064 provided thereon. In some embodiments, the frame may be perforated, while in other embodiments, the frame is solid.

Figure 55:
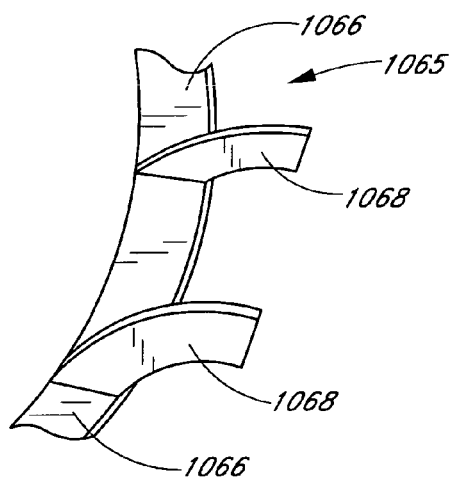
FIG. 55 is an enlarged perspective view of a closure device in accordance with another embodiment of the present invention.
Figure 56:
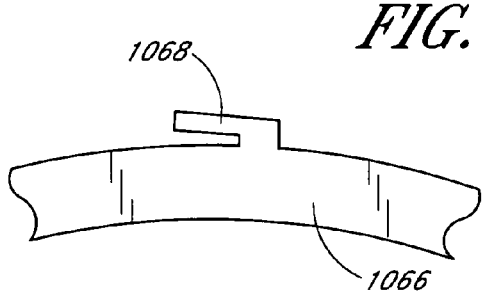
FIG. 56 is a side view of the closure device of FIG. 55.

In some embodiments, the anchor device 1060 may be comprised of a plurality of laser cut strips 1065, as shown in FIG. 55. The laser cut strips comprise a laser-cut body 1066 which can be twisted to reveal anchors 1068. A detailed view of the body 1066 and anchors 1068 is shown in FIG. 56. By linking together a plurality of the laser cut strips 1065, a lattice of anchoring surfaces can be formed. The lattice of anchoring surfaces can also be placed within or through a patent foramen ovale.

Figure 57:
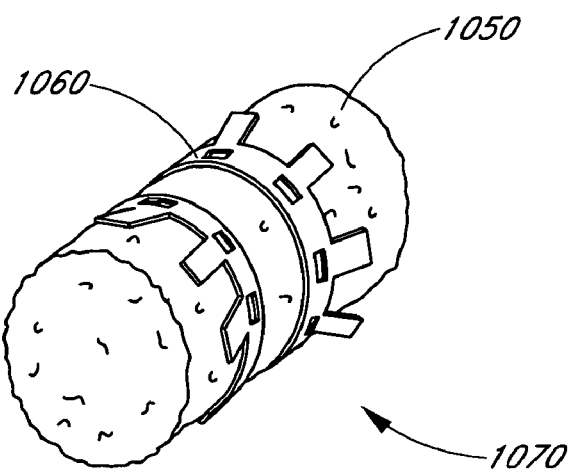
FIG. 57 is a perspective view of a closure device in accordance with another embodiment of the present invention.
Figure 58:
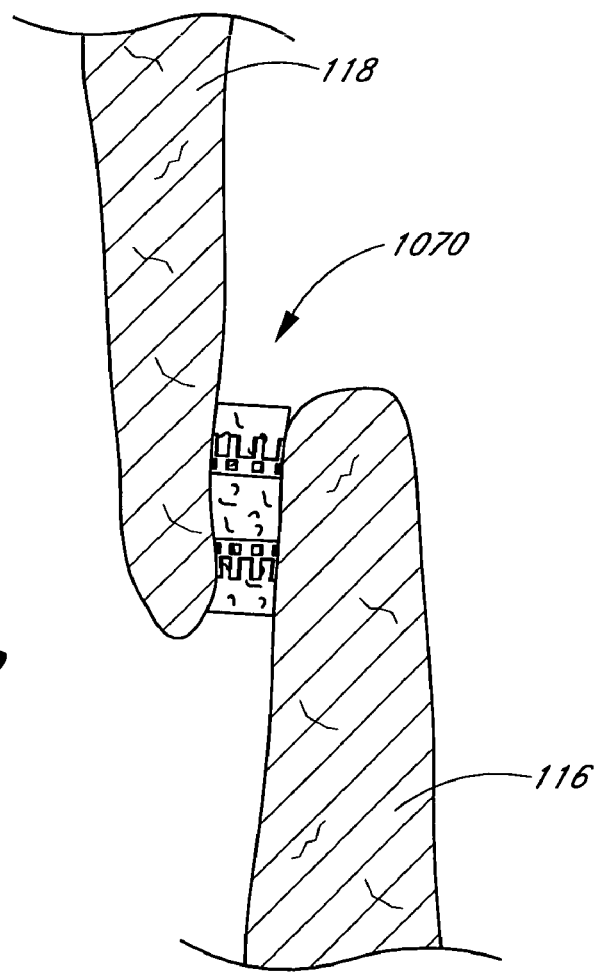
FIG. 58 is a cross-sectional view of a patent foramen ovale closed with the closure device of FIG. 57.

As shown in FIG. 57, the anchor device 1060 may be used with the sponge-like closure device 1050 to form an anchored sponge closure device 1070. The anchors may be used to further secure the sponge-like closure device in place. FIG. 58 illustrates closure device 1070, wherein anchor devices 1060 secure the sponge-like closure device 1050 at a defect.

Figure 59A:
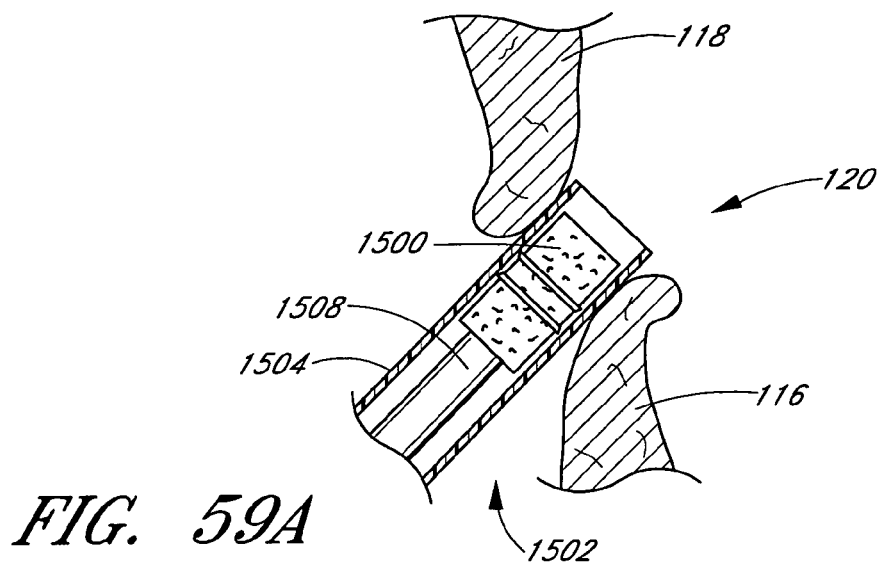
FIGS. 59A-C are schematic views of a defect closure procedure in accordance with one embodiment of the present invention.
Figure 59B:
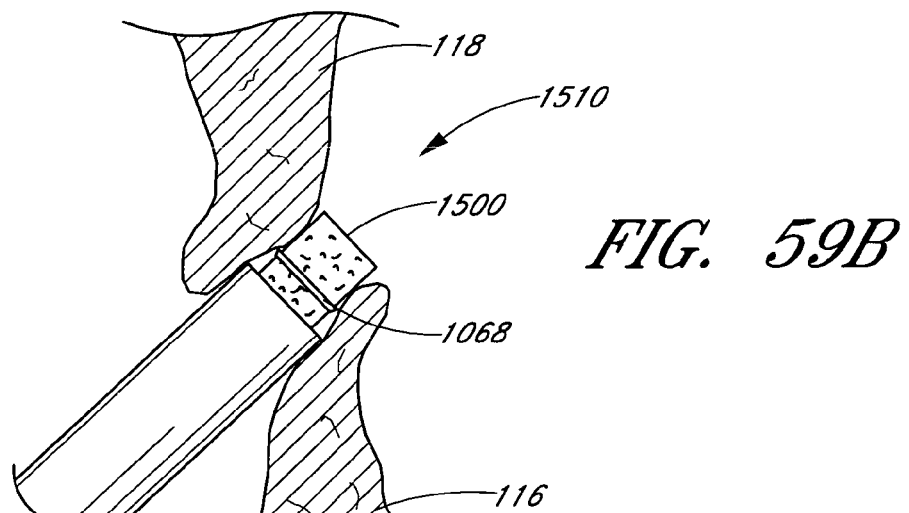
Figure 59C:
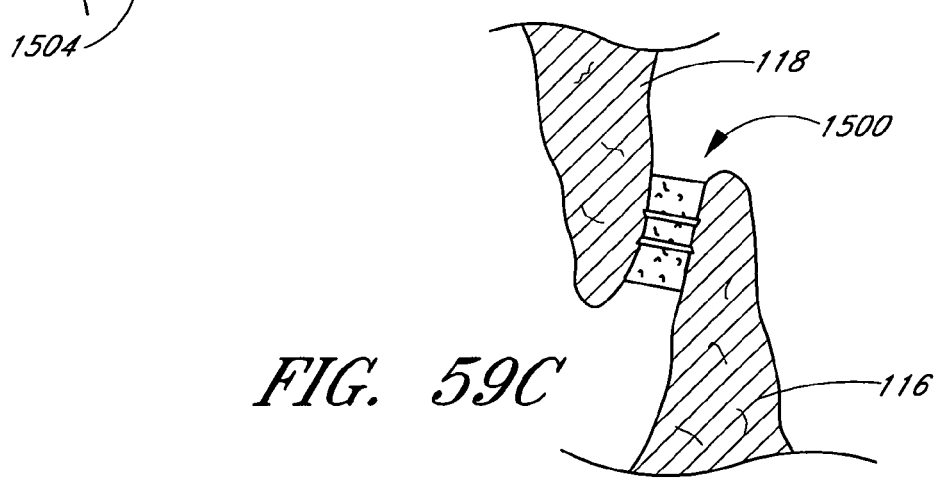

Referring to FIG. 59A-C, a preferably method is shown of deploying the closure device 1500 within a septal defect, such as a patent foramen ovale. In a patent foramen ovale application, the distal end 1502 of the delivery catheter 1504 is positioned at or near the patent foramen ovale 120, as shown in FIG. 59A. The position may be confirmed using fluoroscopy, echocardiography, or other imaging. The device 1500 is initially in a collapsed state within catheter 1504. The device 1500 may be releasably attached to an actuator 1508. The distal end 1502 of the delivery catheter 1504 is advanced between the septum primum 116 and septum secundum 118 as shown, and the posterior portion 1510 is advanced out of the distal end 1502 of the delivery catheter 1504, as shown in FIG. 59B. The intermediate section and posterior sections are then delivered, as shown in FIG. 59C. After optimal positioning and sealing is achieved, the device 1500 can then be detached from the delivery catheter 1504.

Any of the closure devices disclosed herein may also be coated with a therapeutic substance, such as an anti-thrombogenic drug. The therapeutic substances are typically either impregnated into the device or carried in a polymer that coats the device. The therapeutic substances are released from the device or polymer once it has been implanted in the vessel. The device may be impregnated with at least one drug or coated with at least one drug by any known process in the art. The drug may be carried in a volatile or non-volatile solution. As used in this application, the term "drug" denotes any compound which has a desired pharmacological effect, or which is used for diagnostic purposes.

Furthermore, the closure devices as disclosed herein are preferably asymmetrical. As has been discussed, the axis of a patent foramen ovale tends to be at an angle, and almost parallel to the septal wall. Accordingly, asymmetrical closure devices will be effective in closing septal defects having non-longitudinal axes, such as a patent foramen ovale.

As a post implantation step for any of the closure devices disclosed herein, a radiopaque dye or other visualizable media may be introduced on one side or the other of the closure device, to permit visualization of any escaped blood or other fluid past the closure device. For example, in the context of a patent foramen ovale application, the closure device may be provided with a central lumen or other capillary tube or aperture which permits introduction of a visualizable dye from the deployment catheter through the closure device and into the space on the distal side of the closure device.

While particular forms of the invention have been described, it will be apparent that various modifications can be made without departing from the spirit and scope of the invention. Accordingly, it is not intended that the invention be limited, except as by the appended claims.

What is claimed is:

1. A method of closing a patent foramen ovale having a channel formed between overlapping surfaces of a septum primum and a septum secundum, the septum primum having a proximal surface and a distal surface adjacent the left atrium, the septum secundum having a proximal surface adjacent the right atrium and a distal surface, the channel disposed between the overlapping proximal surface of the septum primum and the distal surface of the septum secundum, the method comprising:

providing a closure device having a proximal end, a distal end, a proximal segment, an intermediate segment and a distal segment, the proximal and intermediate segments defining a first clip-shaped portion and the intermediate and distal segments defining a second clip-shaped portion, wherein the closure device is self-expandable to a deployment shape wherein the proximal, intermediate and distal segments are generally parallel to one another;

deploying the closure device at the patent foramen ovale such that the second clip-shaped portion is positioned over a tip of the septum primum and the first clip-shaped portion is positioned over a tip of the septum secundum, with the intermediate segment lying in the channel between the overlapping septum primum and the septum secundum; and locking the position of the proximal segment, the intermediate segment and the distal segment of the closure device after deployment with a locking element;

wherein the closure device when locked exerts a force to draw the septum primum and septum secundum together in an overlapping configuration to close the channel formed between the overlapping proximal surface of the septum primum and the distal surface of the septum secundum;

wherein the locking element remains at the patent foramen ovale after locking.

2. The method of claim 1, wherein the intermediate and distal segments of the closure device when deployed are positioned along the proximal and distal surfaces, respectively, of the septum primum and the proximal and intermediate segments of the closure device when deployed are positioned along the proximal and distal surfaces, respectively, of the septum secundum.

3. The method of claim 1, wherein the first clip-shaped portion and second clip-shaped portions are integrally formed.

4. The method of claim 1, wherein the first clip-shaped portion and second clip-shaped portions are made of wire.

5. The method of claim 1, wherein the first clip-shaped portion and second clip-shaped portions when the device is deployed forms generally an S-shape.

6. The method of claim 1, wherein each clip-shaped portion is formed from two adjacent loops connected by a connecting portion.

7. The method of claim 1, wherein deploying the closure device comprises releasing the closure device from a detachment element provided on the device.

8. The method of claim 1, wherein the intermediate segment comprises at least two side-by-side wire portions.

9. The method of claim 1, wherein the locking element is provided as a retained part of the closure device after deployment.

10. The method of claim 1, wherein the locking element connects to the proximal and distal ends of the device, and locking the position of the closure device after deployment comprises longitudinally shortening and radially expanding the device.

11. The method of claim 10, wherein the locking element comprises a locking string connected to eyelets provided on the closure device.

12. A method of closing a patent foramen ovale having a channel formed between overlapping surfaces of a septum primum and a septum secundum, the septum primum having a proximal surface and a distal surface adjacent the left atrium, the septum secundum having a proximal surface adjacent the right atrium and a distal surface, the channel disposed between the overlapping proximal surface of the septum primum and the distal surface of the septum secundum, the method comprising:

providing a closure device having a proximal end and a distal end and having a generally elongate configuration and a clip configuration, wherein when the closure device is in its elongate configuration the proximal and distal ends are pulled away from each other and when the closure device is in its clip configuration the closure device has generally an S-shape, the closure device being releasably attached relative to a delivery device;

delivering the closure device to the patent foramen ovale with the delivery device, the closure device being held relative to the delivery device in its elongate configuration;

deploying the closure device in the channel of the patent foramen ovale, wherein the closure device when deployed includes a first clip-shaped portion positioned around the septum secundum and a second clip-shaped portion positioned around the septum primum; and locking the closure device in its clip configuration after deployment with a locking element to increase the clamping force of the closure device on the septa of the patent foramen ovale;

wherein the closure device when deployed exerts a force to draw the overlapping septum primum and septum secundum together in an overlapping configuration to close the channel disposed between the overlapping proximal surface of the septum primum and the distal surface of the septum secundum;

wherein the locking element remains at the patent foramen ovale after locking.

13. The method of claim 12, wherein the closure device includes a detachment element at its proximal end, and the closure device is delivered using a core wire that releasably engages the detachment element.

14. The method of claim 12, wherein the closure device is held in its elongate configuration distal to a deployment catheter.

15. The method of claim 12, wherein the closure device is delivered by positioning a catheter between the septum primum and septum secundum.

16. The method of claim 12, wherein the closure device self-expands to its deployment configuration.

17. The method of claim 12, wherein the closure device includes a plurality of eyelets, and the closure device is releasably attached to the delivery device by engaging a core through at least some of the eyelets.

18. The method of claim 12, wherein the locking element is provided as a retained part of the closure device after deployment.

19. The method of claim 12, wherein the locking element connects to the proximal and distal ends of the device, and locking the closure device in its clip configuration after deployment comprises longitudinally shortening and radially expanding the device.

20. The method of claim 19, wherein the locking element comprises a locking string connected to eyelets provided on the closure device.

* * * * *

UNITED STATES PATENT AND TRADEMARK OFFICE
CERTIFICATE OF CORRECTION

| | | |
|---|---|---|
| PATENT NO. | : 7,780,700 B2 | Page 1 of 1 |
| APPLICATION NO. | : 10/771845 | |
| DATED | : August 24, 2010 | |
| INVENTOR(S) | : Frazier et al. | |

It is certified that error appears in the above-identified patent and that said Letters Patent is hereby corrected as shown below:

On the Title Page, (Item 60), under Related U.S. Application Data, Line 1, change "60/446,088," to --60/445,088,--.

In Column 7, Line 15, change "arteriosis" to --arteriosus--.

In Column 11, Line 55, change "actutator" to --actuator--.

In Column 12, Line 56, change "actutator" to --actuator--.

In Column 16, Line 2, change "sheet" to --sheet.--.

Signed and Sealed this
Twenty-ninth Day of March, 2011

David J. Kappos
*Director of the United States Patent and Trademark Office*